United States Patent
Fassler et al.

(10) Patent No.: US 11,512,125 B2
(45) Date of Patent: Nov. 29, 2022

(54) ANTIBODIES FOR THE TREATMENT OF SYNUCLEINOPATHIES AND NEUROINFLAMMATION

(71) Applicant: Mor Research Applications, Tel Aviv (IL)

(72) Inventors: Michael Fassler, Ness Ziona (IL); Jacob George, Tel Aviv (IL)

(73) Assignee: Mor Research Applications

( * ) Notice: Subject to any disclaimer, the term of this patent is extended or adjusted under 35 U.S.C. 154(b) by 30 days.

(21) Appl. No.: 17/255,776

(22) PCT Filed: Jun. 27, 2019

(86) PCT No.: PCT/IB2019/055461
§ 371 (c)(1),
(2) Date: Dec. 23, 2020

(87) PCT Pub. No.: WO2020/003203
PCT Pub. Date: Jan. 2, 2020

(65) Prior Publication Data
US 2021/0214429 A1    Jul. 15, 2021

Related U.S. Application Data

(60) Provisional application No. 62/690,733, filed on Jun. 27, 2018.

(51) Int. Cl.
*C07K 16/18* (2006.01)
*G01N 33/68* (2006.01)
*A61P 25/14* (2006.01)

(52) U.S. Cl.
CPC .............. *C07K 16/18* (2013.01); *A61P 25/14* (2018.01); *G01N 33/6896* (2013.01); *C07K 2317/21* (2013.01); *C07K 2317/52* (2013.01); *C07K 2317/55* (2013.01); *C07K 2317/622* (2013.01)

(58) Field of Classification Search
None
See application file for complete search history.

(56) References Cited

FOREIGN PATENT DOCUMENTS

| WO | WO-2010069603 A1 | 6/2010 |
|----|------------------|--------|
| WO | WO-2014058924 A2 | 4/2014 |
| WO | WO-2020003203 A1 | 1/2020 |

OTHER PUBLICATIONS

Beaudoin 3rd, G. M. J., et al., "Culturing Pyramidal Neurons From the Early Postnatal Mouse Hippocampus and Cortex," *Nature Protocols* 7(9):1741-1754, Nature Pub. Group, United Kingdom (Sep. 2012).

Braak, H., et al., "Staging of Brain Pathology Related to Sporadic Parkinson's Disease," *Neurobiology of Aging* 24(2):197-211, Elsevier, United States (Mar.-Apr. 2003).

Brundin, P., et al., "Therapeutic approaches to target alpha-synuclein pathology," *Experimental Neurology* 298(Pt B):225-235, Academic Press, United States (Dec. 2017).

(Continued)

*Primary Examiner* — Aurora M Fontainhas
(74) *Attorney, Agent, or Firm* — Sterne, Kessler, Goldstein & Fox P.L.L.C.

(57) ABSTRACT

Anti-alpha-synuclein antibodies and antigen-binding fragments thereof (e.g., scFvs) are provided. Also provided are methods of using the same in therapy.

20 Claims, 34 Drawing Sheets
Specification includes a Sequence Listing.

(56) References Cited

OTHER PUBLICATIONS

Burre, J., et al., "Alpha-synuclein promotes SNARE-complex assembly in vivo and in vitro," *Science* 329(5999):1663-1667, American Association for the Advancement of Science, United States (Sep. 2010).

Burre, J., et al., "Properties of Native Brain alpha-Synuclein," *Nature* 498(7453):E4-E6, Nature Publishing Group, United Kingdom (Jun. 2013).

Carter, R. J., et al., "Characterization of progressive motor deficits in mice transgenic for the human Huntington's disease mutation," *The Journal of Neuroscience* 19(8):3248-3257, Society for Neuroscience, United States (Apr. 1999).

Chinta, S. J., et al., "Mitochondrial α-synuclein accumulation impairs complex I function in dopaminergic neurons and results in increased mitophagy in vivo," *Neuroscience Letters* 486(3):235-239, Elsevier Scientific Publishers, Ireland (Dec. 2010).

Colonna, M. and Butovsky, O., "Microglia Function in the Central Nervous System During Health and Neurodegeneration," *Annual Review of Immunology* 35:441-468, Annual Reviews Inc., United States (Apr. 2017).

El-Agnaf, O. M. A., et al., "Detection of oligomeric forms of alpha-synuclein protein in human plasma as a potential biomarker for Parkinson's disease," *FASEB Journal* 20(3):419-425, Wiley, United States (Mar. 2006).

Emadi, S., et al., "Isolation of a human single chain antibody fragment against oligomeric alpha-synuclein that inhibits aggregation and prevents alpha-synuclein-induced toxicity," *Journal of Molecular Biology* 368(4):1132-1144, Elsevier, United Kingdom (May 2007).

Hansen, C., et al., "α-Synuclein propagates from mouse brain to grafted dopaminergic neurons and seeds aggregation in cultured human cells," *The Journal of Clinical Investigation* 121(2):715-725, American Society for Clinical Investigation, United States (Feb. 2011).

International Search Report and Written Opinion for International Application No. PCT/IB2019/055461, Israel Patent Office, Israel, dated Nov. 18, 2019, 16 pages.

Jakes, R., et al., "Identification of two distinct synucleins from human brain," *FEBS Letters* 345(1):27-32, John Wiley & Sons Ltd., United Kingdom (May 1994).

Lynch, S. M., et al., "An scFv Intrabody Against the Nonamyloid Component of alpha-synuclein Reduces Intracellular Aggregation and Toxicity," *Journal of Molecular Biology* 377(1):136-147, Elsevier, United Kingdom (Mar. 2008).

Masliah, E., et al., "Effects of Alpha-synuclein Immunization in a Mouse Model of Parkinson's Disease," *Neuron* 46(6):857-868, Cell Press, United States (Jun. 2005).

Zha, J., et al., "A scFv antibody targeting common oligomeric epitope has potential for treating several amyloidoses," *Scientific Reports* 6:36631, Nature Publishing Group, United Kingdom (Nov. 2016), 15 pages.

FIG. 3A

PMS209 VH (Fab2 VH) (SEQ ID NO:19):

ATGAAATACCTATTGCCTACGGCAGCCGCTGGATTGTTATTACTCGCGGCCCAGCCGGCCATGGCC
CAGGTGCAGCTGCAGGAGTCGGGCCCAGGACTGGTGAAGCCCTCGGAGACCCTGTCCCTCACCTG
CACTGTCTCTGGTGGCTCCATCAGCAGTAGTAGTTACTACTGGGGCTGGATCCGCCAGCCCCAG
GGAAGGGGCTGGAGTGGATTGGGAGTATCTATTATAGTGGGAGCACCTACTACAACCCGTCCCTCA
AGAGTCGAGTCACCATATCCGTAGACACGTCCAAGAACCAGTTCTCCCTGAAGCTGAGCTCTGTGAC
CGCCGCAGACACGGCTGTGTATTACTGT**GCGAGACTCCGTCGCTATGATAGTAGTGGTTTTTTCTTT
GACTAC**TGGGGCCAGGGAACCCTGGTCACCGTCTCAAGCGCCTCCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTCCACACCT
TCCCGGCTGTCCTACAGTCCTCAGGACTCTACTCCCTCAGCAGCGTAGTGACCGTGCCCTCCAGCA
GCTTGGGCACCCAGACCTACATCTGCAACGTGAATCACAAGCCCAGCAACACCAAGGTGGACAAGA
AAGTTGAGCCCAAATCTTGTGCGGCCGCACATCATCATCACCATCACGGGGCCGCAGAACAAAAACT
CATCTCAGAAGAGGATCTGAATGGGGCCGCATAG

PMS209 VL (Fab2 VL) (SEQ ID NO:20):

GTGAAAAAATTATTATTCGCAATTCCTTTAGTTGTTCCTTTCTATTCTCACAGTGCACAGTCTGTCGTG
ACGCAGCCGCCCTCAGTGTCTGCGGCCCAGGACAGAAGGTCACCATCTCCTGCTCTGGAAGC**AG
CTCCAACATTGGGAATAATTA**TGTATCCTGGCATCAGCAGCTCCCAGGAACAGCCCCCAAAACTCCT
CATTTATGACAATGATAGGCGACCCTCAGGGATTCCTGACCGATTCTCTGGCTCCAAGTCTGGCACG
TCAGCCACCCTGGCCATCACCGGACTCCAGACTGGGGACGAGGCCGACTATTACTGC**GGAACATG
GGATAGCAGCCTGAGTGGGGAGTG**TTCGGCGGAGGGACCAAGGTGACCGTCCTGAGTCAGCCC
AAGGCTGCCCCCTCGGTCACTCTGTTCCCACCCTCCTCTGAGGAGCTTCAAGCCAACAAGGCCACA
CTGGTGTGTCTCATAAGTGACTTCTACCCGGGAGCCGTGACAGTGGCCTGGAAGGCAGATAGCAGC
CCCGTCAAGGCGGGAGTGGAGACCACCACACCCTCCAAACAAAGCAACAACAAGTACGCGGCCAG
CAGCTACCTGAGCCTGACGCCTGAGCAGTGGAAGTCCCACAAAAGCTACAGCTGCCAGGTCACGCA
TGAAGGGAGCTCCGTGGAGAAGACAGTGGCCCCTGCAGAATGCTCTTAA

FIG. 3B

PMS210 VH (Fab3 VH) (SEQ ID NO:23):

ATGAAATACCTATTGCCTACGGCAGCCGCTGGATTGTTATTACTCGCGGCCCAGCCGGCCATGGCC
CAGGTGCAGCTGGTGCAGTCTGGGGGAGGCTTGGTACAGCCTGGGAGGTCCCTGCGACTCTCCTG
TGCAGCCTCT<u>GGATTCACCTTTAGCAACTATGCC</u>ATGAGCTGGGTCCGCCAGGCTCCAGGGAAGG
GGCTGGAGTGGGTCTCAGCT<u>ATTAGTGGTAGTGGTGGTAGCACA</u>TACTACGCAGACTCCGTGAAGG
GCCGGTTCACCATCTCCAGAGACAGTTCCAAGAACACGCTTTATCTTCAAATGAACGACCTGAGAGC
CGAGGACACGGCTATATATTACTGT<u>GCGAGAAGTTTCACTCTTGACTAT</u>TGGGGCCAGGGAACCCT
GGTCACCGTCTCAAGCGCCTCCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTCCACACCTTCCCGGCTGTCCTACAGTCCTCAG
GACTCTACTCCCTCAGCAGCGTAGTGACCGTGCCCTCCAGCAGCTTGGGCACCCAGACCTACATCT
GCAACGTGAATCACAAGCCCAGCAACACCAAGGTGGACAAGAAAGTTGAGCCCAAATCTTGTGCGG
CCGCACATCATCATCACCATCACGGGGCCGCAGAACAAAAACTCATCTCAGAAGAGGATCTGAATGG
GGCCGCATAG

PMS210 VL (Fab3 VL) (SEQ ID NO:24):

GTGAAAAAATTATTATTCGCAATTCCTTTAGTTGTTCCTTTCTATTCTCACAGTGCACTTTACTATGTGC
TGACTCAGCCACCCTCGGTGTCCAAGGGCTTGAGACAGACCGCCACACTCACCTGCACTGGGAAC<u>A</u>
<u>GCAACAATATTGGCAACCAAGGA</u>GCAGCTTGGCTGCAGCAGCACCAGGGCCACCCTCCCAAACTC
CTATCCTAC<u>AGGAATAAC</u>AACCGGCCCTCAGGGATCTCAGAGAGATTATCTGCATCCAGGTCAGGA
AATACTGCCTCCCTGACCATTACTGGACTCCAGCCTGAGGACGAGGCTGACTATTACTGC<u>TCATCAT</u>
<u>GGGACAGCAGTCTGAAAGTTCAGGTG</u>TTCGGCGGAGGGACCAAGCTGACCGTCCTAGGTCAGCCC
AAGGCTGCCCCCTCGGTCACTCTGTTCCCACCCTCCTCTGAGGAGCTTCAAGCCAACAAGGCCACA
CTGGTGTGTCTCATAAGTGACTTCTACCCGGGAGCCGTGACAGTGGCCTGGAAGGCAGATAGCAGC
CCCGTCAAGGCGGGAGTGGAGACCACCACACCCTCCAAACAAAGCAACAACAAGTACGCGGCCAG
CAGCTACCTGAGCCTGACGCCTGAGCAGTGGAAGTCCCACAAAAGCTACAGCTGCCAGGTCACGCA
TGAAGGGAGCACCGTGGAGAAGACAGTGGCCCCTACAGAATGTTCATAA

FIG. 3C

PMS211 VH (Fab4 VH) (SEQ ID NO:27):

ATGAAATACCTATTGCCTACGGCAGCCGCTGGATTGTTATTACTCGCGGCCCAGCCGGCCATGGCC
CAGGTGCAGCTGGTGCAGTCTGGGGCTGAGGTGAAGAAGCCTGGGTCCTCGGTGAAGGTCTCCTG
CAAGGCTTCTGGAGGCACCTTCAGCAGCTATGCTATCAGCTGGGTGCGACAGGCCCCTGGACAAG
GGCTTGAGTGGATGGGATGGATCAGCGCTTACAATGGTAACACAAACTATGCACAGAAGCTCCAGG
GCAGAGTCACCATGACCACAGACACATCCACGAGCACAGCCTACATGGAGCTGAGGAGCCTGAGAT
CTGACGACACGGCCGTGTATTACTGTGCGAGATCCTACAATGGCTTTGACTACTGGGGCCAGGGAA
CCCTGGTCACCGTCTCAAGCGCCTCCACCAAGGGCCCATCGGTCTTCCCCCTGGCACCCTCCTCCA
AGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTCCACACCTTCCCGGCTGTCCTACAGTCC
TCAGGACTCTACTCCCTCAGCAGCGTAGTGACCGTGCCCTCCAGCAGCTTGGGCACCCAGACCTAC
ATCTGCAACGTGAATCACAAGCCCAGCAACACCAAGGTGGACAAGAAAGTTGAGCCCAAATCTTGTG
CGGCCGCACATCATCATCACCATCACGGGGCCGCAGAACAAAAACTCATCTCAGAAGAGGATCTGA
ATGGGGCCGCATAG

PMS211 VL (Fab4 VL) (SEQ ID NO:28):

GTGAAAAAATTATTATTCGCAATTCCTTTAGTTGTTCCTTTCTATTCTCACAGTGCACTTTCCTATGAG
CTGACTCAGCCACCCTCAGTGTCCGTGTCCCCAGGACAGACAGCCAGGATCACCTGCTCTGGATAT
AAATTGGGGGATAAATATGCTTTCTGGTATCAGCAGAAGCCAGGCCAGTCCCCTGTTCTGGTCATTT
ATCAAGATACTAAGCGGCCCTCAGGGATCCCTGAGCGATTCTCTGGCTCCAACTCTGGTAACACAG
CCACTCTGACCATCAGCAGGGTCGAAGCCGGGGATGAGGCCGACTATTACTGT**CAGGTGTGGGATA
GTAGTAGTGATCATGTGGTA**TTCGGCGGAGGGACCAAGCTGACCGTCCTAGGTCAGCCCAAGGCT
GCCCCCTCGGTCACTCTGTTCCCGCCCTCCTCTGAGGAGCTTCAAGCCAACAAGGCCACACTGGTG
TGTCTCATAAGTGACTTCTACCCGGGAGCCGTGACAGTGGCCTGGAAGGCAGATAGCAGCCCCGTC
AAGGCGGGAGTGGAGACCACCACACCCTCCAAACAAAGCAACAACAAGTACGCGGCCAGCAGCTAT
CTGAGCCTGACGCCTGAGCAGTGGAAGTCCCACAGAAGCTACAGCTGCCAGGTCACGCATGAAGG
GAGCACCGTGGAGAAGACAGTGGCCCCTACAGAATGTTCATAA

FIG. 3D

PMS212 VH (Fab5 VH) (SEQ ID NO:31):

ATGAAATACCTATTGCCTACGGCAGCCGCTGGATTGTTATTACTCGCGGCCCAGCCGGCCATGGCC
GAGGTCCAGCTGGTGCAGTCTGGGGGAGGCGTGGTCCAGCCTGGGACGTCCCTGAGACTCTCCTG
TACAGCGTCTGGATTTATCTTCAGTAATTTTGGCATGCACTGGGTCCGCCAGGCTCCAGGCAAGGG
GCTGGAATGGGTGGCTGTTATATGGCATGATGGAAGTAATAAAAACTATGCAGACTCCGTGAAGGG
CCGATTCACCATCTCCAGAGACAATTCCAAGAACACGCTGTATCTGCAAATGAACAGCCTGAGAGCT
GAGGACACGGCCGTGTATTACTGTGCGAGAGACTTAGTGGGAGGAGGTGCTTTTGATATCTGGGG
CCAAGGGACAATGGTCACCGTCTCAAGCGCCTCCACCAAGGGCCCATCGGTCTTCCCCCTGGCACC
CTCCTCCAAGAGCACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTCCACACCTTCCCGGCTGTC
CTACAGTCCTCAGGACTCTACTCCCTCAGCAGCGTAGTGACCGTGCCCTCCAGCAGCTTGGGCACC
CAGACCTACATCTGCAACGTGAATCACAAGCCCAGCAACACCAAGGTGGACAAGAAAGTTGAGCCC
AAATCTTGTGCGGCCGCACATCATCATCACCATCACGGGGCCGCAGAACAAAAACTCATCTCAGAAG
AGGATCTGAATGGGGCCGCATAG

PMS212 VL (Fab5 VL) (SEQ ID NO:32):

GTGAAAAAATTATTATTCGCAATTCCTTTAGTTGTTCCTTTCTATTCTCACAGTGCACAGGCTGTGGTG
ATCCAGGAGCCATCGTTCTCAGTGTCCCCTGGAGGGACAGTCACACTCACTTGTGGCTTGAGC**TCT
GGCTCAGTCTCTACTAGTTACTAC**CCCAGCTGGTACCAGCAGACCCCAGGCCAGGCTCCACGCACG
CTCATCTACAGCACAAACACTCGCTCTTCTGGGGTCCCTGATCGCTTCTCTGGCTCCATCCTTGGGA
ACAAAGCTGCCCTCACCATCACGGGGGCCCAGGCAGATGATGAATCTGATTATTACTGT**GTGCTGTA
TATGGGTAGTGGCATTTGGGTG**TTCGGCGGAGGGACCAAGCTGACCGTCCTAGGTCAGCCCAAGG
CTGCCCCTCGGTCACTCTGTTCCCGCCCTCCTCTGAGGAGCTTCAAGCCAACAAGGCCACACTGG
TGTGTCTCATAAGTGACTTCTACCCGGGAGCCGTGACAGTGGCCTGGAAGGCAGATAGCAGCCCCG
TCAAGGCGGGAGTGGAGACCACCACACCCTCCAAACAAAGCAACAACAAGTATGCGGCCAGCAGCT
ACCTGAGCCTGACGCCTGAGCAGTGGAAGTCCCACAAAAGCTACAGCTGCCAGGTCACGCATGAAG
GGAGCACCGTGGAGAAGACAGTGGCCCCTACAGAATGTTCATAA

FIG. 3E

PMS213 VH (Fab6 VH) (SEQ ID NO:35):

ATGAAATACCTATTGCCTACGGCAGCCGCTGGATTGTTATTACTCGCGGCCCAGCCGGCCATGGCC
CAGGTGCAGCTGGTGCAGTCTGGCCCAGGACTGGTGAAGCCTTCGGAGACCCTGTCCCTCATCTGC
ACTGTCTCT<u>GGTGGCTCCATCAGCAGTAGTAATTACTAC</u>TGGGGCTGGGTCCGCCAGCCCCCAGG
GAAGGGGCTGGAGTGGATTGGGACT<u>ATCTATTATAGTGGGACCACC</u>TACTACAACCCGTCCCTCAA
GAGTCGAGTCACCATATCCGTAGACACGTCCAAGAACCAGTTCTCCCTGGAGCTGAGCTCTGTGAC
CGCCGCAGACACGGCCGTGTATTACTGT<u>GCGAGACTTGGGAGGGGGAGTGCTTTTGATATC</u>TGGG
GCCAAGGGACAATGGTCACCGTCTCAAGCGCCTCCACCAAGGGCCCATCGGTCTTCCCCCTGGCAC
CCTCCTCCAAGAGCACCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTCCACACCTTCCCGGCTGT
CCTACAGTCCTCAGGACTCTACTCCCTCAGCAGCGTAGTGACCGTGCCCTCCAGCAGCTTGGGCAC
CCAGACCTACATCTGCAACGTGAATCACAAGCCCAGCAACACCAAGGTGGACAAGAAAGTTGAGCC
CAAATCTTGTGCGGCCGCACATCATCATCACCATCACGGGGCCGCAGAACAAAAACTCATCTCAGAA
GAGGATCTGAATGGGGCCGCATAG

PMS213 VL (Fab6 VL) (SEQ ID NO:36):

GTGAAAAAATTATTATTCGCAATTCCTTTAGTTGTTCCTTTCTATTCTCACAGTGCACAGTCTGTCGTG
ACGCAGCCGCCCTCACTGTCTGCGGCCCCAGGACAGAGCATCACCATCTCCTGCTCTGGAGGC<u>GG
CTCCAATATTGGGAGAAATTCT</u>GTGTCGTGGCACCGGCAATTCCCGGGAGCAGCCCCGAACTCCT
CGCATTT<u>GACACTTTT</u>AGGCGGCCCTCAGGTGTTCCTGACCGATTCTCTGGTTCCAAGTCTGGCTCG
TCGGCCACCCTGGTCATCACCGGACTCCAGACTGGGGACGAGGCCGACTATTACTGT<u>GGAACTTGG
GATAATTCACTGGATTCTGGAGTC</u>TTCGGCGGAGGGACCAAGGTGACCGTCCTACGTCAGCCCAAG
GCTGCCCCCTCGGTCACTCTATTCCCGCCCTCCTCTGAGGAGCTTCAAGCCAACAAGGCCACACTG
GTGTGTCTCATAAGTGACTTCTACCCGGGAGCCGTGACAGTGGCCTGGAAGGCAGATAGCAGCCCC
GTCAAGGCGAGAGTGGAGACCACCACACCCTCCAAACAAAGCAACAACAAGTACGCGGCCAGCAGC
TACCTGAGCCTGACGCCTGAGCAGTGGAAGTCCCACAAAAGCTACAGCTGCCAGGTCACGCATGAA
GGGAGCACCGTGGAGAAGACAGTGGCCCCTACAGAATGTTCATAA

FIG. 3F

PMS209 VH (full Fab2) (SEQ ID NO:21):

MKYLLPTAAAGLLLLAAQPAMAQVQLQESGPGLVKPSETLSLTCTVS<u>GGSISSSSYY</u>WGWIRQPPGKGL
EWIGS<u>IYYSGST</u>YYNPSLKSRVTISVDTSKNQFSLKLSSVTAADTAVYYC<u>ARLRRYDSSGFFFDY</u>WGQGT
LVTVSSASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCAAAHHHHHHGAAEQKLISEEDLNGAA*

PMS209 VL (full Fab2) (SEQ ID NO:22):

VKKLLFAIPLVVPFYSHSAQSVVTQPPSVSAAPGQKVTISCSGS<u>SSNIGNNY</u>VSWHQQLPGTAPKLLIY<u>DN
DRR</u>PSGIPDRFSGSKSGTSATLAITGLQTGDEADYYC<u>GTWDSSLSGGV</u>FGGGTKVTVLSQPKAAPSVTL
FPPSSEELQANKATLVCLISDFYPGAVTVAWKADSSPVKAGVETTTPSKQSNNKYAASSYLSLTPEQWKS
HKSYSCQVTHEGSSVEKTVAPAECS*

FIG. 3G

PMS210 VH (full Fab3) (SEQ ID NO:25):

MKYLLPTAAAGLLLLAAQPAMAQVQLVQSGGGLVQPGRSLRLSCAAS<u>GFTFSNYA</u>MSWVRQAPGKGLE
WVSAI<u>SGSGGST</u>YYADSVKGRFTISRDSSKNTLYLQMNDLRAEDTAIYYC<u>ARSFTLDY</u>WGQGTLVTVSS
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCAAAHHHHHHGAAEQKLISEEDLNGAA*

PMS210 VL (full Fab3) (SEQ ID NO:26):

VKKLLFAIPLVVPFYSHSALYYVLTQPPSVSKGLRQTATLTCTGN<u>SNNIGNQG</u>AAWLQQHQGHPPKLLSY
<u>RNN</u>NRPSGISERLSASRSGNTASLTITGLQPEDEADYYC<u>SSWDSSLKVQV</u>FGGGTKLTVLGQPKAAPSV
TLFPPSSEELQANKATLVCLISDFYPGAVTVAWKADSSPVKAGVETTTPSKQSNNKYAASSYLSLTPEQW
KSHKSYSCQVTHEGSTVEKTVAPTECS*

FIG. 3H

PMS211 VH (full Fab4) (SEQ ID NO:29):

MKYLLPTAAAGLLLLAAQPAMAQVQLVQSGAEVKKPGSSVKVSCKAS<u>GGTFSSYA</u>ISWVRQAPGQGLE
WMGW<u>ISAYNGNT</u>NYAQKLQGRVTMTTDTSTSTAYMELRSLRSDDTAVYYC<u>ARSYNGFDY</u>WGQGTLVT
VSSASTKGPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCAAAHHHHHHGAAEQKLISEEDLNGAA*

PMS211 VL (full Fab4) (SEQ ID NO:30):

VKKLLFAIPLVVPFYSHSALSYELTQPPSVSVSPGQTARITCSGY<u>KLGDKY</u>AFWYQQKPGQSPVLVIY<u>QD
TK</u>RPSGIPERFSGSNSGNTATLTISRVEAGDEADYYC<u>QVWDSSSDHVV</u>FGGGTKLTVLGQPKAAPSVTL
FPPSSEELQANKATLVCLISDFYPGAVTVAWKADSSPVKAGVETTTPSKQSNNKYAASSYLSLTPEQWKS
HRSYSCQVTHEGSTVEKTVAPTECS*

FIG. 3I

PMS212 VH (full Fab5) (SEQ ID NO:33):

MKYLLPTAAAGLLLLAAQPAMAEVQLVQSGGGVVQPGTSLRLSCTAS<u>GFIFSNFG</u>MHWVRQAPGKGLE
WVAV<u>IWHDGSNK</u>NYADSVKGRFTISRDNSKNTLYLQMNSLRAEDTAVYYC<u>ARDLVGGGAFDI</u>WGQGTM
VTVSSASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCAAAHHHHHHGAAEQKLISEEDLNGAA*

PMS212 VL (full Fab5) (SEQ ID NO:34):

VKKLLFAIPLVVPFYSHSAQAVVIQEPSFSVSPGGTVTLTCGLS<u>SGSVSTSYY</u>PSWYQQTPGQAPRTLIY<u>S
TN</u>TRSSGVPDRFSGSILGNKAALTITGAQADDESDYYC<u>VLYMGSGIWV</u>FGGGTKLTVLGQPKAAPSVTLF
PPSSEELQANKATLVCLISDFYPGAVTVAWKADSSPVKAGVETTTPSKQSNNKYAASSYLSLTPEQWKS
HKSYSCQVTHEGSTVEKTVAPTECS*

FIG. 3J

PMS213 VH (full Fab6) (SEQ ID NO:37):

MKYLLPTAAAGLLLLAAQPAMAQVQLVQSGPGLVKPSETLSLICTVS<u>GGSISSSNYY</u>WGWVRQPPGKGL
EWIGT<u>IYYSGTT</u>YYNPSLKSRVTISVDTSKNQFSLELSSVTAADTAVYYC<u>ARLGRGSAFDI</u>WGQGTMVTV
SSASTKGPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCAAAHHHHHHGAAEQKLISEEDLNGAA*

PMS213 VL (full Fab6) (SEQ ID NO:38):

VKKLLFAIPLVVPFYSHSAQSVVTQPPSLSAAPGQSITISCSGG<u>GSNIGRNS</u>VSWHRQFPGAAPELLAF<u>DT
F</u>RRPSGVPDRFSGSKSGSSATLVITGLQTGDEADYYC<u>GTWDNSLDSGV</u>FGGGTKVTVLRQPKAAPSVTL
FPPSSEELQANKATLVCLISDFYPGAVTVAWKADSSPVKARVETTTPSKQSNNKYAASSYLSLTPEQWKS
HKSYSCQVTHEGSTVEKTVAPTECS*

FIG. 4A

PMS210-Fc (SEQ ID NO:41):

ATGAAACATCTGTGGTTCTTCCTTCTCCTGGTGGCAGCGGCCCAGCCGGCCCAGGTGCAGCTGGTG
CAGTCTGGGGGAGGCTTGGTACAGCCTGGGAGGTCCCTGCGACTCTCCTGTGCAGCCTCT**GGATTC
ACCTTTAGCAACTATGCC**ATGAGCTGGGTCCGCCAGGCTCCAGGGAAGGGGCTGGAGTGGGTCTC
AGCTATTAGTGGTAGTGGTGGTAGCACATACTACGCAGACTCCGTGAAGGGCCGGTTCACCATCTC
CAGAGACAGTTCCAAGAACACGCTTTATCTTCAAATGAACGACCTGAGAGCCGAGGACACGGCTATA
TATTACTGTGCGAGAAGTTTCACTCTTGACTATTGGGGCCAGGGAACCCTGGTCACCGTCTCAAGC
GCCTCCACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAACTCAGG
CGCCCTGACCAGCGGCGTCCACACCTTCCCGGCTGTCCTACAGTCCTCAGGACTCTACTCCCTCAG
CAGCGTAGTGACCGTGCCCTCCAGCAGCTTGGGCACCCAGACCTACATCTGCAACGTGAATCACAA
GCCCAGCAACACCAAGGTGGACAAGAAAGTTGAGCCCAAATCTTGTGGTGGCGGCGGTTCCGGAG
GTGGTGGTTCTGGCGGTGGTGGCAGCCTTTACTATGTGCTGACTCAGCCACCCTCGGTGTCCAAGG
GCTTGAGACAGACCGCCACACTCACCTGCACTGGGAACAGCAACAATATTGGCAACCAAGGAGCA
GCTTGGCTGCAGCAGCACCAGGGCCACCCTCCCAAACTCCTATCCTACAGGAATAACAACCGGCCC
TCAGGGATCTCAGAGAGATTATCTGCATCCAGGTCAGGAAATACTGCCTCCCTGACCATTACTGGAC
TCCAGCCTGAGGACGAGGCTGACTATTACTGCTCATCATGGGACAGCAGTCTGAAAGTTCAGGTGT
TCGGCGGAGGGACCAAGCTGACCGTCCTAGGTCAGCCCAAGGCTGCCCCTCGGTCACTCTGTTC
CCACCCTCCTCTGAGGAGCTTCAAGCCAACAAGGCCACACTGGTGTGTCTCATAAGTGACTTCTACC
CGGGAGCCGTGACAGTGGCCTGGAAGGCAGATAGCAGCCCCGTCAAGGCGGGAGTGGAGACCAC
CACACCCTCCAAACAAAGCAACAACAAGTACGCGGCCAGCAGCTACCTGAGCCTGACGCCTGAGCA
GTGGAAGTCCCACAAAAGCTACAGCTGCCAGGTCACGCATGAAGGGAGCACCGTGGAGAAGACAGT
GGCCCCTACAGAATGTTCAGCGGCCGCAGAGCCCAAATCTTGTGACAAAACTCACACATGCCCACC
GTGCCCAGCACCTGAACTCCTGGGGGGACCGTCAGTCTTCCTCTTCCCCCCAAAACCCAAGGACAC
CCTCATGATCTCCCGGACCCCTGAGGTCACATGCGTGGTGGTGGACGTGAGCCACGAAGACCCTGA
GGTCAAGTTCAACTGGTACGTGGACGGCGTGGAGGTGCATAATGCCAAGACAAAGCCGCGGGAGG
AGCAGTACAACAGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCATCGAGAAAACCATCTCCA
AAGCCAAAGGGCAGCCCCGAGAACCACAGGTGTACACCCTGCCCCCATCCCGGGATGAGCTGACC
AAGAACCAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGACGGCTC
CTTCTTCCTCTACAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTGTCTCCGGGTAA
ATGA

FIG. 4B

PMS212-Fc (SEQ ID NO:43):

ATGAAACATCTGTGGTTCTTCCTTCTCCTGGTGGCAGCGGCCCAGCCGGCCGAGGTCCAGCTGGTG
CAGTCTGGGGGAGGCGTGGTCCAGCCTGGGACGTCCCTGAGACTCTCCTGTACAGCGTCT<u>GGATTT
ATCTTCAGTAATTTTGGC</u>ATGCACTGGGTCCGCCAGGCTCCAGGCAAGGGGCTGGAATGGGTGGCT
GTT<u>ATATGGCATGATGGAAGTAATAAA</u>AACTATGCAGACTCCGTGAAGGGCCGATTCACCATCTCC
AGAGACAATTCCAAGAACACGCTGTATCTGCAAATGAACAGCCTGAGAGCTGAGGACACGGCCGTG
TATTACTGT<u>GCGAGAGACTTAGTGGGAGGAGGTGCTTTTGATATC</u>TGGGGCCAAGGGACAATGGTC
ACCGTCTCAAGCGCCTCCACCAAGGGCCCATCGGTCTTCCCCCTGGCACCCTCCTCCAAGAGCACC
TCTGGGGGCACAGCGGCCCTGGGCTGCCTGGTCAAGGACTACTTCCCCGAACCGGTGACGGTGTC
GTGGAACTCAGGCGCCCTGACCAGCGGCGTCCACACCTTCCCGGCTGTCCTACAGTCCTCAGGACT
CTACTCCCTCAGCAGCGTAGTGACCGTGCCCTCCAGCAGCTTGGGCACCCAGACCTACATCTGCAA
CGTGAATCACAAGCCCAGCAACACCAAGGTGGACAAGAAAGTTGAGCCCAAATCTTGTGGTGGCGG
CGGTTCCGGAGGTGGTGGTTCTGGCGGTGGTGGCAGCCAGGCTGTGGTGATCCAGGAGCCATCGT
TCTCAGTGTCCCTGGAGGGACAGTCACACTCACTTGTGGCTTGAGC<u>TCTGGCTCAGTCTCTACTAG
TTACTAC</u>CCCAGCTGGTACCAGCAGACCCCAGGCCAGGCTCCACGCACGCTCATCTAC<u>AGCACAAA
C</u>ACTCGCTCTTCTGGGGTCCCTGATCGCTTCTCTGGCTCCATCCTTGGGAACAAAGCTGCCCTCACC
ATCACGGGGGCCCAGGCAGATGATGAATCTGATTATTACTGT<u>GTGCTGTATATGGGTAGTGGCATTT
GGGTG</u>TTCGGCGGAGGGACCAAGCTGACCGTCCTAGGTCAGCCCAAGGCTGCCCCCTCGGTCACT
CTGTTCCCGCCCTCCTCTGAGGAGCTTCAAGCCAACAAGGCCACACTGGTGTGTCTCATAAGTGACT
TCTACCCGGGAGCCGTGACAGTGGCCTGGAAGGCAGATAGCAGCCCCGTCAAGGCGGGAGTGGAG
ACCACCACACCCTCCAAACAAAGCAACAACAAGTATGCGGCCAGCAGCTACCTGAGCCTGACGCCT
GAGCAGTGGAAGTCCCACAAAAGCTACAGCTGCCAGGTCACGCATGAAGGGAGCACCGTGGAGAA
GACAGTGGCCCCTACAGAATGTTCAGCGGCCGCAGAGCCCAAATCTTGTGACAAAACTCACACATG
CCCACCGTGCCCAGCACCTGAACTCCTGGGGGGACCGTCAGTCTTCCTCTTCCCCCCAAAACCCAA
GGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGC
GGGAGGAGCAGTACAACAGCACGTACCGTGTGGTCAGCGTCCTCACCGTCCTGCACCAGGACTGG
CTGAATGGCAAGGAGTACAAGTGCAAGGTCTCCAACAAAGCCCTCCCAGCCCCCATCGAGAAAACC
ATCTCCAAAGCCAAAGGGCAGCCCCGAGAACCACAGGTGTACACCCTGCCCCCATCCCGGGATGAG
CTGACCAAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGACTCCGA
CGGCTCCTTCTTCCTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCCTCTCCCTGTCTCC
GGGTAAATGA

FIG. 4C

PMS210-Fc (SEQ ID NO:42):

MKHLWFFLLLVAAAQPAQVQLVQSGGGLVQPGRSLRLSCAAS<u>GFTFSNYA</u>MSWVRQAPGKGLEWVSA<u>I
SGSGGST</u>YYADSVKGRFTISRDSSKNTLYLQMNDLRAEDTAIYYC<u>ARSFTLDY</u>WGQGTLVTVSSASTKG
PSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCGGGGSGGGGSGGGGSLYYVLTQPPSVSKGLRQTATLTCTG
<u>NSNNIGNQG</u>AAWLQQHQGHPPKLLSY<u>RNN</u>NRPSGISERLSASRSGNTASLTITGLQPEDEADYYC<u>SSWD
SSLKVQV</u>FGGGTKLTVLGQPKAAPSVTLFPPSSEELQANKATLVCLISDFYPGAVTVAWKADSSPVKAGV
ETTTPSKQSNNKYAASSYLSLTPEQWKSHKSYSCQVTHEGSTVEKTVAPTECSAAAEPKSCDKTHTCPP
CPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRWQQGNVFSCSVMHEALHNH
YTQKSLSLSPGK*

FIG. 4D

PMS212-Fc (SEQ ID NO:44):

MKHLWFFLLLVAAAQPAEVQLVQSGGGVVQPGTSLRLSCTAS<u>GFIFSNFG</u>MHWVRQAPGKGLEWVAV<u>I
WHDGSNK</u>NYADSVKGRFTISRDNSKNTLYLQMNSLRAEDTAVYYC<u>ARDLVGGGAFDI</u>WGQGTMVTVSS
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCGGGGSGGGGSGGGGSQAVVIQEPSFSVSPGGTVTL
TCGLS<u>SGSVSTSYY</u>PSWYQQTPGQAPRTLIY<u>STN</u>TRSSGVPDRFSGSILGNKAALTITGAQADDESDYYC
<u>VLYMGSGIWV</u>FGGGTKLTVLGQPKAAPSVTLFPPSSEELQANKATLVCLISDFYPGAVTVAWKADSSPVK
AGVETTTPSKQSNNKYAASSYLSLTPEQWKSHKSYSCQVTHEGSTVEKTVAPTECSAAAEPKSCDKTHT
CPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCSVMHEALH
NHYTQKSLSLSPGK*

| alpha synuclein (state) | ka (1/Ms) | kd (1/s) | KD (M) | KD (nM) |
|---|---|---|---|---|
| PFF | 1.491E+6 | 0.001006 | 6.748E-10 | 0.67nM |
| Oligomer | 1.595E+5 | 5.517E-4 | 3.459E-9 | 3.46nM |

- PD — Brain extracts from PD patients
- PFF — recombinant human PFF (P.C)
- CSF — From PD/DLB patients
- PBS — (N.C)

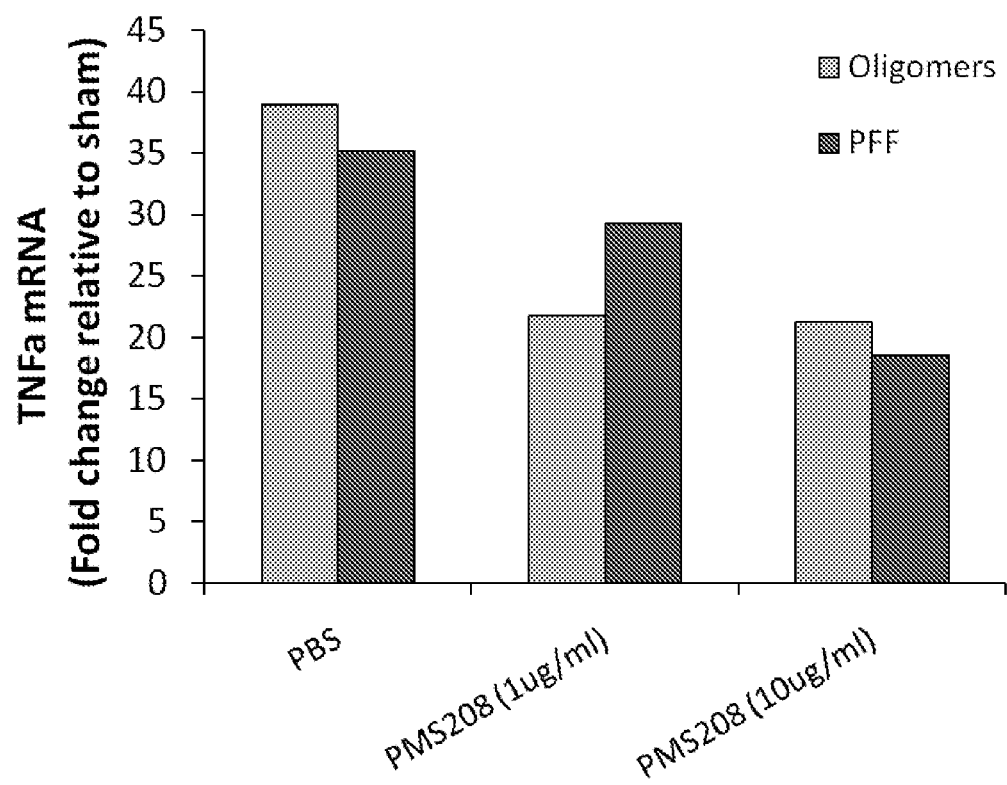

SEQUENCE LISTING

```
<160> NUMBER OF SEQ ID NOS: 54

<210> SEQ ID NO 1
<211> LENGTH: 8
<212> TYPE: PRT
<213> ORGANISM: Artificial Sequence
<220> FEATURE:
<223> OTHER INFORMATION: CDR H1

<400> SEQUENCE: 1

Gly Gly Ser Ile Ser Ser His Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: CDR H2

<400> SEQUENCE: 2

Ile Tyr Asp Ser Gly Ser Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CDR H3

<400> SEQUENCE: 3

Ala Arg Gly Ala Gly Trp Tyr Arg Phe
1               5

<210> SEQ ID NO 4
<211> LENGTH: 12
<212> TYPE: PRT
<213> ORGANISM: Artificial Sequence
<220> FEATURE:
<223> OTHER INFORMATION: CDR2 L1

<400> SEQUENCE: 4

Gln Ser Val Leu Tyr Ser Ser Asn Asn Lys Asn Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: CDR2 L2

<400> SEQUENCE: 5

Trp Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: CDR3 L3

<400> SEQUENCE: 6

Gln Gln Tyr Tyr Ser Thr Pro Arg Thr
1               5
```

<210> SEQ ID NO 7
<211> LENGTH: 24
<212> TYPE: DNA
<213> ORGANISM: Artificial Sequence
<220> FEATURE:
<223> OTHER INFORMATION: CDR1 HC

<400> SEQUENCE: 7
ggcggctcta tcagcagcca ctac                                              24

<210> SEQ ID NO 8
<211> LENGTH: 21
<212> TYPE: DNA
<213> ORGANISM: Artificial Sequence
<220> FEATURE:
<223> OTHER INFORMATION: CDR2 HC

<400> SEQUENCE: 8
atctacgaca gcggcagcac c                                                 21

<210> SEQ ID NO 9
<211> LENGTH: 27
<212> TYPE: DNA
<213> ORGANISM: Artificial Sequence
<220> FEATURE:
<223> OTHER INFORMATION: CDR3 HC

<400> SEQUENCE: 9
gctagaggcg ccggatggta cagattt                                           27

<210> SEQ ID NO 10
<211> LENGTH: 36
<212> TYPE: DNA
<213> ORGANISM: Artificial Sequence
<220> FEATURE:
<223> OTHER INFORMATION: CDR1 LC

<400> SEQUENCE: 10
cagagcgtgc tgtactccag caacaacaag aactac                                 36

<210> SEQ ID NO 11
<211> LENGTH: 9
<212> TYPE: DNA
<213> ORGANISM: Artificial Sequence
<220> FEATURE:
<223> OTHER INFORMATION: CDR2 LC

<400> SEQUENCE: 11 tgggccagc                                                                9

<210> SEQ ID NO 12
<211> LENGTH: 27
<212> TYPE: DNA
<213> ORGANISM: Artificial Sequence
<220> FEATURE:
<223> OTHER INFORMATION: CDR3 LC

<400> SEQUENCE: 12
cagcagtact acagcacccc tcggacc                                           27

<210> SEQ ID NO 13
<211> LENGTH: 140
<212> TYPE: PRT
<213> ORGANISM: Homo sapiens

```
<400> SEQUENCE: 13

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 14
<211> LENGTH: 17
<212> TYPE: PRT
<213> ORGANISM: Artificial Sequence
<220> FEATURE:
<223> OTHER INFORMATION: leader sequence

<400> SEQUENCE: 14

Met Lys His Leu Trp Phe Phe Leu Leu Leu Val Ala Ala Ala Gln Pro
1               5                   10                  15

Ala

<210> SEQ ID NO 15
<211> LENGTH: 45
<212> TYPE: DNA
<213> ORGANISM: Artificial Sequence
<220> FEATURE:
<223> OTHER INFORMATION: linker

<400> SEQUENCE: 15
ggtggcggcg gttccggagg tggtggttct ggcggtggtg gcagc              45

<210> SEQ ID NO 16
<211> LENGTH: 46
<212> TYPE: DNA
<213> ORGANISM: Artificial Sequence
<220> FEATURE:
<223> OTHER INFORMATION: leader sequence

<400> SEQUENCE: 16
atgaaacatc tgtggttctt ccttctcctg gtggcagcgg cccagc             46

<210> SEQ ID NO 17
<211> LENGTH: 10
<212> TYPE: PRT
<213> ORGANISM: Artificial Sequence
<220> FEATURE:
<223> OTHER INFORMATION: myc-tag

<400> SEQUENCE: 17

Glu Gln Lys Leu Ile Ser Glu Glu Asp Leu
```

<210> SEQ ID NO 18
<211> LENGTH: 6
<212> TYPE: PRT
<213> ORGANISM: Artificial Sequence
<220> FEATURE:
<223> OTHER INFORMATION: 6xHis-tag

<400> SEQUENCE: 18

His His His His His His
1               5

<210> SEQ ID NO 19
<211> LENGTH: 825
<212> TYPE: DNA
<213> ORGANISM: Artificial Sequence
<220> FEATURE:
<223> OTHER INFORMATION: PMS209 VH

<400> SEQUENCE: 19

| | | | | | |
|---|---|---|---|---|---|
| atgaaatacc | tattgcctac | ggcagccgct | ggattgttat | tactcgcggc | ccagccggcc | 60 |
| atggcccagg | tgcagctgca | ggagtcgggc | ccaggactgg | tgaagccctc | ggagaccctg | 120 |
| tccctcacct | gcactgtctc | tggtggctcc | atcagcagta | gtagttacta | ctggggctgg | 180 |
| atccgccagc | ccccagggaa | ggggctggag | tggattggga | gtatctatta | tagtgggagc | 240 |
| acctactaca | acccgtccct | caagagtcga | gtcaccatat | ccgtagacac | gtccaagaac | 300 |
| cagttctccc | tgaagctgag | ctctgtgacc | gccgcagaca | cggctgtgta | ttactgtgcg | 360 |
| agactccgtc | gctatgatag | tagtggtttt | ttctttgact | actggggcca | gggaaccctg | 420 |
| gtcaccgtct | caagcgcctc | caccaagggc | ccatcggtct | tccccctggc | accctcctcc | 480 |
| aagagcacct | ctgggggcac | agcggccctg | ggctgcctgg | tcaaggacta | cttccccgaa | 540 |
| ccggtgacgg | tgtcgtggaa | ctcaggcgcc | ctgaccagcg | gcgtccacac | cttcccggct | 600 |
| gtcctacagt | cctcaggact | ctactccctc | agcagcgtag | tgaccgtgcc | ctccagcagc | 660 |
| ttgggcaccc | agacctacat | ctgcaacgtg | aatcacaagc | ccagcaacac | caaggtggac | 720 |
| aagaaagttg | agcccaaatc | ttgtgcggcc | gcacatcatc | atcaccatca | cggggccgca | 780 |
| gaacaaaaac | tcatctcaga | agaggatctg | aatggggccg | catag | | 825 |

<210> SEQ ID NO 20
<211> LENGTH: 708
<212> TYPE: DNA
<213> ORGANISM: Artificial Sequence
<220> FEATURE:
<223> OTHER INFORMATION: PMS209 VL

<400> SEQUENCE: 20

| | | | | | |
|---|---|---|---|---|---|
| gtgaaaaaat | tattattcgc | aattcctta | gttgttcctt | tctattctca | cagtgcacag | 60 |
| tctgtcgtga | cgcagccgcc | ctcagtgtct | gcggccccag | gacagaaggt | caccatctcc | 120 |
| tgctctggaa | gcagctccaa | cattgggaat | aattatgtat | cctggcatca | gcagctccca | 180 |
| ggaacagccc | ccaaactcct | catttatgac | aatgataggc | gaccctcagg | gattcctgac | 240 |
| cgattctctg | gctccaagtc | tggcacgtca | gccaccctgg | ccatcaccgg | actccagact | 300 |
| ggggacgagg | ccgactatta | ctgcggaaca | tgggatagca | gcctgagtgg | ggagtgttc | 360 |
| ggcggaggga | ccaaggtgac | cgtcctgagt | cagcccaagg | ctgccccctc | ggtcactctg | 420 |
| ttcccaccct | cctctgagga | gcttcaagcc | aacaaggcca | cactggtgtg | tctcataagt | 480 |

| | | |
|---|---|---|
| gacttctacc cgggagccgt gacagtggcc tggaaggcag atagcagccc cgtcaaggcg | 540 |
| ggagtggaga ccaccacacc ctccaaacaa agcaacaaca agtacgcggc cagcagctac | 600 |
| ctgagcctga cgcctgagca gtggaagtcc cacaaaagct acagctgcca ggtcacgcat | 660 |
| gaagggagct ccgtggagaa gacagtggcc cctgcagaat gctcttaa | 708 |

```
<210> SEQ ID NO 21
<211> LENGTH: 274
<212> TYPE: PRT
<213> ORGANISM: Artificial Sequence
<220> FEATURE:
<223> OTHER INFORMATION: PMS209 VH

<400> SEQUENCE: 21

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Gly Ser Ile Ser Ser Ser Tyr Tyr Trp Gly Trp Ile Arg Gln Pro
    50                  55                  60

Pro Gly Lys Gly Leu Glu Trp Ile Gly Ser Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Leu Arg Arg Tyr Asp Ser Ser
        115                 120                 125

Gly Phe Phe Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Ala Ala His His His His
                245                 250                 255

His Gly Ala Ala Glu Gln Lys Leu Ile Ser Glu Glu Asp Leu Asn Gly
            260                 265                 270

Ala Ala

<210> SEQ ID NO 22
<211> LENGTH: 235
<212> TYPE: PRT
<213> ORGANISM: Artificial Sequence
<220> FEATURE:
<223> OTHER INFORMATION: PMS209 VL
```

<400> SEQUENCE: 22

```
Val Lys Lys Leu Leu Phe Ala Ile Pro Leu Val Val Pro Phe Tyr Ser
1               5                   10                  15

His Ser Ala Gln Ser Val Val Thr Gln Pro Pro Ser Val Ser Ala Ala
            20                  25                  30

Pro Gly Gln Lys Val Thr Ile Ser Cys Ser Gly Ser Ser Ser Asn Ile
        35                  40                  45

Gly Asn Asn Tyr Val Ser Trp His Gln Gln Leu Pro Gly Thr Ala Pro
50                  55                  60

Lys Leu Leu Ile Tyr Asp Asn Asp Arg Arg Pro Ser Gly Ile Pro Asp
65                  70                  75                  80

Arg Phe Ser Gly Ser Lys Ser Gly Thr Ser Ala Thr Leu Ala Ile Thr
                85                  90                  95

Gly Leu Gln Thr Gly Asp Glu Ala Asp Tyr Tyr Cys Gly Thr Trp Asp
            100                 105                 110

Ser Ser Leu Ser Gly Gly Val Phe Gly Gly Gly Thr Lys Val Thr Val
        115                 120                 125

Leu Ser Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Ser
    210                 215                 220

Val Glu Lys Thr Val Ala Pro Ala Glu Cys Ser
225                 230                 235
```

<210> SEQ ID NO 23
<211> LENGTH: 801
<212> TYPE: DNA
<213> ORGANISM: Artificial Sequence
<220> FEATURE:
<223> OTHER INFORMATION: PMS210 VH

<400> SEQUENCE: 23

```
atgaaatacc tattgcctac ggcagccgct ggattgttat tactcgcggc ccagccggcc      60
atggcccagg tgcagctggt gcagtctggg ggaggcttgg tacagcctgg gaggtccctg     120
cgactctcct gtgcagcctc tggattcacc tttagcaact atgccatgag ctgggtccgc     180
caggctccag gaaggggct ggagtgggtc tcagctatta gtggtagtgg tggtagcaca     240
tactacgcag actccgtgaa gggccggttc accatctcca gagacagttc caagaacacg     300
ctttatcttc aaatgaacga cctgagagcc gaggacacgg ctatatatta ctgtgcgaga     360
agtttcactc ttgactattg gggccaggga accctggtca ccgtctcaag cgcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt ccacaccttc ccggctgtcc tacagtcctc aggactctac     600
tccctcagca gcgtagtgac cgtgccctcc agcagcttgg gcacccagac ctacatctgc     660
```

```
aacgtgaatc acaagcccag caacaccaag gtggacaaga agttgagcc caaatcttgt    720 gcggccgcac atcatcatca ccatcacggg gccgcagaac aaaaactcat ctcagaagag    780
gatctgaatg gggccgcata g                                              801
```

<210> SEQ ID NO 24
<211> LENGTH: 711
<212> TYPE: DNA
<213> ORGANISM: Artificial Sequence
<220> FEATURE:
<223> OTHER INFORMATION: PMS210 VL

<400> SEQUENCE: 24

```
gtgaaaaaat tattattcgc aattccttta gttgttcctt tctattctca cagtgcactt     60
tactatgtgc tgactcagcc accctcggtg tccaagggct tgagacagac cgccacactc    120
acctgcactg ggaacagcaa caatattggc aaccaaggag cagcttggct gcagcagcac    180
cagggccacc ctcccaaact cctatcctac aggaataaca ccggccctc agggatctca    240 gagagattat ctgcatccag gtcaggaaat actgcctccc tgaccattac tggactccag    300
cctgaggacg aggctgacta ttactgctca tcatgggaca gcagtctgaa agttcaggtg    360
ttcggcggag ggaccaagct gaccgtccta ggtcagccca aggctgcccc ctcggtcact    420
ctgttcccac cctcctctga ggagcttcaa gccaacaagg ccacactggt gtgtctcata    480
agtgacttct acccgggagc cgtgacagtg gcctggaagg cagatagcag ccccgtcaag    540
gcgggagtgg agaccaccac accctccaaa caaagcaaca acaagtacgc ggccagcagc    600
tacctgagcc tgacgcctga gcagtggaag tcccacaaaa gctacagctg ccaggtcacg    660
catgaaggga gcaccgtgga agacagtgtg cccctacag aatgttcata a              711
```

<210> SEQ ID NO 25
<211> LENGTH: 266
<212> TYPE: PRT
<213> ORGANISM: Artificial Sequence
<220> FEATURE:
<223> OTHER INFORMATION: PMS210 VH

<400> SEQUENCE: 25

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Gly Gly
            20                  25                  30

Leu Val Gln Pro Gly Arg Ser Leu Arg Leu Ser Cys Ala Ala Ser Gly
        35                  40                  45

Phe Thr Phe Ser Asn Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Ser
                85                  90                  95

Ser Lys Asn Thr Leu Tyr Leu Gln Met Asn Asp Leu Arg Ala Glu Asp
            100                 105                 110

Thr Ala Ile Tyr Tyr Cys Ala Arg Ser Phe Thr Leu Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160
```

```
Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Ala Ala Ala His His His His His His Gly Ala Ala Glu Gln Lys Leu
                245                 250                 255

Ile Ser Glu Glu Asp Leu Asn Gly Ala Ala
                260                 265

<210> SEQ ID NO 26
<211> LENGTH: 236
<212> TYPE: PRT
<213> ORGANISM: Artificial Sequence
<220> FEATURE:
<223> OTHER INFORMATION: PMS210 VL

<400> SEQUENCE: 26

Val Lys Lys Leu Leu Phe Ala Ile Pro Leu Val Val Pro Phe Tyr Ser
1               5                   10                  15

His Ser Ala Leu Tyr Tyr Val Leu Thr Gln Pro Pro Ser Val Ser Lys
            20                  25                  30

Gly Leu Arg Gln Thr Ala Thr Leu Thr Cys Thr Gly Asn Ser Asn Asn
        35                  40                  45

Ile Gly Asn Gln Gly Ala Ala Trp Leu Gln Gln His Gln Gly His Pro
    50                  55                  60

Pro Lys Leu Leu Ser Tyr Arg Asn Asn Asn Arg Pro Ser Gly Ile Ser
65                  70                  75                  80

Glu Arg Leu Ser Ala Ser Arg Ser Gly Asn Thr Ala Ser Leu Thr Ile
                85                  90                  95

Thr Gly Leu Gln Pro Glu Asp Glu Ala Asp Tyr Tyr Cys Ser Ser Trp
            100                 105                 110

Asp Ser Ser Leu Lys Val Gln Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Lys Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 27
```

```
<211> LENGTH: 804
<212> TYPE: DNA
<213> ORGANISM: Artificial Sequence
<220> FEATURE:
<223> OTHER INFORMATION: PMS211 VH

<400> SEQUENCE: 27
atgaaatacc tattgcctac ggcagccgct ggattgttat tactcgcggc ccagccggcc    60
atggcccagg tgcagctggt gcagtctggg gctgaggtga agaagcctgg gtcctcggtg   120
aaggtctcct gcaaggcttc tggaggcacc ttcagcagct atgctatcag ctgggtgcga   180
caggcccctg gacaagggct tgagtggatg ggatggatca cgcttacaa tggtaacaca    240
aactatgcac agaagctcca gggcagagtc accatgacca cagacacatc cacgagcaca   300
gcctacatgg agctgaggag cctgagatct gacgacacgg ccgtgtatta ctgtgcgaga   360
tcctacaatg gctttgacta ctggggccag ggaaccctgg tcaccgtctc aagcgcctcc   420
accaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtccacacc ttcccggctg tcctacagtc ctcaggactc   600
tactccctca gcagcgtagt gaccgtgccc tccagcagct gggcaccca gacctacatc    660
tgcaacgtga atcacaagcc cagcaacacc aaggtggaca gaaagttga gcccaaatct    720
tgtgcggccg cacatcatca tcaccatcac ggggccgcag aacaaaaact catctcagaa   780
gaggatctga tggggccgc atag                                           804

<210> SEQ ID NO 28
<211> LENGTH: 705
<212> TYPE: DNA
<213> ORGANISM: Artificial Sequence
<220> FEATURE:
<223> OTHER INFORMATION: PMS211 VL

<400> SEQUENCE: 28
gtgaaaaaat tattattcgc aattcctta gttgttcctt tctattctca cagtgcactt    60
tcctatgagc tgactcagcc accctcagtg tccgtgtccc caggacagac agccaggatc   120
acctgctctg gatataaatt gggggataaa tatgctttct ggtatcagca aagccaggc    180
cagtccctg ttctggtcat ttatcaagat actaagcggc cctcaggat ccctgagcga    240
ttctctggct ccaactctgg taacacagcc actctgacca tcagcagggt cgaagccggg   300
gatgaggccg actattactg tcaggtgtgg gatagtagta gtgatcatgt ggtattcggc   360
ggagggacca agctgaccgt cctaggtcag cccaaggctg ccccctcggt cactctgttc   420
ccgccctcct ctgaggagct tcaagccaac aaggccacac tggtgtgtct cataagtgac   480
ttctacccgg gagccgtgac agtggcctgg aaggcagata gcagcccgt caaggcggga   540
gtggagacca ccacacctc caacaaagc aacaacaagt acgcggccag cagctatctg     600
agcctgacgc ctgagcagtg gaagtcccac agaagctaca ctgccaggt cacgcatgaa    660
gggagcaccg tggagaagac agtggcccct acagaatgtt cataa                  705

<210> SEQ ID NO 29
<211> LENGTH: 267
<212> TYPE: PRT
<213> ORGANISM: Artificial Sequence
<220> FEATURE:
<223> OTHER INFORMATION: PMS211 VH

<400> SEQUENCE: 29
```

Met Lys Tyr Leu Leu Pro Thr Ala Ala Ala Gly Leu Leu Leu Ala
1               5                   10                  15

Ala Gln Pro Ala Met Ala Gln Val Gln Leu Val Gln Ser Gly Ala Glu
                20                  25                  30

Val Lys Lys Pro Gly Ser Ser Val Lys Val Ser Cys Lys Ala Ser Gly
            35                  40                  45

Gly Thr Phe Ser Ser Tyr Ala Ile Ser Trp Val Arg Gln Ala Pro Gly
        50                  55                  60

Gln Gly Leu Glu Trp Met Gly Trp Ile Ser Ala Tyr Asn Gly Asn Thr
65                  70                  75                  80

Asn Tyr Ala Gln Lys Leu Gln Gly Arg Val Thr Met Thr Thr Asp Thr
                85                  90                  95

Ser Thr Ser Thr Ala Tyr Met Glu Leu Arg Ser Leu Arg Ser Asp Asp
            100                 105                 110

Thr Ala Val Tyr Tyr Cys Ala Arg Ser Tyr Asn Gly Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Ala Ala Ala His His His His His His Gly Ala Ala Glu Gln Lys
                245                 250                 255

Leu Ile Ser Glu Glu Asp Leu Asn Gly Ala Ala
            260                 265

<210> SEQ ID NO 30
<211> LENGTH: 234
<212> TYPE: PRT
<213> ORGANISM: Artificial Sequence
<220> FEATURE:
<223> OTHER INFORMATION: PMS211 VL

<400> SEQUENCE: 30

Val Lys Lys Leu Leu Phe Ala Ile Pro Leu Val Val Pro Phe Tyr Ser
1               5                   10                  15

His Ser Ala Leu Ser Tyr Glu Leu Thr Gln Pro Pro Ser Val Ser Val
                20                  25                  30

Ser Pro Gly Gln Thr Ala Arg Ile Thr Cys Ser Gly Tyr Lys Leu Gly
            35                  40                  45

Asp Lys Tyr Ala Phe Trp Tyr Gln Gln Lys Pro Gly Gln Ser Pro Val
        50                  55                  60

Leu Val Ile Tyr Gln Asp Thr Lys Arg Pro Ser Gly Ile Pro Glu Arg
65                  70                  75                  80

Phe Ser Gly Ser Asn Ser Gly Asn Thr Ala Thr Leu Thr Ile Ser Arg
                85                  90                  95

Val Glu Ala Gly Asp Glu Ala Asp Tyr Tyr Cys Gln Val Trp Asp Ser
              100                 105                 110

Ser Ser Asp His Val Val Phe Gly Gly Gly Thr Lys Leu Thr Val Leu
          115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
              165                 170                 175

Val Lys Ala Gly Val Glu Thr Thr Thr Pro Ser Lys Gln Ser Asn Asn
          180                 185                 190

Lys Tyr Ala Ala Ser Ser Tyr Leu Ser Leu Thr Pro Glu Gln Trp Lys
      195                 200                 205

Ser His Arg Ser Tyr Ser Cys Gln Val Thr His Glu Gly Ser Thr Val
  210                 215                 220

Glu Lys Thr Val Ala Pro Thr Glu Cys Ser
225                 230

<210> SEQ ID NO 31
<211> LENGTH: 813
<212> TYPE: DNA
<213> ORGANISM: Artificial Sequence
<220> FEATURE:
<223> OTHER INFORMATION: PMS212 VH

<400> SEQUENCE: 31
atgaaatacc tattgcctac ggcagccgct ggattgttat tactcgcggc ccagccggcc      60
atggccgagg tccagctggt gcagtctggg ggaggcgtgg tccagcctgg gacgtccctg     120
agactctcct gtacagcgtc tggatttatc ttcagtaatt ttggcatgca ctgggtccgc     180
caggctccag gcaaggggct ggaatgggtg gctgttatat ggcatgatgg aagtaataaa     240
aactatgcag actccgtgaa ggccgattca ccatctcca gagacaattc aagaacacg      300 ctgtatctgc aaatgaacag cctgagagct gaggacacgg ccgtgtatta ctgtgcgaga     360
gacttagtgg aggaggtgc ttttgatatc tggggccaag gacaatggt caccgtctca      420 agcgcctcca ccaagggccc atcggtcttc cccctggcac cctcctccaa gagcacctct     480
gggggcacag cggccctggg ctgcctggtc aaggactact ccccgaaccc ggtgacggtg     540
tcgtggaact caggcgccct gaccagcggc gtccacacct tcccggctgt cctacagtcc     600
tcaggactct actccctcag cagcgtagtg accgtgccct ccagcagctt gggcacccag     660
acctacatct gcaacgtgaa tcacaagccc agcaacacca aggtggacaa gaaagttgag     720
cccaaatctt gtgcggccgc acatcatcat caccatcacg gggccgcaga acaaaaactc     780
atctcagaag aggatctgaa tggggccgca tag                                 813

<210> SEQ ID NO 32
<211> LENGTH: 708
<212> TYPE: DNA
<213> ORGANISM: Artificial Sequence
<220> FEATURE:
<223> OTHER INFORMATION: PMS212 VL

<400> SEQUENCE: 32
gtgaaaaaat tattattcgc aattcccttta gttgttcctt tctattctca cagtgcacag      60
gctgtggtga tccaggagcc atcgttctca gtgtcccctg gagggacagt cacactcact     120

```
tgtggcttga gctctggctc agtctctact agttactacc ccagctggta ccagcagacc    180
ccaggccagg ctccacgcac gctcatctac agcacaaaca ctcgctcttc tggggtccct    240
gatcgcttct ctggctccat ccttgggaac aaagctgccc tcaccatcac ggggggccag    300
gcagatgatg aatctgatta ttactgtgtg ctgtatatgg gtagtggcat ttgggtgttc    360
ggcggaggga ccaagctgac cgtcctaggt cagcccaagg ctgccccctc ggtcactctg    420
ttcccgccct cctctgagga gcttcaagcc aacaaggcca cactggtgtg tctcataagt    480
gacttctacc cgggagccgt gacagtggcc tggaaggcag atagcagccc cgtcaaggcg    540
ggagtggaga ccaccacacc ctccaaacaa agcaacaaca gtatgcggc cagcagctac    600 ctgagcctga cgcctgagca gtggaagtcc cacaaaagct acagctgcca ggtcacgcat    660
gaagggagca ccgtggagaa gacagtggcc cctacagaat gttcataa                708
```

<210> SEQ ID NO 33
<211> LENGTH: 270
<212> TYPE: PRT
<213> ORGANISM: Artificial Sequence
<220> FEATURE:
<223> OTHER INFORMATION: PMS212 VH
<400> SEQUENCE: 33

```
Met Lys Tyr Leu Leu Pro Thr Ala Ala Gly Leu Leu Leu Leu Ala
  1               5                  10                  15

Ala Gln Pro Ala Met Ala Glu Val Gln Leu Val Gln Ser Gly Gly
                 20                  25                  30

Val Val Gln Pro Gly Thr Ser Leu Arg Leu Ser Cys Thr Ala Ser Gly
             35                  40                  45

Phe Ile Phe Ser Asn Phe Gly Met His Trp Val Arg Gln Ala Pro Gly
 50                  55                  60

Lys Gly Leu Glu Trp Val Ala Val Ile Trp His Asp Gly Ser Asn Lys
 65                  70                  75                  80

Asn Tyr Ala Asp Ser Val Lys Gly Arg Phe Thr Ile Ser Arg Asp Asn
                 85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Asp Leu Val Gly Gly Gly Ala Phe
            115                 120                 125

Asp Ile Trp Gly Gln Gly Thr Met Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Ala Ala Ala His His His His His Gly Ala Ala
                245                 250                 255
```

```
        Glu Gln Lys Leu Ile Ser Glu Glu Asp Leu Asn Gly Ala Ala
                        260                 265                 270

<210> SEQ ID NO 34
<211> LENGTH: 235
<212> TYPE: PRT
<213> ORGANISM: Artificial Sequence
<220> FEATURE:
<223> OTHER INFORMATION: PMS212 VL

<400> SEQUENCE: 34

Val Lys Lys Leu Leu Phe Ala Ile Pro Leu Val Val Pro Phe Tyr Ser
1               5                   10                  15

His Ser Ala Gln Ala Val Val Ile Gln Glu Pro Ser Phe Ser Val Ser
            20                  25                  30

Pro Gly Gly Thr Val Thr Leu Thr Cys Gly Leu Ser Ser Gly Ser Val
        35                  40                  45

Ser Thr Ser Tyr Tyr Pro Ser Trp Tyr Gln Gln Thr Pro Gly Gln Ala
    50                  55                  60

Pro Arg Thr Leu Ile Tyr Ser Thr Asn Thr Arg Ser Ser Gly Val Pro
65                  70                  75                  80

Asp Arg Phe Ser Gly Ser Ile Leu Gly Asn Lys Ala Ala Leu Thr Ile
                85                  90                  95

Thr Gly Ala Gln Ala Asp Asp Glu Ser Asp Tyr Tyr Cys Val Leu Tyr
            100                 105                 110

Met Gly Ser Gly Ile Trp Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 35
<211> LENGTH: 813
<212> TYPE: DNA
<213> ORGANISM: Artificial Sequence
<220> FEATURE:
<223> OTHER INFORMATION: PMS213 VH

<400> SEQUENCE: 35
atgaaatacc tattgcctac ggcagccgct ggattgttat tactcgcggc ccagccggcc      60
atggcccagg tgcagctggt gcagtctggc ccaggactgg tgaagccttc ggagaccctg     120
tccctcatct gcactgtctc tggtggctcc atcagcagta gtaattacta ctggggctgg     180
gtccgccagc ccccagggaa ggggctggag tggattggga ctatctatta gtgggacc      240 acctactaca acccgtccct caagagtcga gtcaccatat ccgtagacac gtccaagaac     300
cagttctccc tggagctgag ctctgtgacc gccgcagaca cggccgtgta ttactgtgcg     360
```

```
agacttggga gggggagtgc ttttgatatc tggggccaag ggacaatggt caccgtctca      420
agcgcctcca ccaagggccc atcggtcttc ccctggcac cctcctccaa gagcacctct       480 ggggcacag cggccctggg ctgcctggtc aaggactact ccccgaacc ggtgacggtg        540 tcgtggaact caggcgccct gaccagcggc gtccacacct ccccggctgt cctacagtcc      600
tcaggactct actccctcag cagcgtagtg accgtgccct ccagcagctt gggcacccag      660
acctacatct gcaacgtgaa tcacaagccc agcaacacca aggtggacaa gaaagttgag      720
cccaaatctt gtgcggccgc acatcatcat caccatcacg gggccgcaga caaaaactc      780 atctcagaag aggatctgaa tggggccgca tag                                   813
```

<210> SEQ ID NO 36
<211> LENGTH: 708
<212> TYPE: DNA
<213> ORGANISM: Artificial Sequence
<220> FEATURE:
<223> OTHER INFORMATION: PMS213 VL

<400> SEQUENCE: 36

```
gtgaaaaaat tattattcgc aattcctta gttgttcctt tctattctca cagtgcacag        60
tctgtcgtga cgcagccgcc ctcactgtct gcggccccag gacagagcat caccatctcc      120
tgctctggag gcggctccaa tattgggaga aattctgtgt cgtggcaccg gcaattcccg      180
ggagcagccc ccgaactcct cgcatttgac acttttaggc ggccctcagg tgttcctgac      240
cgattctctg gttccaagtc tggctcgtcg gccacccctgg tcatcaccgg actccagact     300
ggggacgagg ccgactatta ctgtggaact tgggataatt cactggattc tggagtcttc     360
ggcggaggga ccaaggtgac cgtcctacgt cagcccaagg ctgccccctc ggtcactcta     420
ttcccgccct cctctgagga gcttcaagcc aacaaggcca cactggtgtg tctcataagt      480
gacttctacc cgggagccgt gacagtggcc tggaaggcag atagcagccc cgtcaaggcg      540
agagtggaga ccaccacacc ctccaaacaa gcaacaacaa gtacgcggc cagcagctac       600 ctgagcctga cgcctgagca gtggaagtcc cacaaaagct acagctgcca ggtcacgcat      660
gaagggagca ccgtggagaa gacagtggcc cctacagaat gttcataa                   708
```

<210> SEQ ID NO 37
<211> LENGTH: 270
<212> TYPE: PRT
<213> ORGANISM: Artificial Sequence
<220> FEATURE:
<223> OTHER INFORMATION: PMS213 VH

<400> SEQUENCE: 37

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Pro Gly
            20                  25                  30

Leu Val Lys Pro Ser Glu Thr Leu Ser Leu Ile Cys Thr Val Ser Gly
        35                  40                  45

Gly Ser Ile Ser Ser Ser Asn Tyr Tyr Trp Gly Trp Val Arg Gln Pro
    50                  55                  60

Pro Gly Lys Gly Leu Glu Trp Ile Gly Thr Ile Tyr Tyr Ser Gly Thr
65                  70                  75                  80

Thr Tyr Tyr Asn Pro Ser Leu Lys Ser Arg Val Thr Ile Ser Val Asp
                85                  90                  95
```

Thr Ser Lys Asn Gln Phe Ser Leu Glu Leu Ser Ser Val Thr Ala Ala
            100                 105                 110

Asp Thr Ala Val Tyr Tyr Cys Ala Arg Leu Gly Arg Gly Ser Ala Phe
        115                 120                 125

Asp Ile Trp Gly Gln Gly Thr Met Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Ala Ala Ala His His His His His Gly Ala Ala
                245                 250                 255

Glu Gln Lys Leu Ile Ser Glu Glu Asp Leu Asn Gly Ala Ala
            260                 265                 270

<210> SEQ ID NO 38
<211> LENGTH: 235
<212> TYPE: PRT
<213> ORGANISM: Artificial Sequence
<220> FEATURE:
<223> OTHER INFORMATION: PMS213 VL

<400> SEQUENCE: 38

Val Lys Lys Leu Leu Phe Ala Ile Pro Leu Val Val Pro Phe Tyr Ser
1               5                   10                  15

His Ser Ala Gln Ser Val Val Thr Gln Pro Pro Ser Leu Ser Ala Ala
            20                  25                  30

Pro Gly Gln Ser Ile Thr Ile Ser Cys Ser Gly Gly Gly Ser Asn Ile
        35                  40                  45

Gly Arg Asn Ser Val Ser Trp His Arg Gln Phe Pro Gly Ala Ala Pro
    50                  55                  60

Glu Leu Leu Ala Phe Asp Thr Phe Arg Arg Pro Ser Gly Val Pro Asp
65                  70                  75                  80

Arg Phe Ser Gly Ser Lys Ser Gly Ser Ser Ala Thr Leu Val Ile Thr
                85                  90                  95

Gly Leu Gln Thr Gly Asp Glu Ala Asp Tyr Tyr Cys Gly Thr Trp Asp
            100                 105                 110

Asn Ser Leu Asp Ser Gly Val Phe Gly Gly Gly Thr Lys Val Thr Val
        115                 120                 125

Leu Arg Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Arg Val Glu Thr Thr Thr Pro Ser Lys Gln Ser Asn
            180                 185                 190

```
Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 39
<211> LENGTH: 19
<212> TYPE: PRT
<213> ORGANISM: Artificial Sequence
<220> FEATURE:
<223> OTHER INFORMATION: VL leader sequence

<400> SEQUENCE: 39

Val Lys Lys Leu Leu Phe Ala Ile Pro Leu Val Val Pro Phe Tyr Ser
1               5                   10                  15

His Ser Ala

<210> SEQ ID NO 40
<211> LENGTH: 22
<212> TYPE: PRT
<213> ORGANISM: Artificial Sequence
<220> FEATURE:
<223> OTHER INFORMATION: VH leader sequence

<400> SEQUENCE: 40

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 41
<211> LENGTH: 2109
<212> TYPE: DNA
<213> ORGANISM: Artificial Sequence
<220> FEATURE:
<223> OTHER INFORMATION: PMS210-Fc

<400> SEQUENCE: 41
atgaaacatc tgtggttctt ccttctcctg gtggcagcgg cccagccggc ccaggtgcag      60
ctggtgcagt ctgggggagg cttggtacag cctggggagt ccctgcgact ctcctgtgca     120
gcctctggat tcacctttag caactatgcc atgagctggg tccgccaggc tccagggaag     180
gggctggagt gggtctcagc tattagtggt agtggtggta gcacatacta cgcagactcc     240
gtgaagggcc ggttcaccat ctccagagac agttccaaga acacgcttta tcttcaaatg     300
aacgacctga gaccgaggac acggctata tattactgtg cgagaagttt cactcttgac     360
tattggggcc agggaaccct ggtcaccgtc tcaagcgcct ccaccaaggg cccatcggtc     420
ttccccctgg caccctcctc caagagcacc tctgggggca gcggccct gggctgcctg     480 gtcaaggact acttccccga accggtgacg gtgtcgtgga actcaggcgc cctgaccagc     540
ggcgtccaca ccttcccggc tgtcctacag tcctcaggac tctactccct cagcagcgta     600
gtgaccgtgc cctccagcag cttgggcacc cagacctaca tctgcaacgt gaatcacaag     660
cccagcaaca ccaaggtgga caagaaagtt gagcccaaat cttgtggtgg cggcggttcc     720
ggaggtggtg gttctggcgg tggtggcagc ctttactatg tgctgactca gccaccctcg     780
gtgtccaagg gcttgagaca gaccgccaca ctcacctgca ctgggaacag caacaatatt     840
ggcaaccaag gagcagcttg gctgcagcag caccagggcc accctcccaa actcctatcc     900
```

```
tacaggaata caaccggcc ctcagggatc tcagagagat tatctgcatc caggtcagga    960
aatactgcct ccctgaccat tactggactc cagcctgagg acgaggctga ctattactgc   1020
tcatcatggg acagcagtct gaaagttcag gtgttcggcg agggaccaa gctgaccgtc    1080
ctaggtcagc ccaaggctgc ccctcggtc actctgttcc caccctcctc tgaggagctt    1140
caagccaaca aggccacact ggtgtgtctc ataagtgact tctacccggg agccgtgaca   1200
gtggcctgga aggcagatag cagccccgtc aaggcgggag tggagaccac cacaccctcc   1260
aaacaaagca acaacaagta cgcggccagc agctacctga gcctgacgcc tgagcagtgg   1320
aagtcccaca aaagctacag ctgccaggtc acgcatgaag ggagccacgt ggagaagaca   1380
gtggccccta cagaatgttc agcggccgca gagcccaaat cttgtgacaa aactcacaca   1440
tgcccaccgt gcccagcacc tgaactcctg ggggaccgt cagtcttcct cttccccca    1500
aaacccaagg acaccctcat gatctcccgg acccctgagg tcacatgcgt ggtggtggac   1560
gtgagccacg aagaccctga ggtcaagttc aactggtacg tggacggcgt ggaggtgcat   1620
aatgccaaga caaagccgcg ggaggagcag tacaacagca cgtaccgtgt ggtcagcgtc   1680
ctcaccgtcc tgcaccagga ctggctgaat ggcaaggagt acaagtgcaa ggtctccaac   1740
aaagccctcc cagccccat cgagaaaacc atctccaaag ccaagggca gccccgagaa    1800
ccacaggtgt acaccctgcc cccatcccgg gatgagctga ccaagaacca ggtcagcctg   1860
acctgcctgg tcaaaggctt ctatcccagc gacatcgccg tggagtggga gagcaatggg   1920
cagccggaga caactacaa gaccacgcct cccgtgctgg actccgacgg ctccttcttc    1980
ctctacagca agctcaccgt ggacaagagc aggtggcagc aggggaacgt cttctcatgc   2040
tccgtgatgc atgaggctct gcacaaccac tacacgcaga agagcctctc cctgtctccg   2100
ggtaaatga                                                          2109

<210> SEQ ID NO 42
<211> LENGTH: 702
<212> TYPE: PRT
<213> ORGANISM: Artificial Sequence
<220> FEATURE:
<223> OTHER INFORMATION: PMS210-Fc

<400> SEQUENCE: 42

Met Lys His Leu Trp Phe Phe Leu Leu Leu Val Ala Ala Ala Gln Pro
1               5                   10                  15

Ala Gln Val Gln Leu Val Gln Ser Gly Gly Gly Leu Val Gln Pro Gly
            20                  25                  30

Arg Ser Leu Arg Leu Ser Cys Ala Ala Ser Gly Phe Thr Phe Ser Asn
        35                  40                  45

Tyr Ala Met Ser Trp Val Arg Gln Ala Pro Gly Lys Gly Leu Glu Trp
    50                  55                  60

Val Ser Ala Ile Ser Gly Ser Gly Gly Ser Thr Tyr Tyr Ala Asp Ser
65                  70                  75                  80

Val Lys Gly Arg Phe Thr Ile Ser Arg Asp Ser Ser Lys Asn Thr Leu
                85                  90                  95

Tyr Leu Gln Met Asn Asp Leu Arg Ala Glu Asp Thr Ala Ile Tyr Tyr
            100                 105                 110

Cys Ala Arg Ser Phe Thr Leu Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140
```

-continued

| | | | | | | | | | | | |
|---|---|---|---|---|---|---|---|---|---|---|---|
|Pro|Ser|Ser|Lys|Ser|Thr|Ser|Gly|Gly|Thr|Ala|Ala|Leu|Gly|Cys|Leu|
|145| | | | |150| | | | |155| | | | |160|

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Lys Val Glu Pro Lys Ser Cys Gly Gly Gly Gly Ser
225                 230                 235                 240

Gly Gly Gly Gly Ser Gly Gly Gly Ser Leu Tyr Tyr Val Leu Thr
                245                 250                 255

Gln Pro Pro Ser Val Ser Lys Gly Leu Arg Gln Thr Ala Thr Leu Thr
            260                 265                 270

Cys Thr Gly Asn Ser Asn Asn Ile Gly Asn Gln Gly Ala Ala Trp Leu
        275                 280                 285

Gln Gln His Gln Gly His Pro Pro Lys Leu Leu Ser Tyr Arg Asn Asn
    290                 295                 300

Asn Arg Pro Ser Gly Ile Ser Glu Arg Leu Ser Ala Ser Arg Ser Gly
305                 310                 315                 320

Asn Thr Ala Ser Leu Thr Ile Thr Gly Leu Gln Pro Glu Asp Glu Ala
                325                 330                 335

Asp Tyr Tyr Cys Ser Ser Trp Asp Ser Leu Lys Val Gln Val Phe
            340                 345                 350

Gly Gly Gly Thr Lys Leu Thr Val Leu Gly Gln Pro Lys Ala Ala Pro
        355                 360                 365

Ser Val Thr Leu Phe Pro Pro Ser Ser Glu Glu Leu Gln Ala Asn Lys
    370                 375                 380

Ala Thr Leu Val Cys Leu Ile Ser Asp Phe Tyr Pro Gly Ala Val Thr
385                 390                 395                 400

Val Ala Trp Lys Ala Asp Ser Ser Pro Val Lys Ala Gly Val Glu Thr
                405                 410                 415

Thr Thr Pro Ser Lys Gln Ser Asn Asn Lys Tyr Ala Ala Ser Ser Tyr
            420                 425                 430

Leu Ser Leu Thr Pro Glu Gln Trp Lys Ser His Lys Ser Tyr Ser Cys
        435                 440                 445

Gln Val Thr His Glu Gly Ser Thr Val Glu Lys Thr Val Ala Pro Thr
    450                 455                 460

Glu Cys Ser Ala Ala Glu Pro Lys Ser Cys Asp Lys Thr His Thr
465                 470                 475                 480

Cys Pro Pro Cys Pro Ala Pro Glu Leu Leu Gly Gly Pro Ser Val Phe
                485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser His Glu Asp Pro Glu Val
        515                 520                 525

Lys Phe Asn Trp Tyr Val Asp Gly Val Glu Val His Asn Ala Lys Thr
    530                 535                 540

Lys Pro Arg Glu Glu Gln Tyr Asn Ser Thr Tyr Arg Val Val Ser Val
545                 550                 555                 560

```
Leu Thr Val Leu His Gln Asp Trp Leu Asn Gly Lys Glu Tyr Lys Cys
                565                 570                 575

Lys Val Ser Asn Lys Ala Leu Pro Ala Pro Ile Glu Lys Thr Ile Ser
            580                 585                 590

Lys Ala Lys Gly Gln Pro Arg Glu Pro Gln Val Tyr Thr Leu Pro Pro
        595                 600                 605

Ser Arg Asp Glu Leu Thr Lys Asn Gln Val Ser Leu Thr Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Lys Leu Thr Val Asp Lys Ser Arg Trp
            660                 665                 670

Gln Gln Gly Asn Val Phe Ser Cys Ser Val Met His Glu Ala Leu His
        675                 680                 685

Asn His Tyr Thr Gln Lys Ser Leu Ser Leu Ser Pro Gly Lys
    690                 695                 700

<210> SEQ ID NO 43
<211> LENGTH: 2118
<212> TYPE: DNA
<213> ORGANISM: Artificial Sequence
<220> FEATURE:
<223> OTHER INFORMATION: PMS212-Fc

<400> SEQUENCE: 43
```

| | | | | |
|---|---|---|---|---|
| atgaaacatc | tgtggttctt | ccttctcctg | gtggcagcgg | cccagccggc cgaggtccag | 60 |
| ctggtgcagt | ctggggggagg | cgtggtccag | cctgggacgt | ccctgagact ctcctgtaca | 120 |
| gcgtctggat | ttatcttcag | taattttggc | atgcactggg | tccgccaggc tccaggcaag | 180 |
| gggctggaat | gggtggctgt | tatatggcat | gatggaagta | ataaaaacta tgcagactcc | 240 |
| gtgaagggcc | gattcaccat | ctccagagac | aattccaaga | cacgctgta tctgcaaatg | 300 |
| aacagcctga | gagctgagga | cacggccgtg | tattactgtg | cgagagactt agtgggagga | 360 |
| ggtgcttttg | atatctgggg | ccaagggaca | atggtcaccg | tctcaagcgc tccaccaag | 420 |
| ggcccatcgg | tcttccccct | ggcaccctcc | tccaagagca | cctctggggg cacagcggcc | 480 |
| ctgggctgcc | tggtcaagga | ctacttcccc | gaaccggtga | cggtgtcgtg aactcaggc | 540 |
| gccctgacca | gcggcgtcca | caccttcccg | gctgtcctac | agtcctcagg actctactcc | 600 |
| ctcagcagcg | tagtgaccgt | gccctccagc | agcttgggca | cccagaccta catctgcaac | 660 |
| gtgaatcaca | agcccagcaa | caccaaggtg | gacaagaaag | ttgagcccaa atcttgtggt | 720 |
| ggcggcggtt | ccgaggtgg | tggttctggc | ggtggtggca | gccaggctgt ggtgatccag | 780 |
| gagccatcgt | tctcagtgtc | cctggaggg | acagtcacac | tcacttgtgg cttgagctct | 840 |
| ggctcagtct | ctactagtta | ctaccccagc | tggtaccagc | agaccccagg ccaggctcca | 900 |
| cgcacgctca | tctacagcac | aaacactcgc | tcttctgggg | tccctgatcg cttctctggc | 960 |
| tccatccttg | gaacaaagc | tgccctcacc | atcacggggg | cccaggcaga tgatgaatct | 1020 |
| gattattact | gtgtgctgta | tatgggtagt | ggcatttggg | tgttcggcgg agggaccaag | 1080 |
| ctgaccgtcc | taggtcagcc | caaggctgcc | ccctcggtca | ctctgttccc gccctcctct | 1140 |
| gaggagcttc | aagccaacaa | ggccacactg | gtgtgtctca | taagtgactt ctacccggga | 1200 |
| gccgtgacag | tggcctggaa | ggcagatagc | agccccgtca | aggcgggagt ggagaccacc | 1260 |

```
acaccctcca acaaagcaa caacaagtat gcggccagca gctacctgag cctgacgcct   1320
gagcagtgga agtcccacaa aagctacagc tgccaggtca cgcatgaagg gagcaccgtg   1380
gagaagacag tggcccctac agaatgttca gcggccgcag agcccaaatc ttgtgacaaa   1440
actcacacat gcccaccgtg cccagcacct gaactcctgg ggggaccgtc agtcttcctc   1500
ttccccccaa aacccaagga caccctcatg atctcccgga cccctgaggt cacatgcgtg   1560
gtggtggacg tgagccacga agaccctgag gtcaagttca actggtacgt ggacggcgtg   1620
gaggtgcata atgccaagac aaagccgcgg gaggagcagt acaacagcac gtaccgtgtg   1680
gtcagcgtcc tcaccgtcct gcaccaggac tggctgaatg gcaaggagta caagtgcaag   1740
gtctccaaca aagccctccc agcccccatc gagaaaacca tctccaaagc caaagggcag   1800
ccccgagaac cacaggtgta caccctgccc ccatcccggg atgagctgac caagaaccag   1860
gtcagcctga cctgcctggt caaaggcttc tatcccagcg acatcgccgt ggagtgggag   1920
agcaatgggc agccggagaa caactacaag accacgcctc ccgtgctgga ctccgacggc   1980
tccttcttcc tctacagcaa gctcaccgtg gacaagagca ggtggcagca ggggaacgtc   2040
ttctcatgct ccgtgatgca tgaggctctg cacaaccact acacgcagaa gagcctctcc   2100
ctgtctccgg gtaaatga                                                 2118
```

<210> SEQ ID NO 44
<211> LENGTH: 705
<212> TYPE: PRT
<213> ORGANISM: Artificial Sequence
<220> FEATURE:
<223> OTHER INFORMATION: PMS212-Fc

<400> SEQUENCE: 44

```
Met Lys His Leu Trp Phe Phe Leu Leu Leu Val Ala Ala Ala Gln Pro
1               5                   10                  15

Ala Glu Val Gln Leu Val Gln Ser Gly Gly Gly Val Val Gln Pro Gly
            20                  25                  30

Thr Ser Leu Arg Leu Ser Cys Thr Ala Ser Gly Phe Ile Phe Ser Asn
        35                  40                  45

Phe Gly Met His Trp Val Arg Gln Ala Pro Gly Lys Gly Leu Glu Trp
    50                  55                  60

Val Ala Val Ile Trp His Asp Gly Ser Asn Lys Asn Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Arg Asp Leu Val Gly Gly Ala Phe Asp Ile Trp Gly Gln
        115                 120                 125

Gly Thr Met Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205
```

```
Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Gly
225                 230                 235                 240

Gly Gly Gly Ser Gly Gly Gly Ser Gly Gly Gly Ser Gln Ala
            245                 250                 255

Val Val Ile Gln Glu Pro Ser Phe Ser Val Ser Pro Gly Gly Thr Val
            260                 265                 270

Thr Leu Thr Cys Gly Leu Ser Ser Gly Ser Val Ser Thr Ser Tyr Tyr
        275                 280                 285

Pro Ser Trp Tyr Gln Gln Thr Pro Gly Gln Ala Pro Arg Thr Leu Ile
290                 295                 300

Tyr Ser Thr Asn Thr Arg Ser Ser Gly Val Pro Asp Arg Phe Ser Gly
305                 310                 315                 320

Ser Ile Leu Gly Asn Lys Ala Ala Leu Thr Ile Thr Gly Ala Gln Ala
                325                 330                 335

Asp Asp Glu Ser Asp Tyr Tyr Cys Val Leu Tyr Met Gly Ser Gly Ile
            340                 345                 350

Trp Val Phe Gly Gly Gly Thr Lys Leu Thr Val Leu Gly Gln Pro Lys
        355                 360                 365

Ala Ala Pro Ser Val Thr Leu Phe Pro Pro Ser Ser Glu Glu Leu Gln
370                 375                 380

Ala Asn Lys Ala Thr Leu Val Cys Leu Ile Ser Asp Phe Tyr Pro Gly
385                 390                 395                 400

Ala Val Thr Val Ala Trp Lys Ala Asp Ser Ser Pro Val Lys Ala Gly
                405                 410                 415

Val Glu Thr Thr Thr Pro Ser Lys Gln Ser Asn Asn Lys Tyr Ala Ala
            420                 425                 430

Ser Ser Tyr Leu Ser Leu Thr Pro Glu Gln Trp Lys Ser His Lys Ser
        435                 440                 445

Tyr Ser Cys Gln Val Thr His Glu Gly Ser Thr Val Glu Lys Thr Val
450                 455                 460

Ala Pro Thr Glu Cys Ser Ala Ala Ala Glu Pro Lys Ser Cys Asp Lys
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Arg Asp Glu Leu Thr Lys Asn Gln Val Ser Leu Thr
610                 615                 620

Cys Leu Val Lys Gly Phe Tyr Pro Ser Asp Ile Ala Val Glu Trp Glu
```

```
                625                 630                 635                 640
Ser Asn Gly Gln Pro Glu Asn Asn Tyr Lys Thr Thr Pro Pro Val Leu
                    645                 650                 655

Asp Ser Asp Gly Ser Phe Phe Leu Tyr Ser Lys Leu Thr Val Asp Lys
                660                 665                 670

Ser Arg Trp Gln Gln Gly Asn Val Phe Ser Cys Ser Val Met His Glu
        675                 680                 685

Ala Leu His Asn His Tyr Thr Gln Lys Ser Leu Ser Leu Ser Pro Gly
    690                 695                 700

Lys
705

<210> SEQ ID NO 45
<211> LENGTH: 30
<212> TYPE: DNA
<213> ORGANISM: Artificial Sequence
<220> FEATURE:
<223> OTHER INFORMATION: myc-tag

<400> SEQUENCE: 45
gaacaaaaac tcatctcaga agaggatctg                                        30

<210> SEQ ID NO 46
<211> LENGTH: 18
<212> TYPE: DNA
<213> ORGANISM: Artificial Sequence
<220> FEATURE:
<223> OTHER INFORMATION: 6xHis-tag

<400> SEQUENCE: 46
catcatcatc accatcac                                                     18

<210> SEQ ID NO 47
<211> LENGTH: 15
<212> TYPE: PRT
<213> ORGANISM: Artificial Sequence
<220> FEATURE:
<223> OTHER INFORMATION: linker

<400> SEQUENCE: 47

Gly Gly Gly Gly Ser Gly Gly Gly Gly Ser Gly Gly Gly Gly Ser
1               5                   10                  15

<210> SEQ ID NO 48
<211> LENGTH: 66
<212> TYPE: DNA
<213> ORGANISM: Artificial Sequence
<220> FEATURE:
<223> OTHER INFORMATION: VH leader sequence

<400> SEQUENCE: 48
atgaaatacc tattgcctac ggcagccgct ggattgttat tactcgcggc ccagccggcc       60
atggcc                                                                  66

<210> SEQ ID NO 49
<211> LENGTH: 57
<212> TYPE: DNA
<213> ORGANISM: Artificial Sequence
<220> FEATURE:
<223> OTHER INFORMATION: VL leader sequence

<400> SEQUENCE: 49
gtgaaaaaat tattattcgc aattccttta gttgttcctt tctattctca cagtgca          57
```

```
<210> SEQ ID NO 50
<211> LENGTH: 5
<212> TYPE: PRT
<213> ORGANISM: Artificial Sequence
<220> FEATURE:
<223> OTHER INFORMATION: PMS208 VH CDR1-Kabat

<400> SEQUENCE: 50

Ser His Tyr Trp Ser
1               5

<210> SEQ ID NO 51
<211> LENGTH: 16
<212> TYPE: PRT
<213> ORGANISM: Artificial Sequence
<220> FEATURE:
<223> OTHER INFORMATION: PMS208 VH CDR2-Kabat

<400> SEQUENCE: 51

Tyr Ile Tyr Asp Ser Gly Ser Thr Asn Tyr Asn Pro Ser Leu Lys Ser
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: PMS208 VH CDR3-Kabat

<400> SEQUENCE: 52

Gly Ala Gly Trp Tyr Arg Phe
1               5

<210> SEQ ID NO 53
<211> LENGTH: 17
<212> TYPE: PRT
<213> ORGANISM: Artificial Sequence
<220> FEATURE:
<223> OTHER INFORMATION: PMS208 VL CDR1-Kabat

<400> SEQUENCE: 53

Lys Ser Ser Gln Ser Val Leu Tyr Ser Ser Asn Asn Lys Asn Tyr Leu
1               5                   10                  15

Ala

<210> SEQ ID NO 54
<211> LENGTH: 7
<212> TYPE: PRT
<213> ORGANISM: Artificial Sequence
<220> FEATURE:
<223> OTHER INFORMATION: PMS208 VL CDR2-Kabat

<400> SEQUENCE: 54

Trp Ala Ser Thr Arg Glu Ser
1               5
```

ANTIBODIES FOR THE TREATMENT OF SYNUCLEINOPATHIES AND NEUROINFLAMMATION

CROSS-REFERENCE TO RELATED APPLICATIONS

This application is a U.S. National Phase of International Application No. PCT/IB2019/055461, filed Jun. 27, 2019, which claims priority to U.S. Provisional Application No. 62/690,733, filed Jun. 27, 2018, each of which is herein incorporated by reference in its entirety.

FIELD AND BACKGROUND OF THE INVENTION

The present invention, in some embodiments thereof, relates to antibodies for the treatment of synucleinopathies and neuroinflammation.

Several neurodegenerative diseases, including Parkinson disease (PD), PD dementia (PDD), dementia with Lewy bodies (DLB), and multiple system atrophy (MSA), are associated with abnormal accumulation of α-synuclein (α-syn) in the brain and hence are collectively termed "α-synucleinopathies." These diseases have distinct, as well as overlapping, features that seem to fall along a spectrum.

PD, the most common neurodegenerative movement disorder and the most common α-synucleinopathy, has an estimated worldwide prevalence of 570 per 100,000 among people aged 50 and older, increasing with age. PD is clinically characterized by parkinsonism (i.e., bradykinesia, muscular rigidity, rest tremor, and postural and gait impairment), as well as non-motor features, including cognitive impairment, autonomic dysfunction, and rapid eye movement (REM) sleep behaviour disorder (RBD). Single gene mutations are a rare cause of PD. The etiology of sporadic PD remains unknown but probably involves the complex interplay of genetic and environmental factors. Irrespective of etiology, all cases of PD show loss of dopaminergic neurons in the substantia nigra pars compacta (SN), and most show Lewy pathology including Lewy bodies and Lewy neuritis. Histological examination of Lewy pathology shows that α-syn is the major component of the Lewy body. Thus, it has been suggested that downstream effects of α-syn are a principal factor in the pathogenesis.

The pathology of PDD and DLB can be pure Lewy pathology with cortical Lewy bodies, or a mixed pathology with Lewy bodies, as well as amyloid-β plaques and neurofibrillary tangles. MSA is clinically characterized by autonomic dysfunction with parkinsonism or cerebellar symptoms. Lewy bodies can be seen in MSA, but the presence of α-syn aggregates in oligodendrocytes, called glial cytoplasmic inclusions, is a prerequisite for a definitive pathological diagnosis. There are additional neurodegenerative diseases with evident Lewy pathology including Gaucher disease and additional lysosomal storage disorders, a subset of neurodegeneration with brain iron accumulation (NBIA) disorders and AD.

As mentioned, the principal component of the intracellular inclusions is α-synuclein, a protein of 140 amino acids that is ubiquitously expressed in neurons (Jakes et al. *FEBS Lett.* 345:27-32(1994)). α-synuclein is intrinsically disordered in the cytosol; however it adopts an alpha-helical conformation when it becomes bound to cellular membranes (Burre et al. *Nature.* 498:E4-E6(2013)). The normal function of α-synuclein is yet to be fully determined; however, it is thought to regulate neurotransmitter release (Burre et al. *Science* 329:1663-1667 (2010)) and can also be found in the cytosol and mitochondria (Chinta et al. *Neurosci. Lett.* 486:235-239 (2010)). It has also been shown that α-synuclein can be secreted and transferred to nearby cells (Hansen et al. *J. Clin. Invest.* 121:715-725(2011)), thus potentially facilitating spreading of Lewy pathology within the central nervous system (CNS) (Braak et al. *Neurobiol Aging.* 24:197-211(2003)). The aggregation of α-synuclein presumably starts with a conformational shift of the monomeric protein, followed by the step-wise formation of larger multimeric protein species comprising toxic soluble oligomers and preformed fibrils (PFF). These forms are potential drivers of seeding of aggregated forms, which are taken up by neuronal cells and catalyze the conversion of alpha-synuclein soluble protein molecules into their aggregated forms and subsequent propagation culminating in widespread Lewy body pathology.

Microglia are one of the major cell types involved in the inflammatory responses in the CNS that appear to contribute to neuroinflammation in PD pathogenesis. Positron emission tomography (PET) studies also suggest that there is significant activation of microglia in various regions of PD brains. This proinflammatory local state is evident by expression of tumor necrosis factor-α (TNF-α or TNFα), interleukin-1β (IL-1β), and interferon-gamma (IFN-γ) in the midbrain of PD patients (Colonna and Butovsky, *Annu Rev Immunol.* 35:441-468 (2017)). These findings strongly suggest the involvement of immune components in PD pathogenesis.

Recently, it has also been shown that PD patients exhibit a systemic autoimmune response to α-syn modified forms further attesting to the role of inflammation in the pathogenesis.

Activation of microglia by dying neurons or by various forms of α-syn as well as T cells could result in a vicious circle of neuroinflammation and neurodegeneration that is self-perpetuating and drives the progression of PD. Some of the substances liberated by degenerating neurons include α-synuclein aggregates, neuromelanin, adenosine triphosphate (ATP), and matrix metalloproteinase-3 (MMP-3) (Colonna and Butovsky 2017, supra).

The understanding that α-synuclein oligomers/PFF are responsible for the neurotoxicity in Lewy body pathology led to the development of several immunotherapy strategies (Brundin et al., *Exp Neurol.* 298:225-235 (2017)). Animal models have supported the efficacy of active and passive immunotherapy with antibodies targeting modified forms of α-syn. Clinical trials with monoclonal antibodies are at their early stages, and the major hurdles to be overcome are the difficulty in achieving meaningful levels of the large molecular weight antibody (e.g., an IgG antibody) and the potentially deleterious effects of having to dose the antibody with very high quantities thus potentially increasing side effects. Also, the large size of a full antibody does not allow penetration into intraneuronal spaces that represent the bulk of lewy bodies.

SUMMARY OF THE INVENTION

Provided herein are antibodies and antigen-binding fragments thereof that are capable of binding to alpha-synuclein and methods of making and using the same.

In one aspect, an isolated antibody or antigen-binding fragment thereof capable of binding to soluble monomers, oligomers, and/or preformed fibrils of alpha-synuclein comprises a complementary determining region (CDR) H1 comprising the amino acid sequence set forth in SEQ ID NO:1 (GGSISSHY), a CDR H2 comprising the amino acid sequence set forth in SEQ ID NO:2 (IYDSGST), a CDR H3 comprising the amino acid sequence set forth in SEQ ID NO:3 (ARGAGWYRF), a CDR L1 comprising the amino acid sequence set forth in SEQ ID NO:4 (QSVLYSSNNKNY), a CDR2 L2 comprising the amino acid sequence set forth in SEQ ID NO:5 (WAS), and a CDR3 L3 comprising the amino acid sequence set forth in SEQ ID NO:6 (QQYYSTPRT). In one aspect, an isolated antibody or antigen-binding fragment thereof capable of binding to soluble monomers, oligomers, and/or preformed fibrils of alpha-synuclein comprises a CDR H1 comprising the amino acid sequence set forth in SEQ ID NO:50 (SHYWS), a CDR H2 comprising the amino acid sequence set forth in SEQ ID NO:51 (YIYDSGSTNYNPSLKS), a CDR H3 comprising the amino acid sequence set forth in SEQ ID NO:52 (GAGWYRF), a CDR L1 comprising the amino acid sequence set forth in SEQ ID NO:53 (KSSQSVLYSSNNK-NYLA), a CDR2 L2 comprising the amino acid sequence set forth in SEQ ID NO:54 (WASTRES), and a CDR3 L3 comprising the amino acid sequence set forth in SEQ ID NO:55 (QQYYSTPRT).

In one aspect, the antibody or antigen-binding fragment thereof comprises a heavy chain variable region (VH), wherein the VH comprises the same amino acid sequence as the VH encoded by the plasmid of ATCC Deposit Designation PTA-125004. In one aspect, the antibody or antigen-binding fragment thereof comprises a light chain variable region (VL), wherein the VL comprises the same amino acid sequence as the VL encoded by the plasmid of ATCC Deposit Designation PTA-125004.

In one aspect, an antibody or antigen-binding fragment thereof capable of binding to soluble monomers, oligomers, and/or preformed fibrils of alpha-synuclein comprises a VH and a VL, wherein the VH comprises the same amino acid sequence as the VH encoded by the plasmid of ATCC Deposit Designation PTA-125004.

In one aspect, an antibody or antigen-binding fragment thereof capable of binding to soluble monomers, oligomers, and/or preformed fibrils of alpha-synuclein comprises a VH and a VL, wherein the VL comprises the same amino acid sequence as the VL encoded by the plasmid of ATCC Deposit Designation PTA-125004.

In one aspect, an antibody or antigen-binding fragment thereof capable of binding to soluble monomers, oligomers, and/or preformed fibrils of alpha-synuclein comprises CDR H1, CDR H2, CDR H3, CDR L1, CDR L2, and CDR L3 comprising the CDR H1, CDR H2, CDR H3, CDR L1, CDR L2, and CDR L3 amino acid sequences encoded by the plasmid of ATCC Deposit Designation PTA-125004.

In one aspect, an antibody or antigen-binding fragment thereof capable of binding to soluble monomers, oligomers, and/or preformed fibrils of alpha-synuclein comprises CDR H1, CDR H2, CDR H3, CDR L1, CDR L2, and CDR L3 comprising the CDR H1, CDR H2, CDR H3, CDR L1, CDR L2, and CDR L3 amino acid sequences of PMS209, PMS210, PMS211, PMS212, or PMS213.

In one aspect, the CDRs are the Kabat-defined CDRs, the Chothia-defined CDRs, the AbM-defined CDRs, or the IMGT-defined CDRs.

In one aspect, the antibody or antigen binding fragment thereof comprises a VH and a VL, wherein the VH comprises the mature form of the amino acid sequence set forth in SEQ ID NOs:21, 25, 29, 33, or 37; wherein the VL comprises the mature form of the amino acid sequence set forth in SEQ ID NOs:22, 26, 30, 34, or 38; or wherein the VH and VL comprise the mature forms of SEQ ID NOs:21 and 22, respectively, SEQ ID NOs:25 and 26, respectively, SEQ ID NOs:29 and 30, respectively, SEQ ID NOs: 33 and 34, respectively, or SEQ ID NOs:37 and 38, respectively.

In one aspect, the antibody or antigen-binding fragment thereof is capable of binding to soluble monomers, oligomers, and/or preformed fibrils of alpha-synuclein with an affinity below 10 nM as measured by surface plasmon resonance.

In one aspect, the alpha-synuclein is human alpha-synuclein. In one aspect, the alpha-synuclein is mouse alpha-synuclein.

In one aspect, the antibody or antigen-binding fragment thereof is human, humanized, or chimeric.

In one aspect, the antibody or antigen-binding fragment thereof is an IgG antibody. In one aspect, the IgG is an IgG1 or IgG4. In one aspect, the antibody is an antigen-binding fragment of an antibody. In one aspect, the fragment is selected from the group consisting of Fab, F(ab')2, Fv, scFv, scFv-Fc, dsFv and a single domain molecule. In one aspect, the fragment is an scFv. In one aspect, the fragment is a Fab. In one aspect, the fragment is an intrabody. In one aspect, antigen-binding fragment is devoid of an Fc region. In one aspect, the antibody or antigen-binding fragment thereof comprises a VH and a VL on the same polypeptide chain. In one aspect, the linker comprises the sequence GGGGSGGGGSGGGGS (SEQ ID NO:47).

In one aspect, the antibody or antigen-binding fragment thereof comprises the amino acid sequence of the mature form of SEQ ID NO:42 or 44.

In one aspect, the antibody or antigen-binding fragment thereof is conjugated to an agent selected from the group consisting of a therapeutic agent, a prodrug, a peptide, a protein, an enzyme, a virus, a lipid, a biological response modifier, a pharmaceutical agent, and PEG.

In one aspect, the antibody or antigen-binding fragment thereof is capable of inhibiting expression and/or secretion of pro-inflammatory cytokines from microglia cells incubated with misfolded alpha synuclein. In one aspect, the antibody or antigen-binding fragment thereof is capable of inhibiting uptake of misfolded alpha synuclein by macrophages. In one aspect, the antibody or antigen-binding fragment thereof is capable of inhibiting T cell activation by misfolded alpha synuclein. In one aspect, the antibody or antigen-binding fragment thereof is capable of preventing aggregation of alpha-synuclein as determined by Thioflavin T (ThT). In one aspect, the antibody or antigen-binding fragment thereof is capable of inhibiting seeding and spreading of alpha-synuclein by macrophages. In one aspect, the antibody or antigen-binding fragment thereof is capable of penetrating neurons, colocalizing with misfolded alpha synuclein, and/or attenuating consequent cellular toxicity. In one aspect, the antibody or antigen-binding fragment thereof is capable of ameliorating a motorical or physiological phenotype in a synucleinopathy mouse model.

Also provided herein are compositions comprising any antibody or antigen-binding fragment thereof provided herein and a carrier. In one aspect, the composition is a diagnostic composition. In one aspect, the composition is a therapeutic composition. In one aspect, the composition is a vaccine.

Also provided herein are isolated polynucleotides comprising a nucleic acid molecule encoding the heavy chain variable region or heavy chain of any antibody or antigen-binding fragment thereof provided herein. In one aspect, the isolated polynucleotide further comprises a nucleic acid molecule encoding the light chain variable region or light chain of the antibody or antigen-binding fragment thereof of the antibody or antigen-binding fragment thereof provided herein. In one aspect, the nucleic acid molecule encodes a VH comprising the same amino acid sequence as the VH encoded by the plasmid of ATCC Deposit Designation PTA-125004 or wherein the nucleic acid molecule encodes a VH comprising the amino acid sequence of SEQ ID NOs:21, 25, 29, 33, or 37. In one aspect, the nucleic acid molecule comprises the VH-encoding polynucleotide sequence of ATCC Deposit Designation PTA-125004 or wherein the nucleic acid molecule comprises the nucleotide sequence of SEQ ID NOs:19, 23, 27, 31, or 35.

Also provided herein are isolated polynucleotides comprising a nucleic acid molecule encoding the light chain variable region or light chain of any antibody or antigen-binding fragment thereof provided herein.

In one aspect, the nucleic acid molecule encodes a VL comprising the same amino acid sequence as the VL encoded by the plasmid of ATCC Deposit Designation PTA-125004 or wherein the nucleic acid molecule encodes a VH comprising the amino acid sequence of SEQ ID NOs:22, 26, 30, 34, or 28. In one aspect, the nucleic acid molecule comprises the VL-encoding polynucleotide sequence of ATCC Deposit Designation PTA-125004 or wherein the nucleic acid molecule encodes a VH comprising the amino acid sequence of any of SEQ ID NOs:20, 24, 28, 32, or 36.

Also provided herein are isolated vectors comprising any polynucleotide provided herein. In one aspect, the polynucleotide is operably linked to a cis-acting regulatory element. In one aspect, the vector comprises a promoter sequence for driving expression of the polynucleotide and/or an internal ribosome entry site (IRES). In one aspect, the vector is a viral vector. In one aspect, the viral vector is an adenoviral vector, an adeno associated viral vector (AAV), or a lentiviral vector. In one aspect, the AAV is AAV9, AAV8, AAV7, AAV6, AAV5, AAV2, or AAV8-DJ.

Also provided herein are host cells comprising any polynucleotide provided herein, any vector provided herein, or a combination of vectors comprising polynucleotides provided herein.

Also provided herein are pharmaceutical compositions comprising any antibody or antigen-binding fragment provided herein, any vector provided herein, or any cell provided herein.

Also provided herein are methods of producing an anti-alpha synuclein antibody or antigen-binding fragment thereof comprising (a) culturing a cell provided herein in a cell culture under conditions which allow expression of said an alpha-synuclein antibody or antigen-binding fragment thereof, and (b) recovering the antibody or antigen-binding fragment thereof from said cell culture.

Also provided herein are anti-alpha synuclein antibodies or antigen-binding fragments thereof obtainable by the methods provided herein.

Also provided herein are methods of treating or preventing a synucleinopathic disease in a subject comprising administering to the subject a therapeutically effective amount of any antibody or antigen-binding fragment thereof, composition, polynucleotide, vector, or cell provided herein, thereby treating or preventing the synucleinopathic disease.

Also provided herein are methods of treating or preventing neuroinflammation in a subject comprising administering to the subject a therapeutically effective amount of any antibody or antigen-binding fragment thereof, composition, polynucleotide, vector, or cell provided herein, thereby treating or preventing the neuroinflammation.

In one aspect, the administering is via an administration route selected from the group consisting of intranasal, intravenous, subcutaneous, and intrathecal.

Also provided herein are method of diagnosing a synucleinopathic disease in a subject comprising (a) assessing the level, localization, conformation, or a combination thereof of misfolded alpha-synuclein in a subject to be diagnosed with any antibody or antigen-binding fragment thereof or composition provided herein; and (b) comparing the level, localization, conformation, or combination thereof of misfolded alpha-synuclein in the subject to one or more reference standards derived from one or more control samples, wherein a difference or similarity between the level, localization, conformation, or combination thereof of α-synuclein in the subject and the reference standard indicates whether the subject has a synucleinopathic disease.

In one aspect, the synucleinopathic disease is Parkinson's disease (PD), dementia with Lewy bodies (DLB), multiple systems atrophy (MSA), a neurodegenerative disease with cerebral deposits of misfolded alpha-synuclein, or a combination thereof, optionally wherein neurodegenerative disease with cerebral deposits of misfolded alpha-synuclein is Alzheimer's disease or frontotemportal dementia.

In one aspect, the level, localization, conformation, or combination thereof of misfolded and monomeric alpha-synuclein in the subject is measured by in vivo imaging. In one aspect, the in vivo imaging comprises positron emission tomography (PET), single photon emission tomography (SPECT), near infrared (NIR) optical imaging or magnetic resonance imaging (MM).

In one aspect, the subject is a mammal, optionally wherein the mammal is a human.

Also provided herein are methods of detecting misfolded alpha-synuclein comprising (a) contacting a biological sample with any antibody or antigen-binding fragment thereof provided herein or any composition provided herein under conditions which allow formation of immunocomplexes; and (b) determining the presence and/or level of the immunocomplexes. In one aspect, the antibody or antigen-binding fragment thereof is attached to a heterologous detectable moiety.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings.

Figure 1:
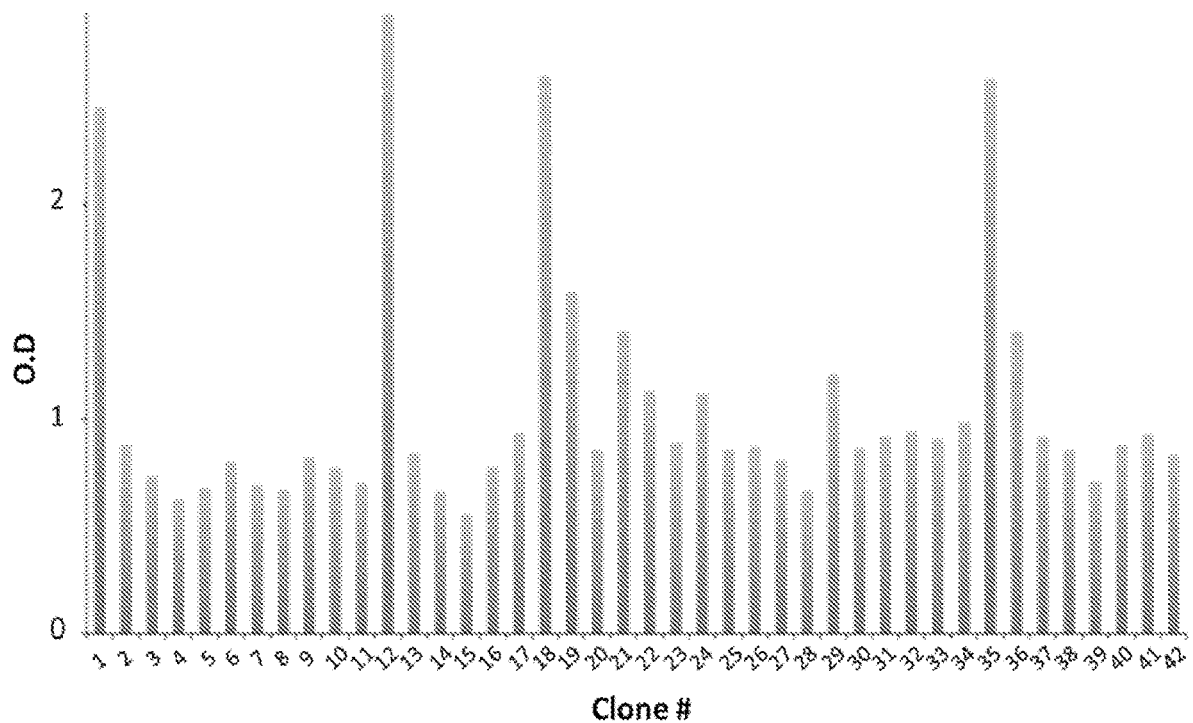
FIG. 1 is a bar graph of alpha-synuclein 42 positive Fab clone binders selected from a human scFv library: repertoire from over 110 individuals, diversity of 1×10[11].

FIG. 3A shows nucleic acid sequences of the variable regions from heavy (VH) and light (VL) chains in PMS209. The VH leader sequence (ATGAAATACCTATTGCC-TACGGCAGCCGCTGGATTGTTATTACTCGCGGCCC AGCCGGCCATGGCC; SEQ ID NO:48) corresponds to nucleotides 1-66 of SEQ ID NO:19. The VL leader sequence (GTGAAAAAATTATTATTCGCAATTCCTT-TAGTTGTTCCTTTCTATTCTCACAGT GCA; SEQ ID NO:49) corresponds to nucleotides 1-57 of SEQ ID NO:20. The 6×His-tag (CATCATCATCACCATCAC; SEQ ID NO:46) corresponds to nucleotides 754-771 of SEQ ID NO:19. The myc-tag (GAACAAAAACT-CATCTCAGAAGAGGATCTG; SEQ ID NO:45) corresponds to nucleotides 781-810 of SEQ ID NO:19. CDR sequences are underlined.

FIG. 3B shows nucleic acids sequences of the variable regions from heavy (VH) and light (VL) chains in PMS210. The VH leader sequence corresponds to nucleotides 1-66 of SEQ ID NO:23. The VL leader sequence corresponds to nucleotides 1-57 of SEQ ID NO:24. The 6×His-tag corresponds to nucleotides 730-747 of SEQ ID NO:23. The myc-tag corresponds to nucleotides 757-786 of SEQ ID NO:23. CDR sequences are underlined.

FIG. 3C shows nucleic acids sequences of the variable regions from heavy (VH) and light (VL) chains in PMS211. The VH leader sequence corresponds to nucleotides 1-66 of SEQ ID NO:27. The VL leader sequence corresponds to nucleotides 1-57 of SEQ ID NO:28. The 6×His-tag corresponds to nucleotides 733-750 of SEQ ID NO:27. The myc-tag corresponds to nucleotides 760-789 of SEQ ID NO:27. CDR sequences are underlined.

FIG. 3D shows nucleic acids sequences of the variable regions from heavy (VH) and light (VL) chains in PMS212. The VH leader sequence corresponds to nucleotides 1-66 of SEQ ID NO:31. The VL leader sequence corresponds to nucleotides 1-57 of SEQ ID NO:32. The 6×His-tag corresponds to nucleotides 742-759 of SEQ ID NO:31. The myc-tag corresponds to nucleotides 769-798 of SEQ ID NO:31. CDR sequences are underlined.

FIG. 3E shows nucleic acids sequences of the variable regions from heavy (VH) and light (VL) chains in PMS213. The VH leader sequence corresponds to nucleotides 1-66 of SEQ ID NO:35. The VL leader sequence corresponds to nucleotides 1-57 of SEQ ID NO:36. The 6×His-tag corresponds to nucleotides 742-759 of SEQ ID NO:35. The myc-tag corresponds to nucleotides 769-798 of SEQ ID NO:35. CDR sequences are underlined.

FIG. 3F shows VH and VL amino acid sequences of PMS209. The VH leader sequence (MKYLLPTAAAGLLL-LAAQPAMA; SEQ ID NO:40) corresponds to amino acids 1-22 of SEQ ID NO:21. The VL leader sequence (VKKLL-FAIPLVVPFYSHSA; SEQ ID NO:39) corresponds to amino acids 1-20 of SEQ ID NO:22. The 6×His-tag (HHHHHH: SEQ ID NO:18) corresponds to amino acids 252-257 of SEQ ID NO:21. The myc-tag (EQKLISEEDL; SEQ ID NO:17) corresponds to amino acids 261-270 of SEQ ID NO:21. CDR sequences are underlined. Asterisk stands for a stop codon.

FIG. 3G shows VH and VL amino acid sequences of PMS210. The VH leader sequence corresponds to amino acids 1-22 of SEQ ID NO:25. The VL leader sequence corresponds to amino acids 1-20 of SEQ ID NO:26. The 6×His— corresponds to amino acids 244-249 of SEQ ID NO:25. The myc-tag corresponds to amino acids 253-262 of SEQ ID NO:25. CDR sequences are underlined. Asterisk stands for a stop codon.

FIG. 3H shows VH and VL amino acid sequences of PMS211. The VH leader sequence corresponds to amino acids 1-22 of SEQ ID NO:29. The VL leader sequence corresponds to amino acids 1-20 of SEQ ID NO:30. The 6×His-tag corresponds to amino acids 245-250 of SEQ ID NO:29. The myc-tag corresponds to amino acids 254-263 of SEQ ID NO:29. CDR sequences are underlined. Asterisk stands for a stop codon.

FIG. 3I shows VH and VL amino acid sequences of PMS212. The VH leader sequence corresponds to amino acids 1-22 of SEQ ID NO:33. The VL leader sequence corresponds to amino acids 1-20 of SEQ ID NO:34. The 6×His-tag corresponds to amino acids 248-253 of SEQ ID NO:33. The myc-tag corresponds to amino acids 257-266 of SEQ ID NO:33. CDR sequences are underlined. Asterisk stands for a stop codon.

FIG. 3J shows VH and VL amino acid sequences of PMS213. The VH leader sequence corresponds to amino acids 1-22 of SEQ ID NO:37. The VL leader sequence corresponds to amino acids 1-20 of SEQ ID NO:38. The 6×His-tag corresponds to amino acids 248-253 of SEQ ID NO:37. The myc-tag corresponds to amino acids 257-266 of SEQ ID NO:37. CDR sequences are underlined. Asterisk stands for a stop codon.

FIG. 4A shows the nucleic acids sequence of PMS210 in full scFv-Fc format. The leader sequence (ATGAAA-CATCTGTGGTTCTTCCTTCTCCTGGTGGCAGCGG-CCCAGC; SEQ ID NO:16) corresponds to nucleotides 1-46 of SEQ ID NO:41. The VH sequence corresponds to nucleotides 52-705 of SEQ ID NO:41. The VL sequence corresponds to nucleotides 741-1,401 of SEQ ID NO:41. The linker (GGTGGCGGCGGTTCCG-GAGGTGGTGGTTCTGGCGGTGGTGGCAGC; SEQ ID NO:15) corresponds to nucleotides 706-750 of SEQ ID NO:41. The human IgG1 Fc tag corresponds to nucleotides 1,414-2,106 of SEQ ID NO:41 CDR sequences are underlined.

FIG. 4B shows the nucleic acids sequence of PMS212 in full scFv-Fc format. The leader sequence corresponds to nucleotides 1-46 of SEQ ID NO:43. The VH sequence corresponds to nucleotides 52-717 of SEQ ID NO:43. The VL sequence corresponds to nucleotides 763-1,410 of SEQ ID NO:43. The linker corresponds to nucleotides 718-762 of SEQ ID NO:43. The human IgG1 Fc tag corresponds to nucleotides 1,423-2,115 of SEQ ID NO:43. CDR sequences are underlined.

FIG. 4C shows amino acid sequence of PMS210 in full scFv-Fc format. The leader sequence (MKHLWFFLLL-VAAAQPA; SEQ ID NO:14) corresponds to amino acids 1-17 of SEQ ID NO:42. The VH sequence corresponds to amino acids 18-235 of SEQ ID NO:42. The VL sequence corresponds to amino acids 251-467 of SEQ ID NO:42. The linker (GGGGSGGGGSGGGGS; SEQ ID NO:47) corresponds to amino acids 236-250 of SEQ ID NO:42. The human IgG1 Fc tag corresponds to amino acids 471-702 of SEQ ID NO:42. CDR sequences are underlined. Asterisk stands for a stop codon.

FIG. 4D shows amino acid sequences of PMS212 in full scFv-Fc format. The leader sequence corresponds to amino acids 1-17 of SEQ ID NO:44. The VH sequence corresponds to amino acids 18-239 of SEQ ID NO:44. The VL sequence corresponds to amino acids 255-470 of SEQ ID NO:42. The linker corresponds to amino acids 240-254 of SEQ ID NO:44. The human IgG1 Fc tag corresponds to amino acids 474-705 of SEQ ID NO:44. CDR sequences are underlined. Asterisk stands for a stop codon.

Figures 5, 6:
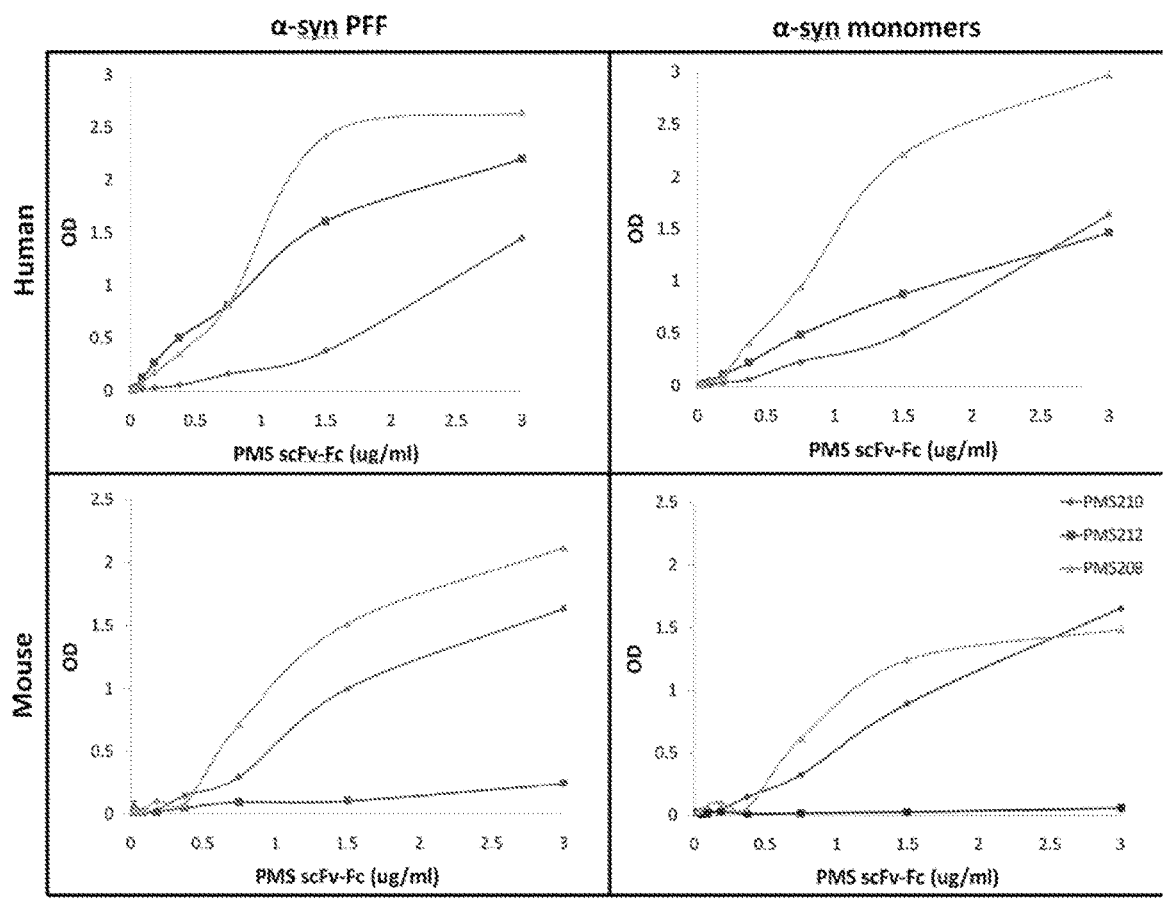

FIG. 5 shows high affinity binding of scFv-Fc PMS208 to PFF versus monomers in ELISA assay.

FIG. 6 shows high affinity binding of PMS208 (scFv form) to PFF and oligomers alpha synuclein in Surface Plasmon Resonance (Biacore). Association rate constant (Ka), dissociation rate constant (Kd) and affinity constant (KD) data are provided.

Figure 7A:
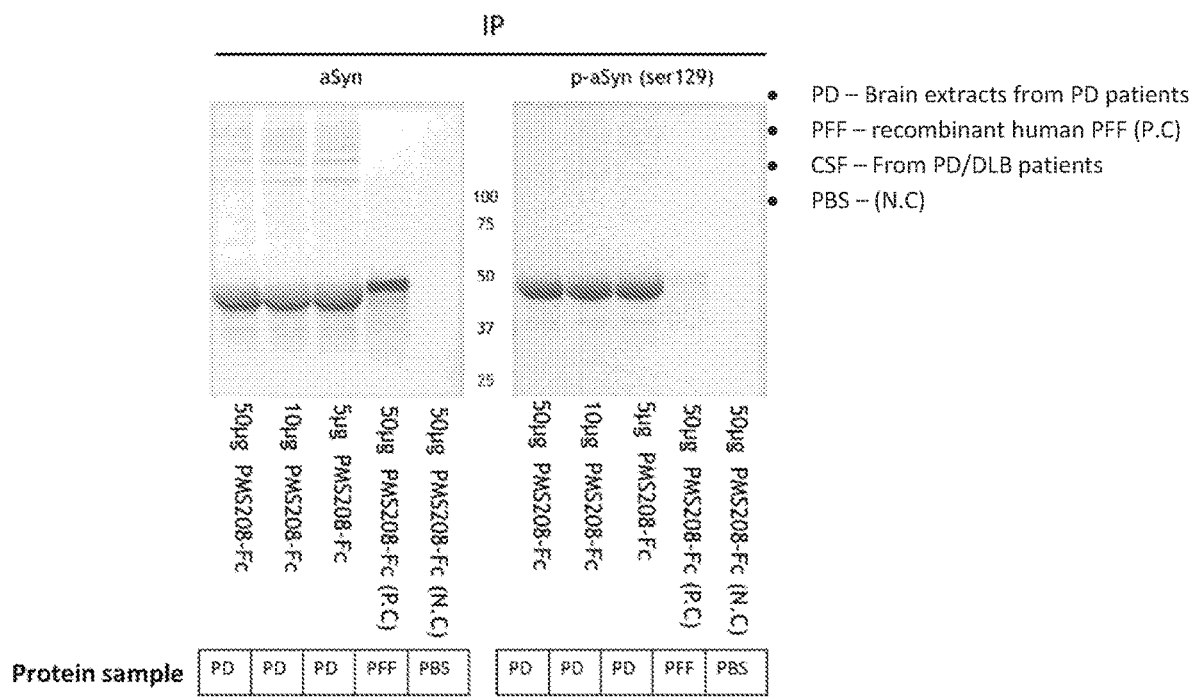
Figure 7B:
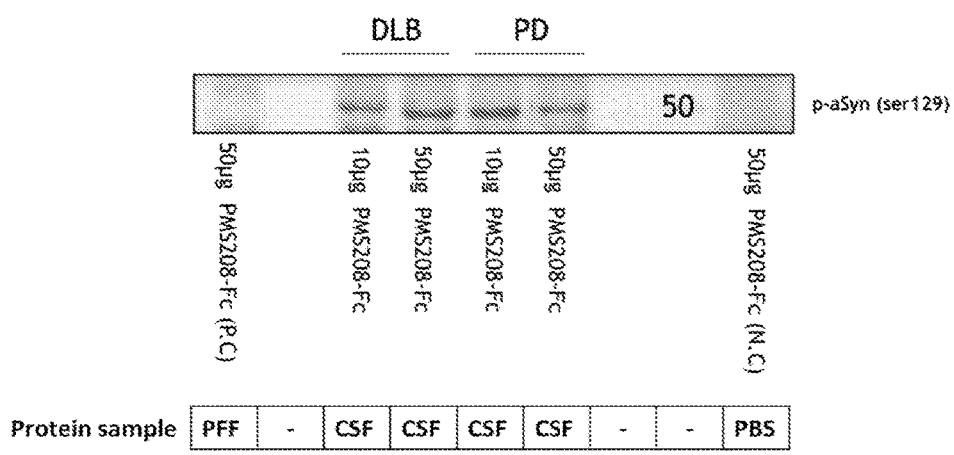

FIGS. 7A and 7B are images showing that PMS208 (scFv-Fc for immunoprecipitation) immunoprecipitates aSyn from PD patients sera (FIG. 7A) or PD/DLB patients CSF (FIG. 7B). FIG. 7A, Left panel—human alpha-synuclein staining using mouse monoclonal anti-human alpha-synuclein antibody (α-syn clone Syn 204 #838201, Biolegend (previously Covance catalog #MMS-530R)); FIG. 7A, Right Panel and FIG. 7B—phosphorylated human alpha-synuclein staining using mouse monoclonal anti-human phosphorylated alpha-synuclein in serine 129 (p-aSyn (ser129) (clone P-syn/81A #825701, Biolegend (previously Covance catalog #MMS-5091))).

Figure 8A:
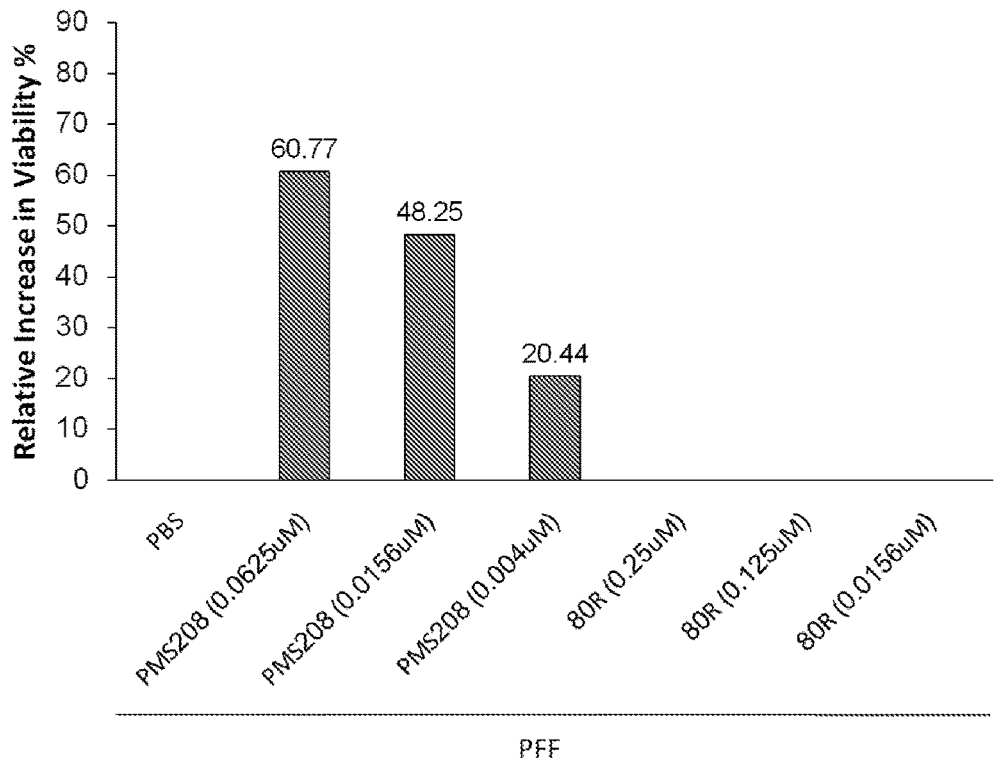
Figure 8B:
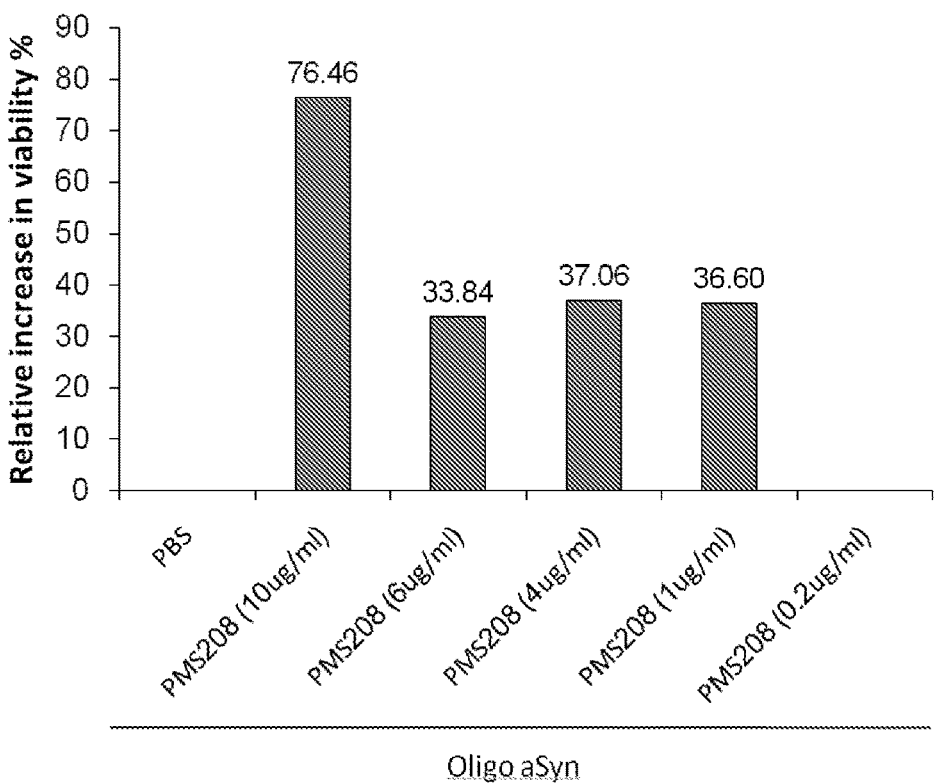
Figure 8C:
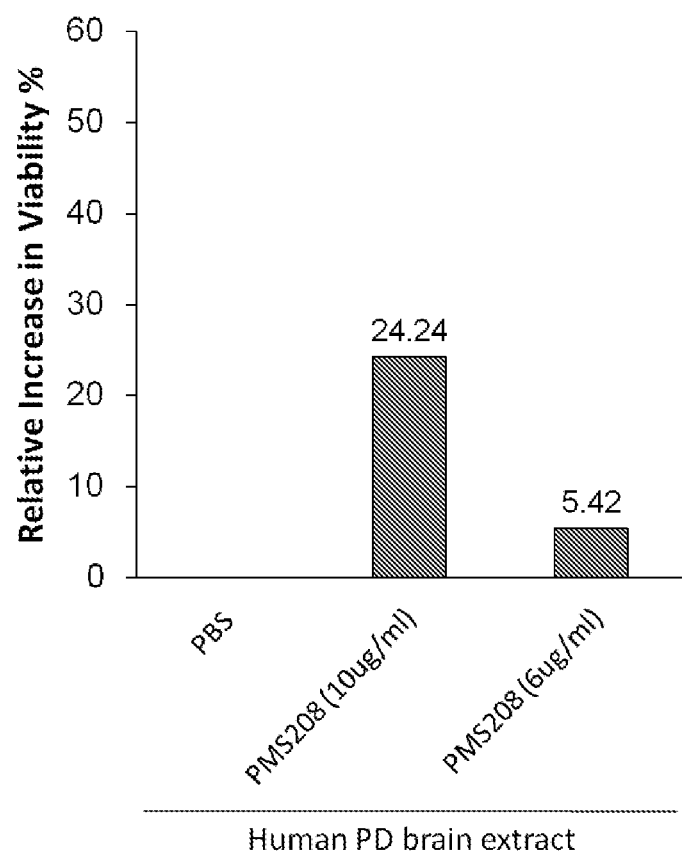

FIGS. 8A-C are bar graphs showing neuronal increase in viability mediated by PMS208 (scFv). PMS208 protects neuronal SH-SY5Y human cell line from α-syn PFF (FIG. 8A), oligomers (FIG. 8B), and human PD patient brain extracts (FIG. 8C). The y-axis represents the relative increase in cell viability compared to PFF/oligomers/human PD brain extracts with no treatment (PBS), PMS208 treatment, and 80R scFv isotype treatment (sham).

Figure 9A:
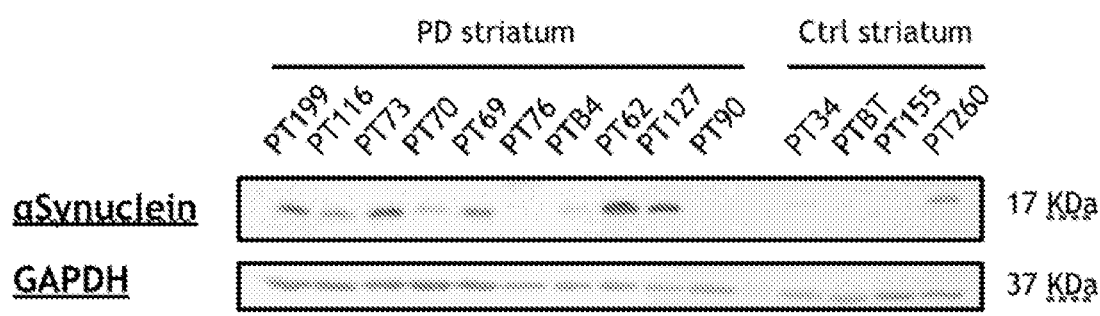
Figure 9B:
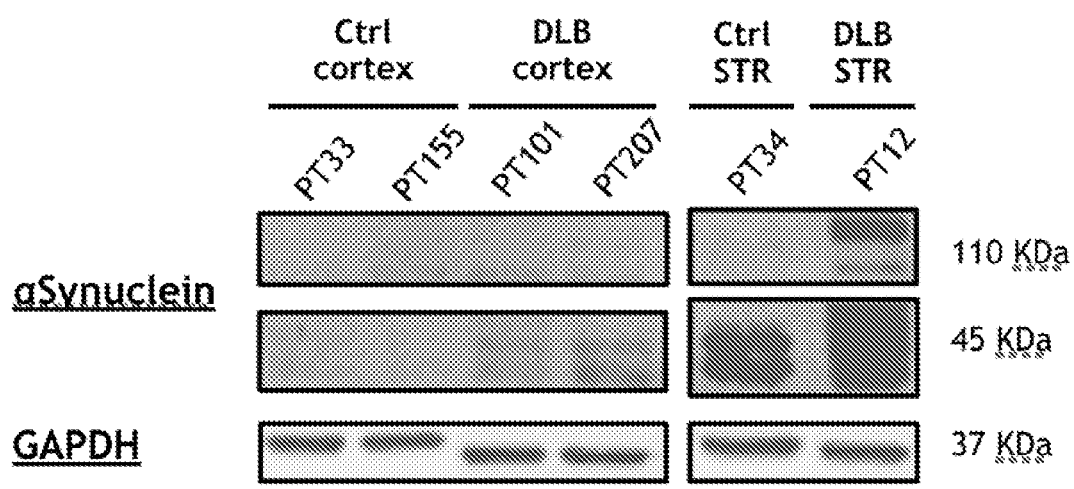
Figure 10A:
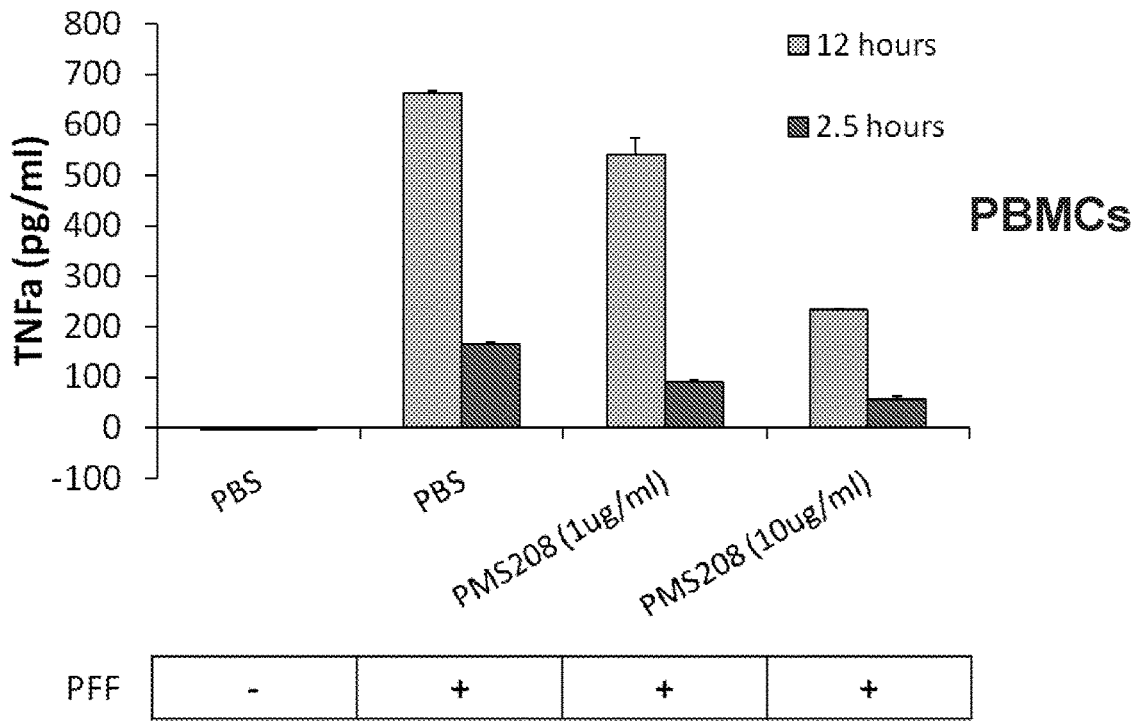
Figure 10B:
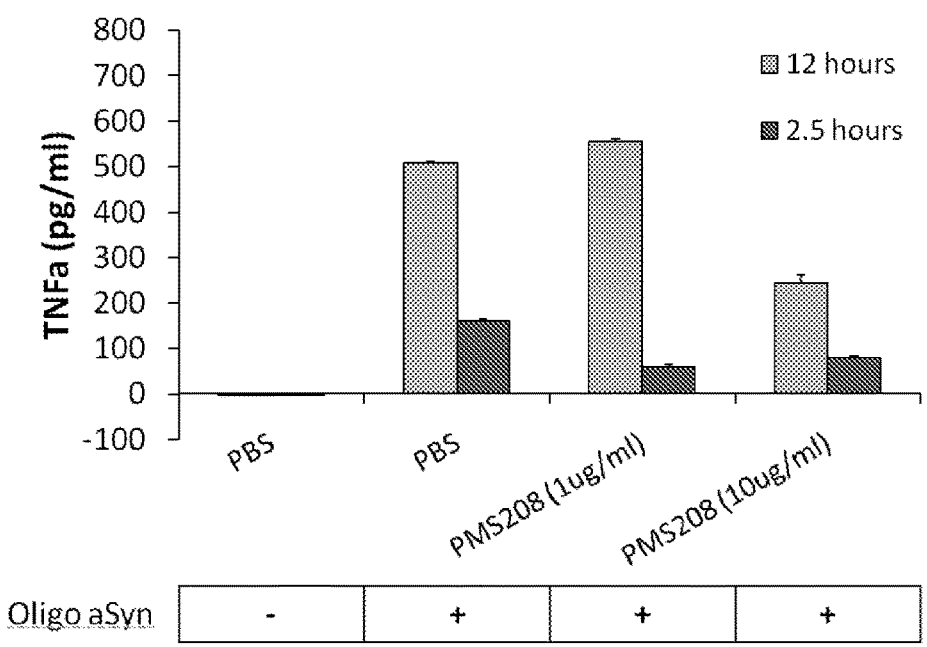
Figure 10D:
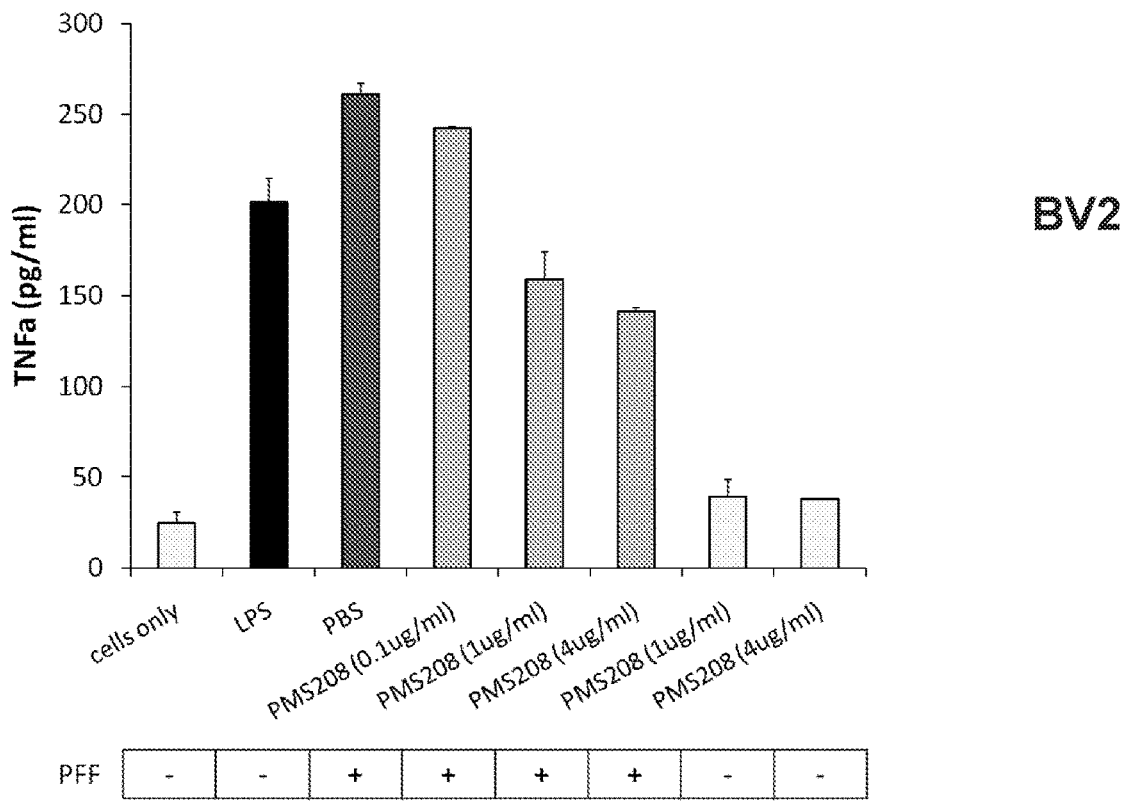
Figure 10E:
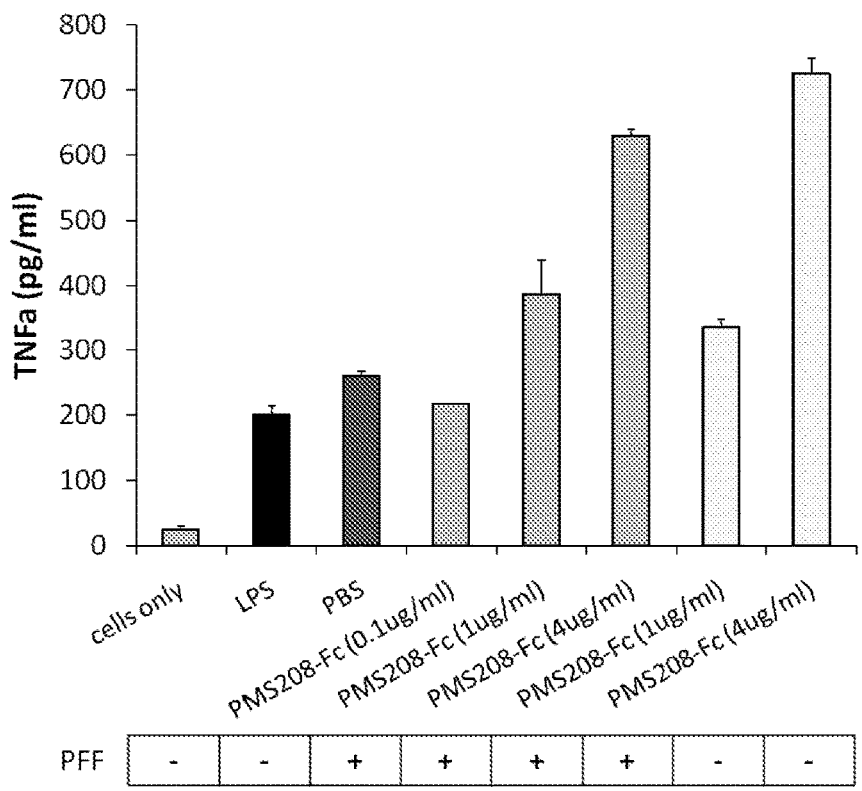
Figure 10F:
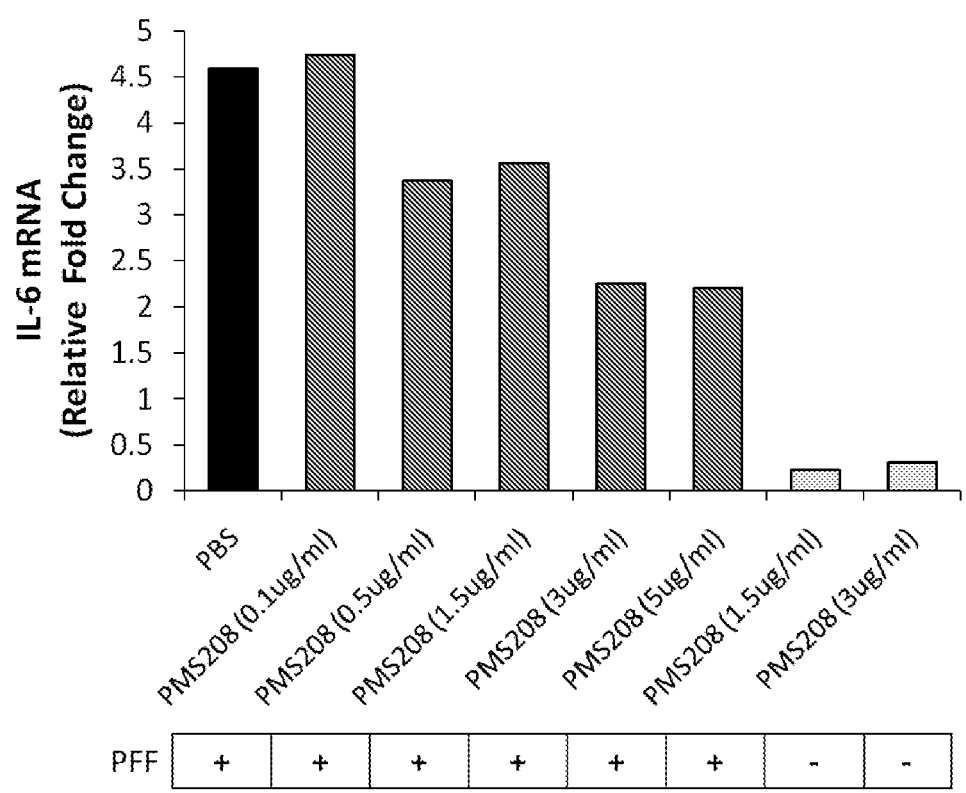

FIGS. 9A and 9B show Western blots of PMS208 binding to human striatum extracts from PD/control group patients (FIG. 9A) and PMS208 binding to human cortex (CTX) and striatum (STR—right panels) extracts of DLB and control group (Ctrl) patients (FIG. 9B). GAPDH as "housekeeping" protein loading control is shown in lower panels (FIGS. 9A and 9B).

FIGS. 10A-F are graphs showing that PMS208 attenuates neuroinflammation in human PBMCs (FIGS. 10A-C) and mouse microglia BV2 cells (FIGS. 10D and 10F) induced by PFF and oligomers. PBMCs were activated with PFF (FIG. 10A) and oligomers (FIG. 10B) for 2.5 hours or 12 hours to measure TNFα at the protein and mRNA (FIG. 10C) levels. In mouse microglia BV2 cells, PMS208 attenuates IL-6 mRNA levels (FIG. 10F) as well as TNFα protein levels compared to PMS208-Fc (FIGS. 10D and 10E) which has the opposing effect (elevates TNFα protein levels). Real-time PCR was done in cell homogenates. TNFα and IL-6 underwent TaqMan real-time PCR in cell homogenates. The y-axis represents the fold-change in expression compared to no treatment (cells only). GAPDH was used as "housekeeping" gene.

FIGS. 11A-F are graphs showing that PMS208 attenuates uptake of fluorescent PFF (PFF-488) in mouse peritoneal macrophages (FIG. 11A) and human PBMCs (FIG. 11B) in a dose dependent manner. PMS208 (FIGS. 11C and 11D) attenuates both PFF (FIGS. 11C and 11E) and oligomers (FIGS. 12D and F) compared to PMS208-Fc (FIGS. 11E and 11F) in microglia cells (BV2). The y-axis represents the relative geometric mean (gMFI) measured by flow cytometry.

Figure 12A:
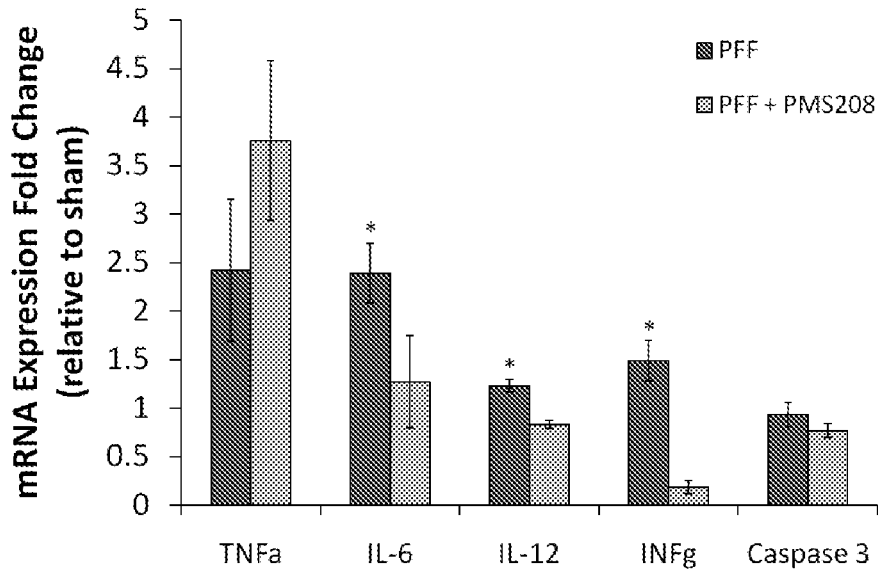
Figure 12B:
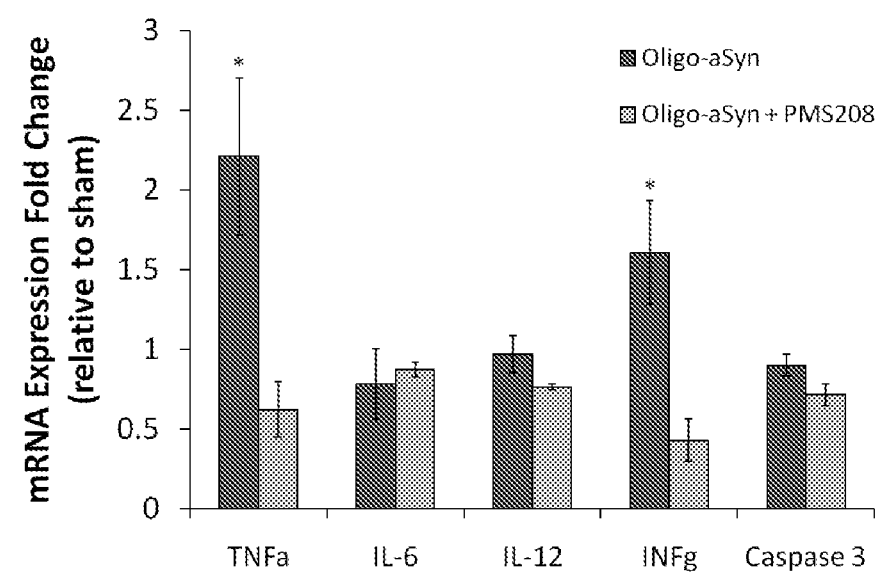
Figure 12C:
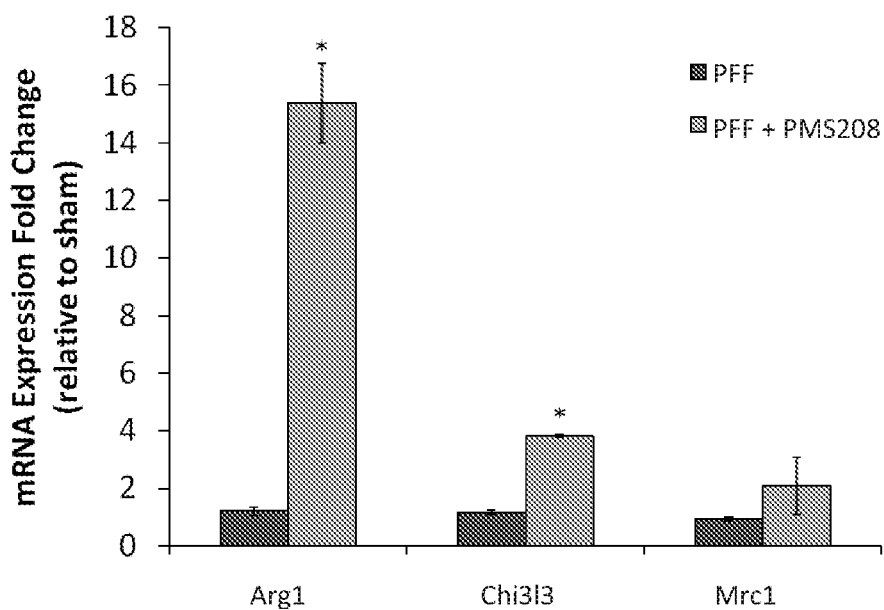
Figure 12D:
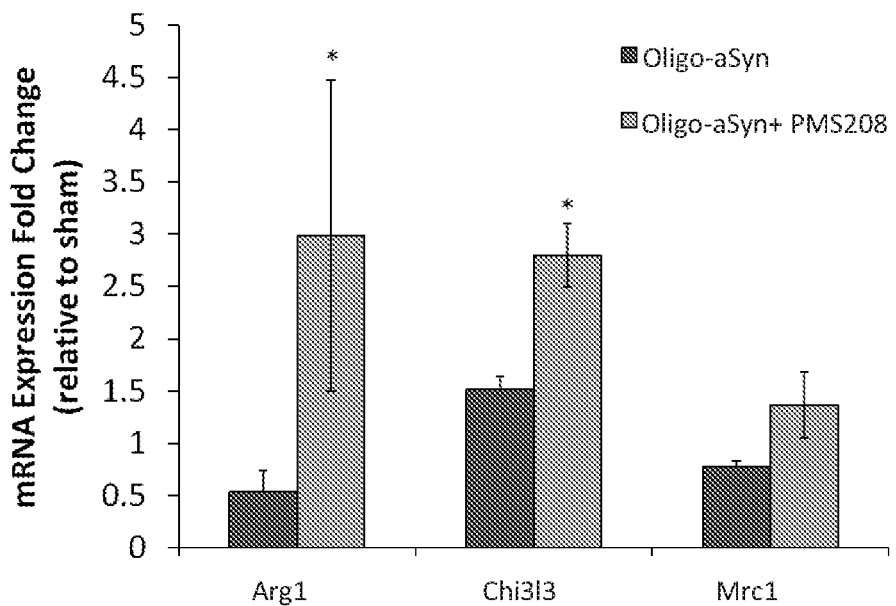

FIGS. 12A-D are graphs showing that PMS208 attenuates neuroinflammation in murine cortex of animals injected (striatum) with PFF (FIGS. 12A and 12C) and oligomers (FIGS. 12B and 12D). Real-time PCR was done in brain cortexes homogenates. The expression of TNFa, IL-6, IL-12, INFγ, Caspase 3, Arg1, Chi3l3, and Mrc1 was determined by TaqMan real-time PCR in brain homogenates. The y-axis represents the fold-change in expression after PFF intrastriatal injections (with and without PMS208 treatment). GAPDH was used as "housekeeping" gene. $*p<0.05$, n=3.

Figure 13A:
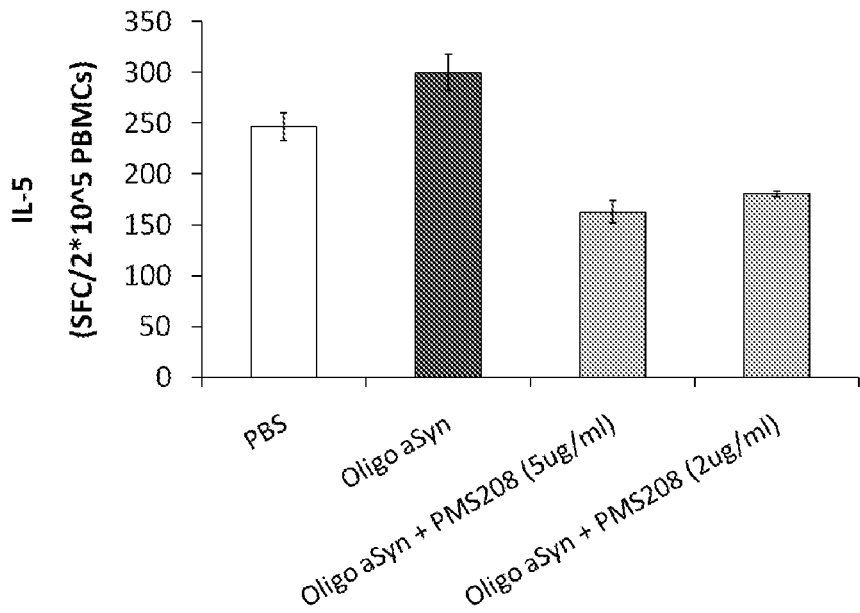
Figure 13B:
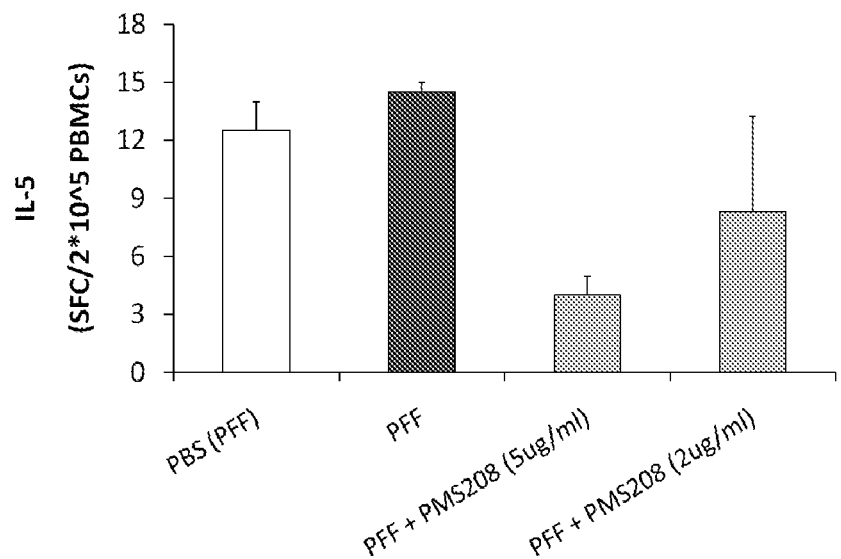
Figure 13C:
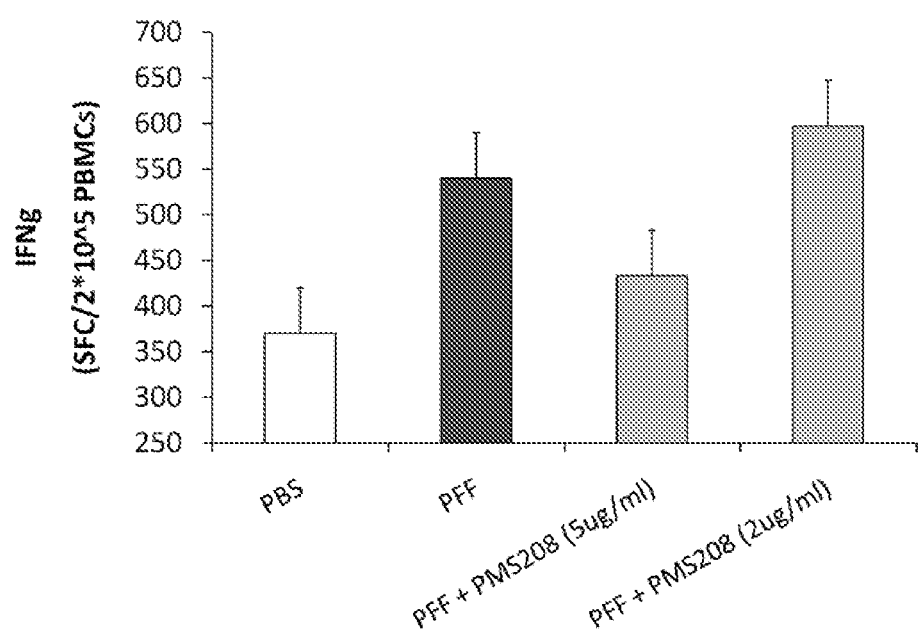

FIGS. 13A-C are graphs showing reactivity to α-syn toxic forms in patients with Parkinson's disease as measured by the magnitude of autoimmune responses against α-syn PFF and oligomers as SFC (spot forming cells) per $10^5$ PBMCs. FIGS. 13A and 13B show IL-5 responses, and FIG. 13C shows IFNγ responses of different PD patients. PMS208 manages to tune down the autoimmune response of T cells to α-syn pff and oligomers. Images are representative of a number of repeats in different PD patients.

Figure 14:
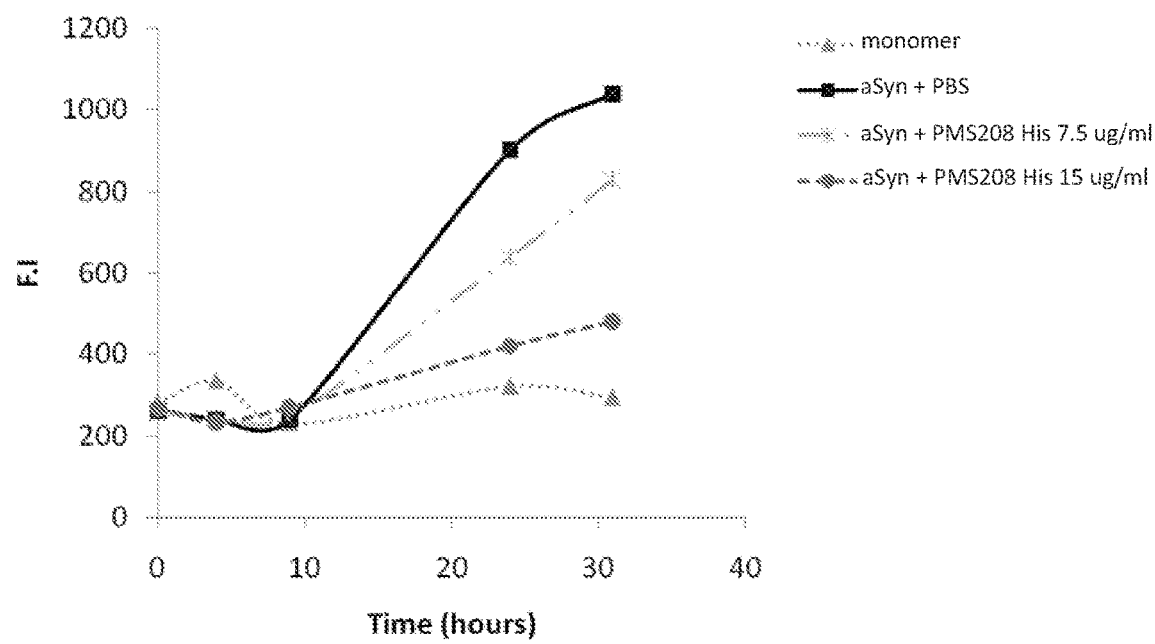

FIG. 14 is a graph showing kinetics for the formation of β-sheet-rich assemblies: human α-syn PFF incubated with PMS208 (7.5 ug/ml or 15 ug/ml) versus PBS (black solid line). Monomers (dotted line marked with triangles) were measured as baseline.

Figure 15:
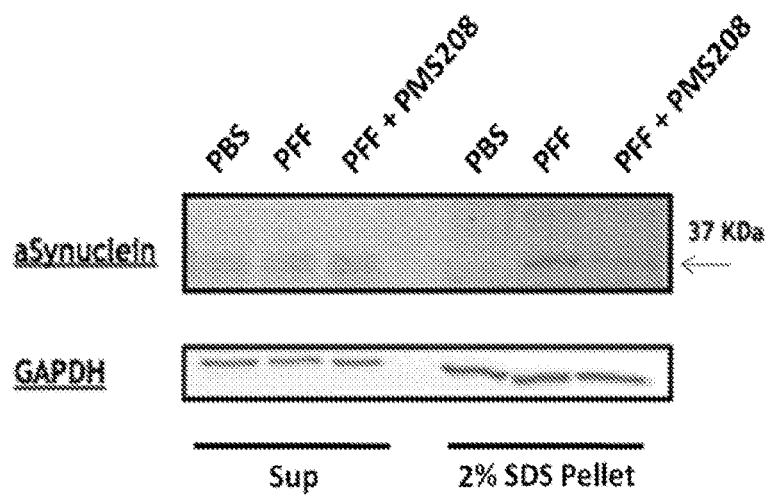

FIG. 15 shows a Western blot following sequential extraction of neurons in 1% (vol/vol) TX-100 followed by SDS. Immunoblotting was performed using rabbit anti-rodent alpha-synuclein, an antibody that recognizes endogenous total α-syn (upper panel) and mouse anti-GAPDH (lower panel). In PFF-treated neurons, there was an increase in SDS-soluble α-syn (2% SDS) compared to PBS or PFF+ PMS208 treated neurons (arrow).

Figure 16A:
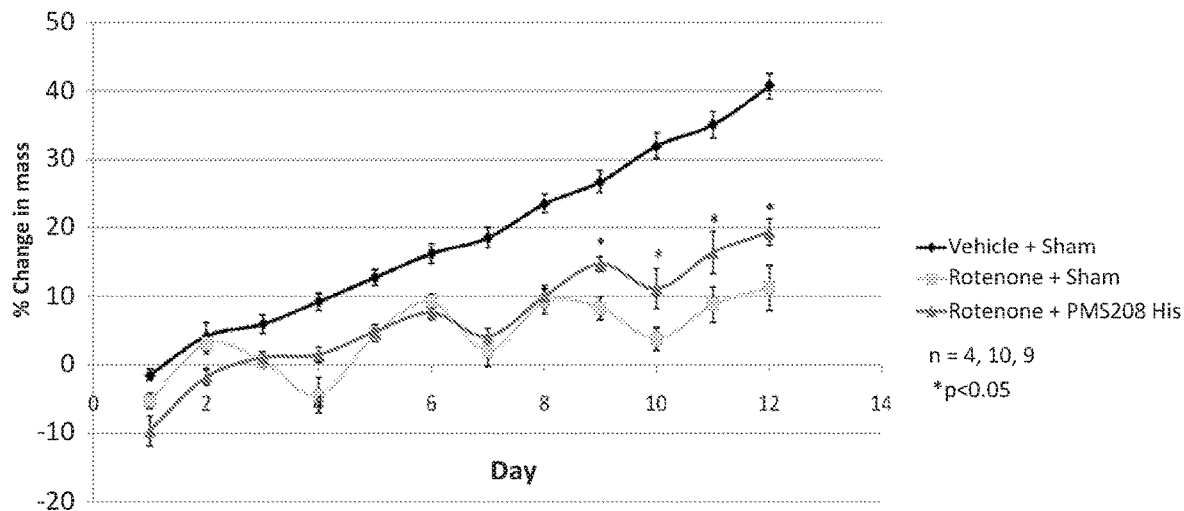
Figure 16B:
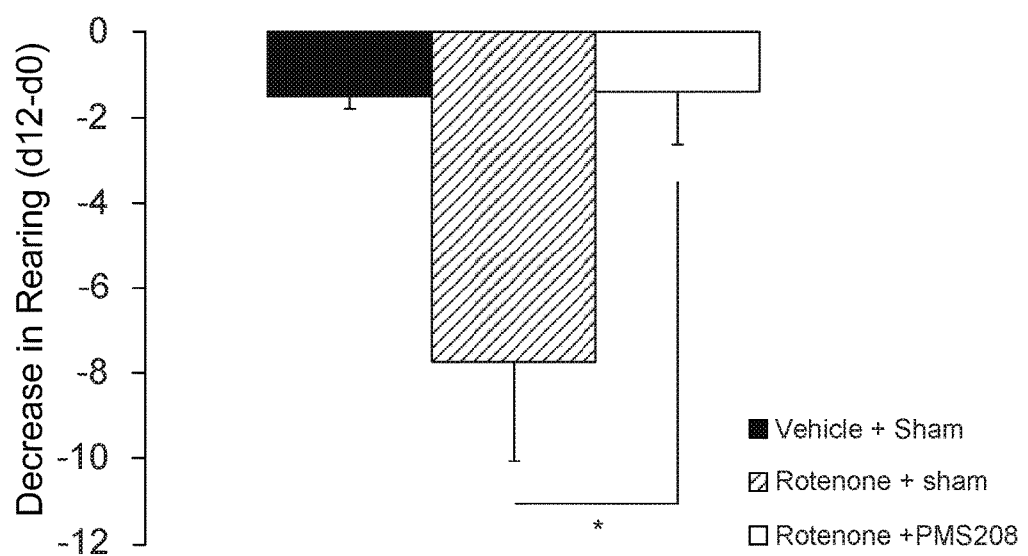

FIGS. 16A and 16B show that daily intraperitoneal rotenone elicits moderate weight loss and a parkinsonian phenotype that is alleviated by intranasal PMS208. FIG. 16A shows the percent change in mass from day 0 in 2 months old rats treated with rotenone (Rotenone+Sham, n=10), rotenone with PMS208 treatment (Rotenone+PMS208, n=9), and control rats (Vehicle+Sham, n=4). Rotenone was administered at increasing concentrations (day 0 with 1.5 mg/kg/day, day 3 with 2 mg/kg/day and day 6 with 2.5 mg/kg/day). FIG. 16B shows the number of rears in rats was quantified (Rotenone+Sham; Rotenone+PMS208; Vehicle+ Sham). The animal had to raise forelimbs above shoulder level and make contact with the cylinder wall with either one or both forelimbs in order to be classified as a rear. Removal of both forelimbs from the cylinder wall and contact with the table surface was required before another. Animals were euthanized when severe parkinsonian symptoms developed. Mortality occurring immediately after the injection (in the absence of parkinsonian symptoms and typically<10%) was excluded from analysis. $*p<0.05$. Error bars represent standard error of the mean.

Figure 17A:
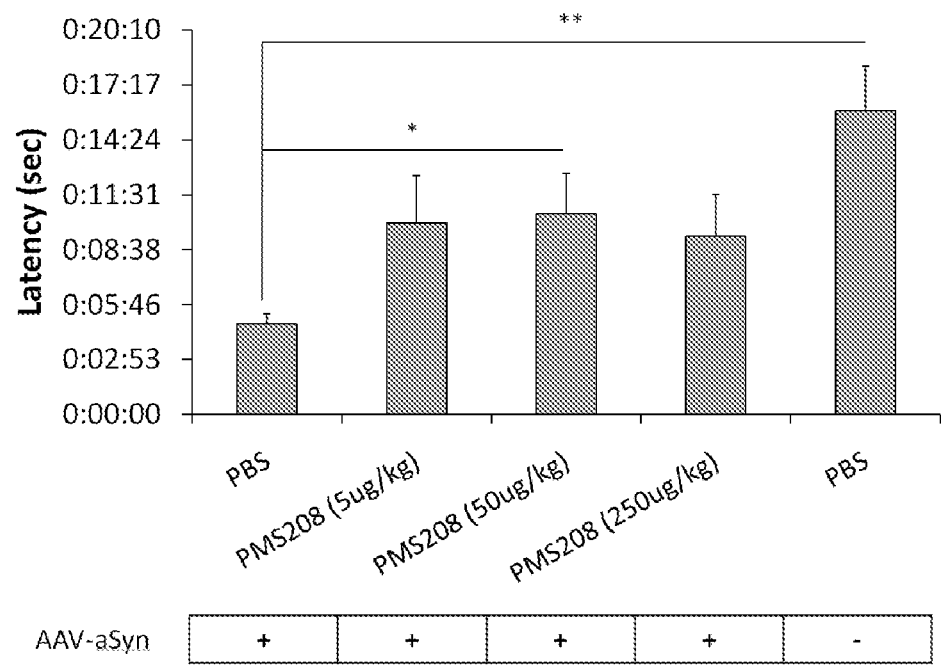
Figure 17B:
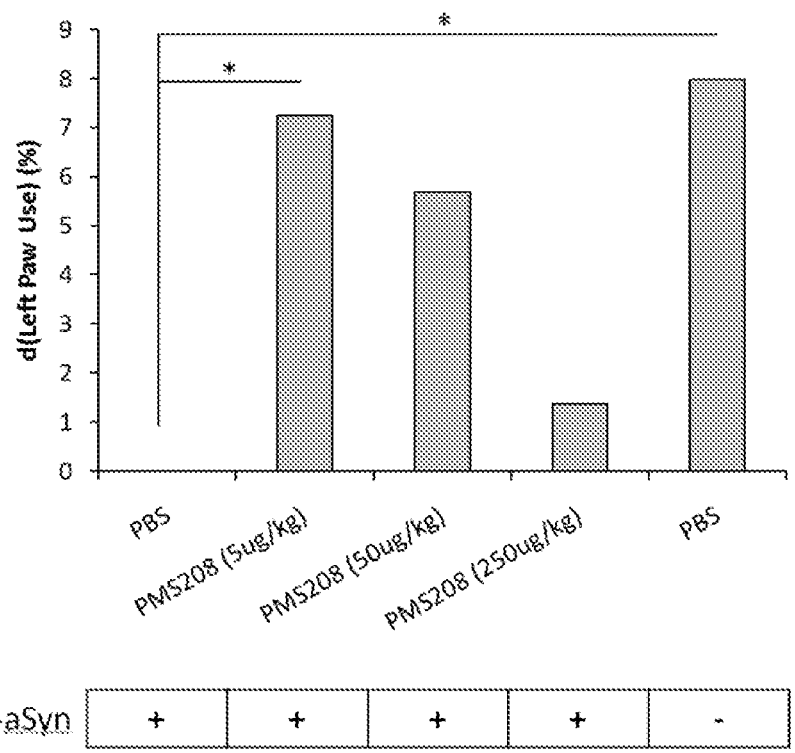

FIGS. 17A and 17B show that PMS208 given intranasally (IN) attenuates motor dysfunction induced by intracerebral injections of adeno associated virus expressing human aSyn (AAV-aSyn) in rats. rAAV2/DJ vector-mediated α-synuclein overexpression in mouse SN leads to motor behaviour impairments. (FIG. 17A) Neuromuscular strength was tested with the two limb wire hang test 6 weeks after injection. Each rat was tested three times and the top two results were used for analysis. (FIG. 17B) Performance in the cylinder test of rAAV2/DJ-α-synuclein VS sham mice at 5-6 weeks after injection. At 5-6 weeks after injection, a significantly reduced use of the contralateral forepaw was observed for α-synuclein vector compared to the sham and intranasal treatment groups. For all tests: n=7. $*p<0.05$, $**p<0.01$. Error bars represent standard error of the mean.

Figure 18A:
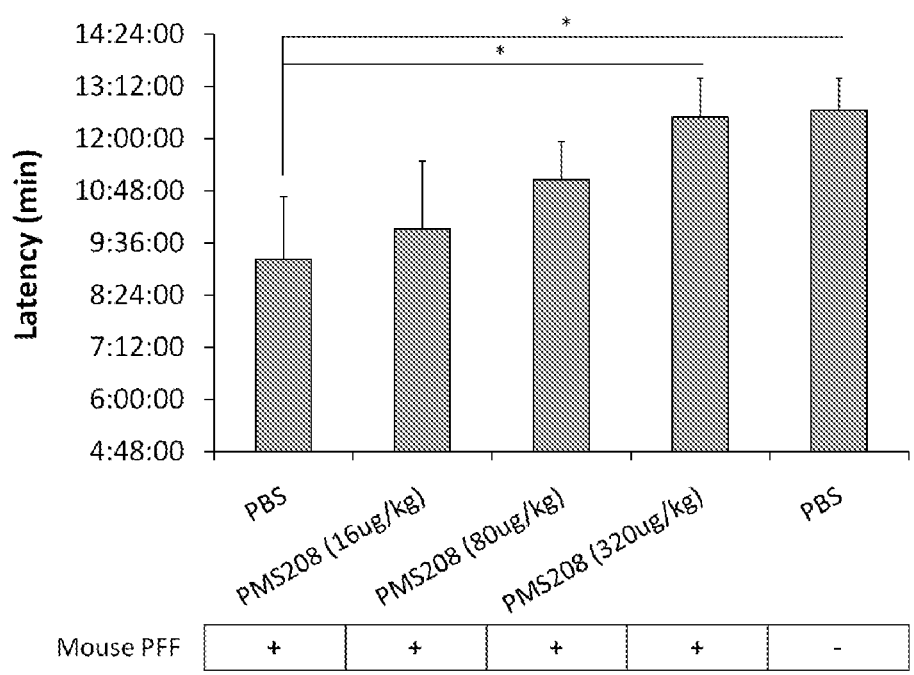
Figure 18B:
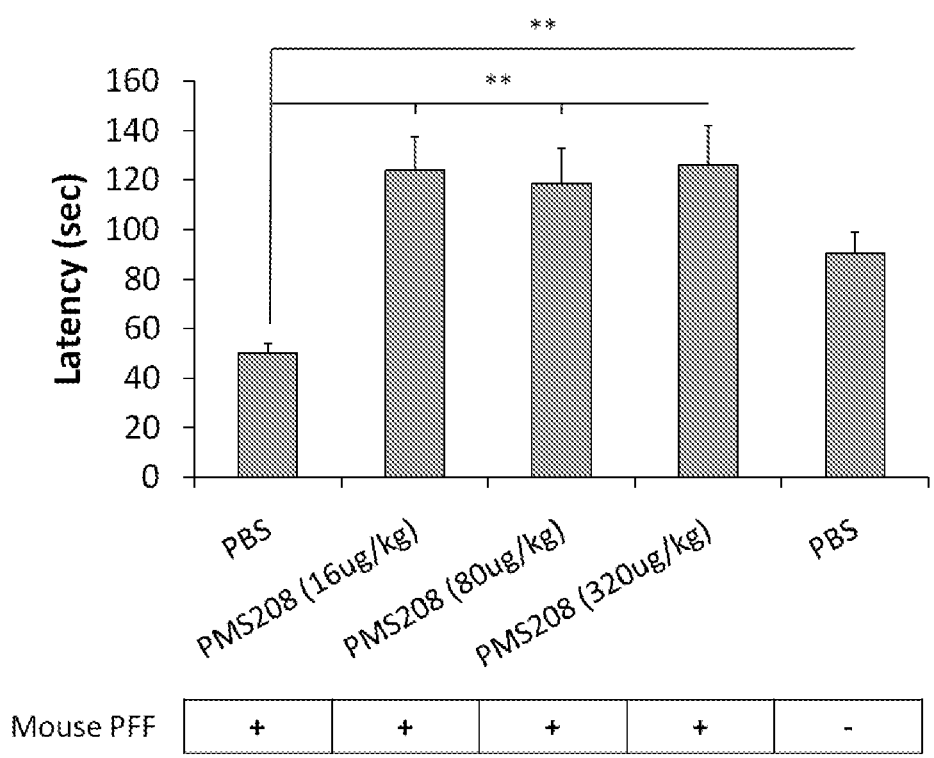
Figure 18C:
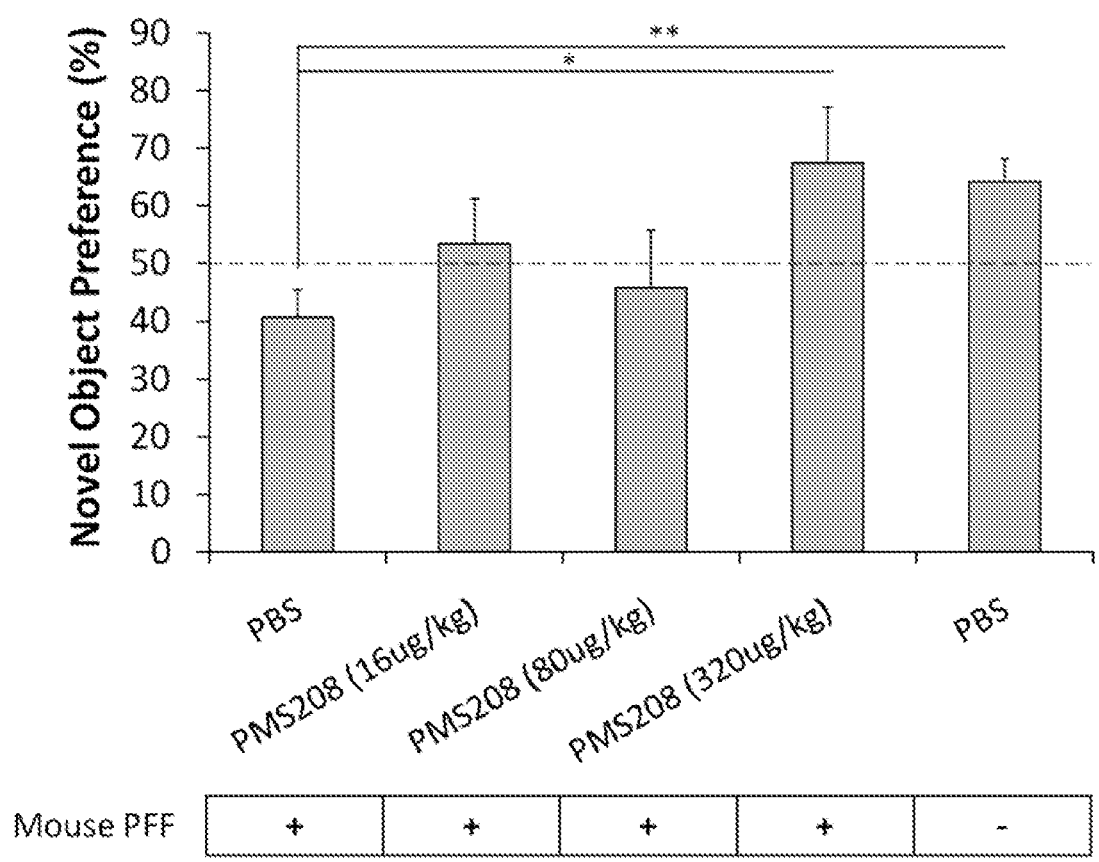

FIGS. 18A-C show that mouse alpha-synuclein PFF intrastriatal injections in mice leads to motor behavior and cognitive impairments. FIG. 18A shows a neuromuscular strength assessment using a wire hang test performed at 12 weeks after injection. Mouse PFF injected group compared to sham and intranasal treatment groups (16, 80, 320 ug/kg) showed a significant reduction in average time of animals latency to fall. Each mouse was tested three times, and the top two results were used for analysis. FIG. 18B demonstrates that the rotarod test performed at 12 weeks after injection showed a significant reduction in average time on the rotating rod for the mouse PFF injected group compared to the sham and intranasal treatment groups (16, 80, 320 ug/kg). FIG. 18C shows the mean novel object preference for all mice groups during the testing phase when one familiar object and one novel object were presented to mice is shown. n=9, 10, 9, 9, 9; *p<0.05, **p<0.002. Error bars represent standard error of the mean.

Figure 19:
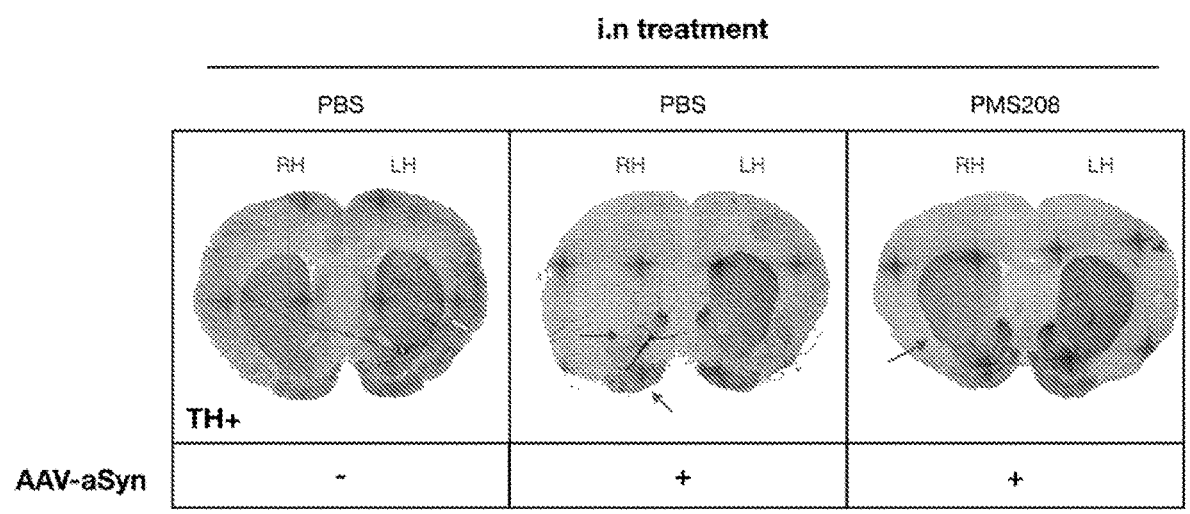

FIG. 19 shows brain sections of animals injected with adeno-associated virus expressing human aSyn (AAV-aSyn) that develop extensive and significantly greater loss of TH+ and dopaminergic (DA)neurons and the effect of PMS208 thereon.

DESCRIPTION OF SPECIFIC EMBODIMENTS OF THE INVENTION

The present invention, in some embodiments thereof, relates to antibodies and antigen-binding fragments thereof for the treatment of synucleinopathies and neuroinflammation.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Alpha-synuclein (α-syn) plays a pivotal role in the pathogenesis of Parkinson's Disease (PD) and other synucleinopathies. Two forms of α-syn are believed to promote neurotoxicity, spreading, and neuroinflammation; these are small molecular oligomers and preformed fibrils (PFF).

Whilst conceiving the invention, the present inventors have searched for a biological agent that would target the small molecular oligomers and preformed fibrils of alpha-synuclein and be sufficiently small to facilitate effective entry to the brain without requiring high systemic dosages and avoiding non specific Fc portion-related immune-mediated effects.

Thus, the present inventors have isolated from human phage display libraries of healthy individuals, a panel of Fabs, of which PMS208, was cloned into a single chain Fv. A plasmid encoding PMS208 was deposited with the American Type Culture Collection (ATCC), located at 10801 University Boulevard, Manassas, Va. 20110 on Mar. 14, 2018, under the terms of the Budapest Treaty and has the ATCC® Deposit Designation PTA-125004.

This antibody fragment was selected based on a complex screening that included the following selection criteria: binding to native alpha-synuclein in patients' sera, binding the denatured form of the protein as well as the native form (rendering it superior for both clinic and research), preventing recruitment of the immune system to the damaged area, reduction of neuro-inflammation, prevention of seeding and spreading, prevention of immune cells activation, prevention of alpha-synuclein aggregation (as determined by Thioflavin T (ThT), as well as disintegration of preformed aggregates and efficacy in vivo in animal models.

The Fab was cloned into a smaller scFv format with successful retention of its affinity. Importantly and uniquely, PMS208 binds with high affinity both α-syn oligomers and PFF. PMS208 attenuates toxicity induced by both oligomers and PFF to human and murine neuronal cells and binds avidly to α-syn in brain extracts from PD patients. Importantly, the scFv form of PMS208 down-regulates a panel of pro-inflammatory cytokines produced by microglia after exposure to oligomers and PFF, whereas Fc containing anti-α-syn antibodies up-regulate this same panel of proteins. Intranasal PMS208 administration attenuates motor dysfunction in a number of PD animal models in vivo, demonstrating that relatively low doses of PMS208 are required.

The size of the scFv that still retains the high affinity is one sixth the size of an IgG, which explains its bioavailability and efficacy via the intranasal route (mainly via the olfactory nerve). This delivery mode reduces the need to achieve high systemic levels as is currently attempted with immunotherapy for neurodegenerative diseases.

Thus, according to an aspect of the invention there is provided an isolated antibody comprising an antigen binding domain comprising CDR sequences which are N—C ordered:

| Heavy Chain PMS208 | SEQ ID NO: | SEQUENCE: |
|---|---|---|
| CDR1 HC | 1 | GGSISSHY |
| CDR2 HC | 2 | IYDSGST |
| CDR3 HC | 3 | ARGAGWYRF |
| Light Chain PMS208 | SEQ ID NO: | SEQUENCE: |
| CDR1 LC | 4 | QSVLYSSNNKNY |
| CDR2 LC | 5 | WAS |
| CDR3 LC | 6 | QQYYSTPRT | wherein said antibody is capable of binding to soluble monomers, oligomers, and/or preformed fibrils (PFF) of alpha-synuclein in an affinity that is below 10 nM, as determined by surface plasmon resonance.

According to another aspect of the invention there is provided an isolated antibody comprising an antigen binding domain comprising CDR sequences which are N—C ordered:

| Heavy Chain PMS208 | SEQ ID NO: | SEQUENCE: |
|---|---|---|
| CDR1 HC | 50 | SHYWS |
| CDR2 HC | 51 | YIYDSGSTNYNPSLKS |
| CDR3 HC | 52 | GAGWYRF |
| Light Chain PMS208 | SEQ ID NO: | SEQUENCE: |
| CDR1 LC | 53 | KSSQSVLYSSNNKNYLA |
| CDR2 LC | 54 | WASTRES |
| CDR3 LC | 55 | QQYYSTPRT | wherein said antibody is capable of binding to soluble monomers, oligomers, and/or preformed fibrils (PFF) of alpha-synuclein in an affinity that is below 10 nM, as determined by surface plasmon resonance.

The CDR sequences can be encoded by the following polynucleotide sequences.

| Heavy Chain PMS208 | SEQ ID NO: | SEQUENCE: |
|---|---|---|
| CDR1 HC | 7 | GGCGGCTCTATCAGCAGCCACTAC |
| CDR2 HC | 8 | ATCTACGACAGCGGCAGCACC |
| CDR3 HC | 9 | GCTAGAGGCGCCGGA TGGTACAGATTT |

| Light Chain PMS208 | SEQ ID NO: | SEQUENCE: |
|---|---|---|
| CDR1 LC | 10 | CAGAGCGTGCTGTACTCC AGCAACAACAAGAACTAC |
| CDR2 LC | 11 | TGGGCCAGC |
| CDR3 LC | 12 | CAGCAGTACTACAGCACC CCTCGGACC |

The terms "alpha-synuclein," "α-synuclein," "a-synuclein," "aSyn," "αSyn," "a-Syn," and "α-Syn" are used interchangeably herein. Aliases for alpha-synuclein include, e.g., SNCA, NACP, PARK1, PARK4, PD1, synuclein alpha. These terms include human alpha-synuclein as well as non-human alpha-synuclein. These terms also include soluble monomers, oligomers, and/or preformed fibrils of alpha-synuclein.

As used herein "human alpha-synuclein" refers to the protein product of the SNCA gene with the UniProt identification P37840:

(SEQ ID NO: 13)
MDVFMKGLSKAKEGVVAAAEKTKQGVAEAAGKTKEGVLYVGSKT

KEGVVHGVATVAEKTKEQVTNVGGAVVTGVTAVAQKTVEGAGSI

AAATGFVKKDQLGKNEEGAPQE GILEDMPVDP DNEAYEMPSE

EGYQDYEPEA.

Also contemplated herein are non-human forms of the "alpha-synuclein" e.g., mouse alpha-synuclein to which an antibody or antigen-binding fragment thereof according to some embodiments of the invention (e.g., PMS208) can bind rendering it a pan-species antibody antigen-binding fragment that is very useful in research and pre-clinical studies.

The molecular weight of human alpha-synuclein monomers is 14 kDa. Two or more alpha-synuclein monomers can aggregate and form soluble alpha-synuclein protofibrils/oligomers with a wide range of molecular weights. A dominating oligomer typically has a molecular weight of 28 kDa. Higher weight forms, e.g., 2000 kDa, are typically referred to as a preformed protofibril (PFF). The major difference between oligomers and PFF is in the morphology, which is visible under an electron microscope (oligomers are round and small, while PFFs are fibril shaped), and the weight can be determined by size exclusion chromatography and SDS-PAGE analysis (non-reduced or native).

According to a specific embodiment, the oligomer is of the molecular weight of 14-84 kDa, as determined by electron microscope and/or size exclusion chromatography.

Purified α-syn monomers are available commercially such as from Alexotech, Sweden.

Preparation of higher orders of alpha-synuclein can be done by aldehyde induction for the preparation of oligomers. PFF can be induced by incubating monomers at 37° C. for 7 days at 1000 rpm.

Specifically, purified α-syn monomer (in PBS, pH 7.4) are mixed together with HNE (4-Hydroxynonenal) 20 mg/ml (in DMSO) in a low binding tube (e.g., Protein LoBind Tube 1.5, Eppendorf tubes, Cat no.: 022431081) for a final concentration of 140 µM α-syn and 4200 µM HNE. Samples are incubated at 37° C. for 18 hours (h) and analyzed in SDS-PAGE, silver stain (manufacture protocol). Alpha-Syn adopts an extended conformation oligomeric form (spherical—monomers to hexamers), with dimers being the major species (SDS resistant). Of note, oligomers and PFF can overlap in the size but not in the structure (round vs. fibril)

Each form can be produced by a different reaction (HNE or incubation in 37° C. for 7 days at 1000 rpm), which was verified with electron microscope and SDS-PAGE analysis.

According to a specific embodiment, the antibody or antigen-binding fragment thereof binds the PFF in a higher affinity than to α-synuclein oligomers or even monomers. e.g., 0.67 nM PFF compared to 3.46 nM (~5 fold) oligomers as determined by SPA.

As used herein, "higher affinity" refers to an affinity which is at least 2-fold (e.g., 2.5, 3, 3.5, 4, 4.5, 5, 5.5, 6, 6.5, 7, 7.5, 8, 8.5, 9 and even 10 and above fold) higher (lower $K_D$).

As used herein "binding" or "binds" refers to an antibody-antigen mode of binding, which is generally, in the case of clinically relevant antibodies or antigen-binding fragments thereof, and in this case in the range of $K_D$ below 10 nM e.g., about 0.5-0.7 nM, e.g., 0.67 nM at the conditions described in the Examples section, as determined by Surface Plasmon Resonance assay (SPR), when binding to PFF, or 2-5 nM, e.g., 3.46 nM, when binding to the oligomers.

The affinity of the antibody or antigen-binding fragment to its antigen is determined by Surface Plasmon Resonance (SPR) using a captured or immobilized antigen. For instance, in one embodiment the antigen is immobilized when the antibody or antigen-binding fragment (e.g., scFv) (table) is tested and in another embodiment the antibody or antigen-binding fragment (e.g., scFv-Fc) is immobilized and the antigen is in the solution.

As used herein the term "$K_D$" refers to the equilibrium dissociation constant between the antigen binding domain or the antibody or antigen-binding fragment thereof and its respective antigen.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain an antigen recognition site of an intact antibody (e.g., complementarity determining regions (CDRs) sufficient to bind antigen). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The terms "alpha-synuclein antibody" and "antibody that binds to alpha-synuclein" refer to an antibody that is capable of binding alpha-synuclein (in soluble monomer, oligomer, and/or preformed fibril forms) with sufficient affinity such that the antibody is useful as a diagnostic and/or therapeutic agent in targeting alpha-synuclein. The extent of binding of an alpha-synuclein antibody to an unrelated, non-alpha-synuclein protein can be less than about 10% of the binding of the antibody to alpha-synuclein as measured, e.g., by a radioimmunoassay (RIA).

In some embodiments, the isotype of an antibody or antigen-binding fragment thereof is selected from IgG1, IgG2, IgG3, and IgG4, more particularly, IgG1 or IgG4. According to a specific embodiment, the isotype is IgG1.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that CDRs of the light and heavy chains are primarily responsible for the interaction and specificity of the antibody with antigen. In certain aspects, the variable region is a human variable region.

The terms "VH" and "VH domain" are used interchangeably to refer to the heavy chain variable region of an antibody or antigen-binding fragment thereof.

The terms "VL" and "VL domain" are used interchangeably to refer to the light chain variable region of an antibody or antigen-binding fragment thereof.

As provided herein, the polypeptides of an antibody or antigen-binding fragment thereof (e.g., a VH, VL, heavy chain, light chain, and/or scFv) can be expressed with a leader sequence or signal sequence, which is cleaved during intracellular processing to produce a "mature" polypeptide. The "mature" forms of the polypeptides do not contain the leader or signal sequences. For example, the "mature form" of the polypeptide of SEQ ID NO:21 comprises amino acids 23-274 of SEQ ID NO:21.

As used herein, the terms "complementarity-determining region" or "CDR" are used interchangeably to refer to the antigen binding regions found within the variable region of the heavy and light chain polypeptides. Generally, antibodies or antigen-binding fragments thereof comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody or antigen-binding fragment thereof that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Wash. D.C.), location of the structural loop regions as defined by Chothia et al. (see, e.g., Chothia et aL, Nature 342:877-883, 1989), a compromise between Kabat and Chothia using Oxford Molecular's AbM antibody modeling software (now Accelrys®, see, Martin et al, 1989, Proc. Natl Acad Sci USA. 86:9268; and world wide web site www.bioinf-org.uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008; IMGT unique numbering for V-DOMAIN and V-LIKE-DOMAIN; lefranc numbering, Lefranc M.-P. et al., 1997).

As used herein, the "variable regions" and "CDRs" may refer to variable regions and CDRs defined by any approach known in the art, including combinations of approaches.

According to a specific embodiment, the antibody fragment is selected from the group consisting of single chain, $F_{ab}$, $F_{ab'}$, and $F_{(ab')2}$ fragments, Fv, dsFv, scFvs, diabodies, minibodies, nanobodies, $F_{ab}$ expression library or single domain molecules such as VH and VL that are capable of binding the antigen as described hereinabove.

According to a specific embodiment, the antibody fragment is an intrabody. The intrabody can comprise an scFv and an intracellular trafficking signal.

Functional antibody fragments comprising whole or essentially whole variable regions of both light and heavy chains some of which are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

According to a specific embodiment, the antibody fragment is devoid of an Fc, which as shown in the Examples section attenuates (scFv) microglia cellular uptake of PFF (FIG. 11C) and oligomers (FIG. 11D) conjugated to Alexa fluor 488 (FIGS. 12C and 12D) in a dose dependent manner, whereas Fc containing antibodies do not (FIGS. 12E and 12F).

According to a specific embodiment, the antibody fragment is a single chain Fv (scFv).

According to a specific embodiment, the scFv comprises the amino acid sequence of the mature form of SEQ ID NO:42 or 44.

According to a specific embodiment, the scFv comprises the scFv amino acid sequence encoded by the plasmid of ATCC Deposit Designation PTA-125004.

According to a specific embodiment, an antibody or antigen-binding fragment thereof (e.g., an scFv) comprises six CDRs comprising the same amino acid sequences as the six CDRs encoded by the plasmid of ATCC Deposit Designation PTA-125004.

According to a specific embodiment, an antibody or antigen-binding fragment thereof (e.g., an scFv) comprises a VH comprising the same amino acid sequence as the VH encoded by the plasmid of ATCC Deposit Designation PTA-125004. According to a specific embodiment, an antibody or antigen-binding fragment thereof (e.g., an scFv) comprises a VL comprising the same amino acid sequence as the VL encoded by the plasmid of ATCC Deposit Designation PTA-125004. According to a specific embodiment, an antibody or antigen-binding fragment thereof (e.g., an scFv) comprises a VH comprising the same amino acid sequence as the VH encoded by the plasmid of ATCC Deposit Designation PTA-125004 and a VL comprising the same amino acid sequence as the VL encoded by the plasmid of ATCC Deposit Designation PTA-125004.

According to a specific embodiment, the antibody fragment is a Fab.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J. 73: 119-126 (1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., *Proc. Nat'l Acad. Sci. USA* 69:2659-62 (19720). Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, *Methods* 2: 97-105 (1991); Bird et al., *Science* 242:423-426 (1988); Pack et al., *Bio/Technology* 11:1271-77 (1993); and U.S. Pat. No. 4,946,778, each of which is hereby incorporated by reference in its entirety.

According to a specific embodiment, the antibody fragment is isolated from a library, e.g., a human library and hence no need for further humanization for therapeutic uses as further described herein below.

According to a specific embodiment, the antibody is a fully human antibody.

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature,* 321:522-525 (1986); Riechmann et al., *Nature,* 332:323-329 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (Jones et al., *Nature,* 321:522-525 (1986); Riechmann et al., *Nature* 332:323-327 (1988); Verhoeyen et al., *Science,* 239:1534-1536 (1988)), by substituting rodent CDRs or other CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.*, 227:381 (1991); and Marks et al., *J. Mol. Biol.*, 222:581 (1991); see also the Examples section). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)). Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to a specific embodiment, the antibody or an antigen-binding fragment thereof is an isolated antibody or antigen-binding fragment, i.e., not part of a library, or isolated from the physiological environment e.g., the human body.

An antibody or antigen-binding fragment according to some embodiments of the invention is produced by recombinant DNA technology.

Thus, according to an aspect of the invention there is also provided an isolated polynucleotide comprising a nucleic acid sequence encoding the antibodies or antigen-binding fragments thereof as described herein (e.g., PMS208).

According to a specific embodiment, the nucleic acid sequences encoding the CDRs are as set forth in SEQ ID NOs:7-12. Such CDRs can be cloned into suitable antibody or antigen-binding fragment configurations, while the encoded proteins (i.e., antibodies or antigen-binding fragments thereof) maintain their functions as described herein.

According to a specific embodiment, the nucleic acid sequences encoding the antibody or antigen-binding fragment thereof e.g., PMS208 (SEQ ID NOs:1-6) are as set forth in SEQ ID NOs:7-12.

According to a specific embodiment, the nucleic acid sequences encoding the CDRs encode CDRs with the same amino acid sequences as the CDRs encoded by the plasmid of ATCC Deposit Designation PTA-125004.

According to a specific embodiment, the nucleic acid sequences encoding the CDRs comprise the CDR-encoding nucleic acid sequences of the plasmid of ATCC Deposit Designation PTA-125004.

According to a specific embodiment, a nucleic acid sequence encoding a VH encodes a VH with the same amino acid sequence as the VH encoded by the plasmid of ATCC Deposit Designation PTA-125004. According to a specific embodiment, a nucleic acid sequence encoding a VL encodes a VL with the same amino acid sequence as the VL encoded by the plasmid of ATCC Deposit Designation PTA-125004. According to a specific embodiment, a nucleic acid sequence encoding a VH and a VL encodes a VH with the same amino acid sequence as the VH encoded by the plasmid of ATCC Deposit Designation PTA-125004 and a VL with the same amino acid sequence as the VL encoded by the plasmid of ATCC Deposit Designation PTA-125004.

According to a specific embodiment, a nucleic acid sequence encoding a VH comprises the VH-encoding nucleic acid sequence of the plasmid of ATCC Deposit Designation PTA-125004. According to a specific embodiment, a nucleic acid sequence encoding a VL comprises the VL-encoding nucleic acid sequence of the plasmid of ATCC Deposit Designation PTA-125004. According to a specific embodiment, a nucleic acid sequence encoding a VH and VL comprises the VH-encoding nucleic acid sequence of the plasmid of ATCC Deposit Designation PTA-125004 and the VL-encoding nucleic acid sequence of the plasmid of ATCC Deposit Designation PTA-125004.

According to a specific embodiment, a nucleic acid encoding an scFv comprises the scFv-encoding nucleic acid sequence of the plasmid of ATCC Deposit Designation PTA-125004.

Also provided is an expression vector, comprising the polynucleotide operably linked to a cis-acting regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator, and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion or presentation of antibody or antigen-binding fragment thereof from a host cell in which it is placed. Preferably the signal sequence for this purpose is a mammalian signal sequence. The signal sequence can be cleaved to form a mature protein.

In some aspects, a vector provided herein can contain a promoter (e.g., eukaryotic promoter), an enhancer, and/or a polyadenylation site.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

According to an aspect of the invention there is provided a method of producing an alpha-synuclein antibody or antigen-binding fragment thereof, the method comprising:

(a) culturing a host cell comprising a nucleic acid construct or a polynucleotide as described herein in a cell culture under conditions which allow expression of an alpha-synuclein antibody or antigen-binding fragment thereof, and (b) recovering the antibody or antigen-binding fragment thereof from said cell culture.

Also provided is an anti-alpha-synuclein antibody or antigen-binding fragment thereof obtainable by the method, optionally wherein the antibody or antigen-binding fragment thereof has biological activities of some embodiments described herein.

Also provided are cells which comprise the polynucleotides/expression vectors as described herein.

Suitable host cells for cloning or expression of antibody-encoding vectors include prokaryotic or eukaryotic cells described herein. For example, antibodies or antigen-binding fragments thereof may be produced in bacteria, in particular when glycosylation and Fc effector function are not needed. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody or antigen-binding fragment thereof may be isolated from the bacterial cell paste in a soluble fraction and can be further purified.

In addition to prokaryotes, eukaryotic microbes such as filamentous fungi or yeast are suitable cloning or expression hosts for antibody or antigen-binding fragment-encoding vectors, including fungi and yeast strains whose glycosylation pathways have been "humanized," resulting in the production of an antibody or antigen-binding fragment thereof with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody or antigen-binding fragment thereof are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies or antigen-binding fragments thereof in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0, and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

The antibody or antigen-binding fragment thereof (e.g., scFv) can be isolated from the host cell or conditioned medium using methods which are well known in the art.

In accordance with the methods and techniques described, the antibodies or antigen-binding fragments thereof (e.g., scFvs) described herein may be screened, selected or evaluated for their biological activity and optionally therapeutic potential in cell culture models and/or transgenic animal models for alpha-synuclein pathology.

According to a specific embodiment, the antibody or antigen-binding fragment thereof (e.g., scFv) is capable of inhibiting expression and secretion of pro-inflammatory cytokines from microglia cells incubated with PFF.

As used herein a "pro-inflammatory cytokine" refers to a type of signaling molecule (a cytokine) that is excreted from immune cells like helper T cells (Th) and macrophages, and certain other cell types that promote inflammation. They include interleukin-1 (IL-1), IL-5, IL-12, and IL-18, tumor necrosis factor (TNF), interferon gamma (IFN-gamma), and granulocyte-macrophage colony stimulating factor and play an important role in mediating the innate immune response. Inflammatory cytokines are predominately produced by and involved in the upregulation of inflammatory reactions. Dysregulation of pro-inflammatory and anti-inflammatory cytokines has also been linked to depression and other neurological diseases. A balance between proinflammatory and anti-inflammatory cytokines is necessary to maintain health.

Pro-inflammatory cytokines and neuroinflammation are important not only in inflammatory responses but also in neurogenesis and neuroprotection. Sustained stress and the subsequent release of pro-inflammatory cytokines lead to chronic neuroinflammation, which contributes to a variety of medical conditions including but not limited to schizophrenia, depression and other medical conditions that are described herein below (under "Neuroinflammation"). Hippocampal glucocorticoid receptors (GRs) and the associated hypothalamus-pituitary-adrenal (HPA) axis have close interactions with pro-inflammatory cytokines and neuroinflammation. Elevated pro-inflammatory cytokine levels and GR functional resistance create a vicious cycle. In brief, chronic neuroinflammation inhibits GR function, which in turn exacerbates pro-inflammatory cytokine activity and aggravates chronic neuroinflammation. On the other hand, neuroinflammation causes an imbalance between oxidative stress and the anti-oxidant system, which is also associated with a variety of medical conditions.

Alzheimer's disease (AD) is a progressive neurodegenerative disorder of the brain, which is characterized by the formation of extracellular amyloid plaques (or senile plaques) and intracellular neurofibrillary tangles. However, increasing evidences demonstrated that neuroinflammatory changes, including chronic microgliosis are key pathological components of AD. Microglia, the resident immune cells of the brain, constantly survey the microenvironment under physiological conditions. In AD, deposition of β-amyliod (Aβ) peptide initiates a spectrum of cerebral neuroinflammation mediated by activating microglia. Activated microglia may play a potentially detrimental role by eliciting the expression of pro-inflammatory cytokines such as interleukin (IL)-1β, IL-6, and tumor necrosis factor-α (TNF-α; TNFα) influencing the surrounding brain tissue. Emerging studies have demonstrated that up-regulation of pro-inflammatory cytokines play multiple roles in both neurodegeneration and neuroprotection.

The Examples section which follows describes an embodiment for analyzing the effect of an antibody or antigen-binding fragment thereof (e.g., scFv) on secretion of pro-inflammatory cytokines from microglia cells incubated with PFF, e.g., and Interferon-7 (IFNγ) or interleukin-5

(IL-5) responses are measured by colour enzyme-linked immunospot (ELISPOT) assay, enabling quantification of responsive T cells.

Briefly, pro-inflammatory cytokines can be measured in vitro (Example 7 and Example 10) at the RNA or protein level and optionally or alternatively evaluated functionally in vivo in a relevant animal model (see e.g., Example 9).

As used herein "inhibiting" refers to at least 10%, 20%, 30%, 40%, 50%, 60, 70%, 80%, 90% or complete inhibition in a biological function (e.g., in pro-inflammatory cytokines expression (e.g., mRNA) or secretion), as compared to a cell (e.g., microglia cell or a blood cell (e.g., PBMC)) untreated with the antibody or antigen-binding fragment thereof (e.g., scFv). Generally, analysis or protein expression can be done at the RNA or protein level. Examples include, but are not limited to, RT-PCR, chromatography, electrophoretic methods, and immunodetection assays such as ELISA, Western blot analysis, and immunohistochemistry.

According to a specific embodiment, inhibition of neuroinflammation is manifested by attenuating secretion of TNFα, IL6, IFN-gamma by microglia and PBMC and/or by reducing uptake of PFF to microglia and PBMC.

According to a specific embodiment, inhibition of neuroinflammation is manifested by tuning down the autoimmune response of T cells to oligomers/PFF as evidenced by IL-5 and IFNg by e.g., Elispot.

According to a specific embodiment, the antibody or antigen-binding fragment thereof (e.g., scFv) is capable of inhibiting uptake of PFF by macrophages or PBMC.

This can be analyzed as described in the Materials and Methods section of the Examples section which follows under "Uptake of alpha-synuclein fibrils and oligomers in cells" using FACS for detecting uptake indicated as relative geomean fluorescence intensity (gMFI).

According to a specific embodiment, the antibody or antigen-binding fragment thereof (e.g., scFv) is capable of inhibiting alpha-synuclein oligo/PFF-specific helper T cell activation by PFF. As shown in the Examples section which follows, IFNγ was used as a representative cytokine to detect CD4+T helper 1 (Th1) class II T cells, and IL-5 as a representative cytokine secreted by CD4+T helper 2 (Th2) class II T cells.

According to a specific embodiment the antibody or antigen-binding fragment thereof (e.g., scFv) is capable of inhibiting seeding and spreading of alpha-synuclein.

The aggregation of α-synuclein presumably starts with a conformational shift of the monomeric protein, followed by the step-wise formation of larger multimeric protein species comprising toxic soluble oligomers and preformed fibrils (PFF). These forms are potential drivers of seeding of (aggregated forms which are taken up by neuronal cells and catalyze the conversion of alpha-synuclein soluble protein molecules into their aggregated forms) and subsequent propagation culminating in widespread Lewy body pathology.

A seeding and spreading assay is described under the Materials and Methods section of the Examples section which follows under the header "Spreading and seeding determination of human PFF in vitro."

According to a specific embodiment, the antibody or antigen-binding fragment thereof (e.g., scFv) is capable of preventing aggregation of alpha-synuclein as determined by Thioflavin T (ThT).

The ability to prevent aggregation of monomeric protein or oligomers to high order aggregates (PFF) renders the antibody or antigen-binding fragment thereof (e.g., scFv) specifically applicable for both prevention and/or treatment at early and late stages of the disease (i.e., synucleinopathy) when different forms are evident.

According to a specific embodiment of the invention, the antibody or antigen-binding fragment thereof (e.g., scFv) is capable of ameliorating a motorical or physiological phenotype in a synucleinopathy mouse model. Relevant disease models include, but are not limited to, the mouse synuclein PFF induced Parkinson's disease, Adeno Associated Virus (AAV) transduced rats expressing human synuclein induced Parkinson's disease and Rotenone induced Parkinson's disease.

The clinical parameters include, but are not limited to, motoric functions: e.g., neuromuscular strength, forelimb asymmetry assessment, motor coordination and balance; behavioral functions e.g., exploratory behavior e.g., rearing; physiological parameters: e.g., body weight; and cognitive parameters: e.g., novel object recognition.

According to a specific embodiment, the antibody or antigen-binding fragment thereof (e.g., scFv) is conjugated to an agent selected from the group consisting of a therapeutic agent, a prodrug, a peptide, a protein, an enzyme, a virus, a lipid, a biological response modifier, a pharmaceutical agent, and PEG, e.g., by the covalent attachment of any type of molecule to the antibody or antigen-binding fragment thereof (e.g., scFv) such that covalent attachment does not prevent the antibody or antigen-binding fragment thereof (e.g., scFv) from specifically binding to its cognate epitope. For example, but not by way of limitation, antibodies and antigen-binding fragments thereof (e.g., scFv) can be modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids. Methods of conjugation are further described herein below.

The ability of the antibodies or antigen-binding fragments thereof (e.g., scFvs) of some embodiments of the invention to bind the pathological forms of the alpha-synuclein (i.e., oligomers and PFF) with higher affinity than to the monomeric form, renders it particularly useful for detection of these forms and diagnosis of synucleinopathies.

Thus, according to an aspect of the invention there is provided a method of detecting alpha-synuclein, the method comprising:

(a) contacting a biological sample with the antibody or antigen-binding fragment thereof (e.g., scFv) as described herein under conditions which allow formation of immunocomplexes; and (b) determining presence and/or level of said immunocomplexes.

For the purpose of detection of alpha-synuclein oligomers/PFF or diagnosis of synucleinopathies, the antibody or antigen-binding fragment thereof (e.g., scFv) can be bound to a detectable moiety or another antibody or antigen-binding fragment thereof or a secondary antibody or antigen-binding fragment thereof can be used dependent on the immunoassay that is being implemented e.g., ELISA, sandwich ELISA, immunohistochemistry e.g., on sections and more as the skilled artisan sees fit.

The term "detecting", as used herein, refers to the act of detecting, perceiving, uncovering, exposing, visualizing or identifying an aggregation state of alpha-synuclein. The precise method of detecting is dependent on the detectable moiety (also referred to herein as identifiable moiety) to which the antibody or antigen-binding fragment thereof (e.g., scFv) is attached.

The above-mentioned detection method can be harnessed to the diagnosis of synucleinopathies.

As used herein the term "diagnosing" refers to classifying a disease, determining a severity of a disease (grade or stage), monitoring progression, forecasting an outcome of the disease and/or prospects of recovery.

The subject may be a healthy subject (e.g., human) undergoing a routine well-being check up. Alternatively, the subject may be at risk of the disease. Alternatively, the method can be used to monitor treatment efficacy.

As mentioned, the method of the present invention is effected under conditions sufficient to form an immunocomplex (e.g. a complex between the antibodies or antigen-binding fragments (e.g., scFvs) of the present invention and the alpha-synuclein oligomers/PFF); such conditions (e.g., appropriate concentrations, buffers, temperatures, reaction times) as well as methods to optimize such conditions are known to those skilled in the art, and examples are disclosed herein.

Accordingly there is provided a method of diagnosing a synucleinopathic disease in a subject, comprising:

(a) assessing the level, localization, conformation or a combination thereof of alpha-synuclein in a subject to be diagnosed with the antibody or antigen-binding fragment thereof (e.g., scFv) as described herein, optionally attached to a detectable moiety;

(b) comparing the level, localization, conformation or combination thereof of alpha-synuclein in the subject to one or more reference standards derived from one or more control samples, wherein a difference or similarity between the level, localization, conformation or combination thereof of α-synuclein in the subject and the reference standard indicates whether the subject has a synucleinopathic disease.

The detection/diagnosis can be effected in-vitro on a biological sample.

Alternatively, detection/diagnosis can be effected in-vivo.

Examples of biological samples that can be used in accordance with the present teachings include, but are not limited to, blood, serum, plasma, CSF, brain tissue from biopsies/urine and sputum).

The selection of the detection method will much depend on the detectable moiety.

Thus, determining a presence or level of the immunocomplex of the present invention is dependent on the detectable moiety to which the antibody or antigen-binding fragment thereof (e.g., scFv) is attached.

Examples of detectable moieties that can be used in the present invention include but are not limited to radioactive isotopes, phosphorescent chemicals, chemiluminescent chemicals, fluorescent chemicals, enzymes, fluorescent polypeptides and epitope tags. The detectable moiety can be a member of a binding pair, which is identifiable via its interaction with an additional member of the binding pair, and a label which is directly visualized. In one example, the member of the binding pair is an antigen which is identified by a corresponding labeled antibody. In one example, the label is a fluorescent protein or an enzyme producing a colorimetric reaction.

Further examples of detectable moieties, include those detectable by Positron Emission Tomagraphy (PET) and Magnetic Resonance Imaging (MRI), all of which are well known to those of skill in the art.

When the detectable moiety is a polypeptide, the immunolabel (i.e. the antibody or antigen-binding fragment thereof (e.g., scFv) conjugated to the detectable moiety) can be produced by recombinant means or may be chemically synthesized by, for example, the stepwise addition of one or more amino acid residues in defined order using solid phase peptide synthetic techniques. Examples of polypeptide detectable moieties that can be linked to the antibodies of the present invention using recombinant DNA technology (in which the polynucleotide encoding the antibody is translationally fused to the detectable moiety) include fluorescent polypeptides, phosphorescent polypeptides, enzymes and epitope tags.

Alternatively, chemical attachment of a detectable moiety to the antibodies or antigen-binding fragments thereof (e.g., scFvs) provided herein can be effected using any suitable chemical linkage, direct or indirect, as via a peptide bond (when the detectable moiety is a polypeptide), or via covalent bonding to an intervening linker element, such as a linker peptide or other chemical moiety, such as an organic polymer. Such chimeric peptides can be linked via bonding at the carboxy (C) or amino (N) termini of the peptides, or via bonding to internal chemical groups such as straight, branched or cyclic side chains, internal carbon or nitrogen atoms, and the like. Such modified peptides can be easily identified and prepared by one of ordinary skill in the art, using well known methods of peptide synthesis and/or covalent linkage of peptides. Description of fluorescent labeling of antibodies is provided in details in U.S. Pat. Nos. 3,940,475, 4,289,747, and 4,376,110.

Thus, the conjugates described herein can be prepared by known methods of linking antibodies with lipids, carbohydrates, protein, toxins, drugs or other atoms and molecules. In some embodiments, the conjugate is formed by site-specific conjugation using a suitable linkage or bond. Site-specific conjugation is more likely to preserve the binding activity of the antibody or antigen-binding fragment thereof (e.g., scFv). The substance can be conjugate or attached at the hinge region of a reduced antigen binding construct via thioether bond formation. In some embodiments, tyrosine conjugation can be employed. Other linkages or bonds used to form the conjugate can include, but are not limited to, a covalent bond, a non-covalent bond, a disulfide linkage, a hydrazone linkage, an ester linkage, an amido linkage, and amino linkage, an imino linkage, a thiosemicarbazone linkage, a semicarbazone linkage, an oxime linkage and a carbon-carbon linkage. In some embodiments, no cysteine or other linking aspect, need be included in antibody (Bioconjugate Techniques (Third Edition) Author(s): Greg T. Hermanson ISBN: 978-0-12-382239-0).

Exemplary methods for conjugating moieties are described in WO2017/027325 and U.S. Pat. No. 9,078,931, each of which is hereby incorporated by reference in its entirety.

The level, localization, and/or conformation of alpha-synuclein can be assessed by any suitable method known in the art comprising, e.g., analyzing alpha-synuclein by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/

MS), and laser densitometry. In vivo imaging of alpha-synuclein can comprise positron emission tomography (PET), single photon emission tomography (SPECT), near infrared (NIR) optical imaging, or magnetic resonance imaging (MRI).

Also provided is a composition comprising a biological sample of a subject diagnosed with a synucleinopathy (or being suspected as having the disease) and the antibody or antigen-binding fragment thereof (e.g., scFv) as described herein.

The present methods can be used to classify the disease determining responsiveness to treatment, selecting treatment and determining disease outcome.

According to some embodiments of the invention, the method further comprises informing the subject of the predicted diagnosis, treatment and/or the predicted prognosis of the subject.

As mentioned the antibodies or antigen-binding fragments thereof (e.g., scFv) provided herein can also be used in therapeutics. One or more polynucleotides encoding the antibodies or antigen-binding fragments thereof can also be used in therapeutics.

Thus, according to an aspect of the invention there is provided a method of treating or preventing a synucleinopathic disease in a subject, the method comprising administering to the subject a therapeutically effective amount of the antibody or antigen-binding fragment thereof (e.g., scFv), the composition, the polynucleotide, the vector or the cell comprising the antibody or antigen-binding fragment thereof (e.g., scFv) (optionally devoid of an Fc), thereby treating or preventing the synucleinopathic disease.

According to an aspect there is provided a method of treating or preventing neuroinflammation in a subject, the method comprising administering to the subject a therapeutically effective amount of the antibody or antigen-binding fragment thereof (e.g., scFv), the composition, the polynucleotide, the vector or the cell comprising the antibody or antigen-binding fragment thereof (e.g., scFv) (not necessarily devoid of an Fc), thereby treating or preventing the neuroinflammation.

According to a specific embodiment the antibody or antigen-binding fragment thereof (e.g., scFv) is administered to the subject. According to a specific embodiment one or more polynucleotides encoding the antibody or antigen-binding fragment thereof (e.g., scFv) are administered to the subject. The one or more polynucleotides can be contained in one or more vectors. The vectors can be, for example, viral vectors such as adenoviral vectors or lentiviral vectors.

Synucleinopathic diseases or synucleinopathies are a diverse group of neurodegenerative disorders that share a common pathologic lesion composed of aggregates of insoluble alpha-synuclein protein in selectively vulnerable populations of neurons and glia. Thus, the hallmark is accumulation and/or deposition of alpha-synuclein in the brain and the central nervous system. These disorders include, but are not limited to, Parkinson's disease (PD), Parkinson's Disease Dementia (PDD), dementia with Lewy bodies (DLB), juvenile-onset generalized neuroaxonal dystrophy (Hallervorden-Spatz disease), pure autonomic failure (PAF), multiple system atrophy (MSA) and neurodegeneration with brain iron accumulation type-1 (NBIA-I).

They are characterized by a chronic and progressive decline in motor, cognitive, behavioral, and autonomic functions, depending on the distribution of the lesions.

Parkinson's disease is an age-dependent neurodegenerative disease with unknown etiology. It is believed that sporadic Parkinson's disease results from a combination of genetic vulnerability and environmental insults. It is further believed that Parkinson's disease (PD), while triggered by disparate mechanisms follows a shared pathophysiologic pathway. One shared node is the involvement of alpha-synuclein. Linkage of this protein with Parkinson's disease pathogenesis has been established by the identification of both point mutations and triplication of the gene in familial cases, the localization of alpha-synuclein to Lewy bodies, one of the hallmark pathological features of Parkinson's disease, and the correlation of alpha-synuclein expression and disease pathology in neurotoxic models of Parkinson's disease. Further evidence indicates that particular forms of alpha-synuclein (e.g., misfolded and alpha-synuclein bonded dopamine) are involved in sporadic disease.

As used herein, the term "neuroinflammatory disease or disorder" refers to a medical condition that is manifested by inflammation of the nervous tissue. It may be initiated in response to a variety of cues, including infection, traumatic brain injury, toxic metabolites, or autoimmunity. Examples of neuroinflammatory diseases or disorders include, but not limited to, Parkinson's Disease, Amyotrophic Lateral Sclerosis (ALS), Multiple Sclerosis (MS), Alzheimer's Disease (AD), Traumatic Brain Injury (TBI), irritable bowel syndrome, schizophrenia, bipolar disorder, depression, anxiety (generalized anxiety disorder, obsessive-compulsive disorder and post-traumatic stress disorder, dementia, autism spectrum disorder (autism, asperger's disorder, pervasive developmental disorder, childhood disintegrative disorder), ataxia telangiectasia, Coackayne syndrome, corticobasal degeneration, Creutzfeldt-Jakob disease, spinocerebellare ataxia type 3, neuroborreliosis, primary lateral sclerosis, progressive supranuclear palsy, Schilder's disease, subacute combined degeneration of spinal cord secondary to pernicious anemia, drug-induced demyelination, radiation induced demyelination, spinal muscular atrophy, tabes dorsales, spinal cord injury, chronic inflammatory demyelinating neuropathy, a congenital metabolic disorder, polymyositis, temporal arteritis, vasculitis, autism, and interstitial cystitis, Hurler's Syndrome, Scheie's Syndrome, Hunter's Syndrome, San Fillipo's Syndrome, Maroteaux-Lany Syndrome, Sly Syndrome, Fucosidosis, Alpha-mannosidosis, Beta-mannosidosis, Schindler's Disease, Pompeii's Disease, Woman's Disease, and Infantile Neuronal Ceroid Lipofuscinosis.

As used herein "subject in need thereof" includes mammals, preferably human beings at any age which suffer from the pathology, i.e., synucleinopathy or neuroinflammation. According to a specific embodiment, this term encompasses individuals who are at risk to develop the pathology.

As mentioned, it may be desirable to use the non-Fc containing fragment and smallest (with lowest molecular weight) as possible antibody fragments for therapeutic purposes.

The antibody or antigen-binding fragment thereof (e.g., scFv), the composition, the polynucleotide, the vector, or the cell comprising the antibody or antigen-binding fragment thereof (e.g., scFv) of some aspects provided herein can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody or antigen-binding fragment thereof (e.g., scFv), the composition, the polynucleotide, the vector, or the cell comprising the antibody or antigen-binding fragment thereof (e.g., scFv) of some aspects provided herein accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to some embodiments of the invention, the administration route is intranasal.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions suitable for use in context of some embodiments of the invention include compositions wherein the active ingredients are contained in an amount effective to achieve the intended purpose. More specifically, a therapeutically effective amount means an amount of active ingredients (antibody or antigen-binding fragment thereof (e.g., scFv), the composition, the polynucleotide, the vector, or the cell comprising the antibody or antigen-binding fragment thereof (e.g., scFv) of some aspects provided herein) effective to prevent, alleviate or ameliorate symptoms of a disorder (e.g., synucleinopathy) or prolong the survival of the subject being treated.

Furthermore, a pharmaceutical composition can be formulated as a vaccine, for example, if the pharmaceutical composition of the invention comprises an anti-alpha-synuclein antibody or antigen-binding fragment thereof (e.g., scFv), as described herein, for passive immunization. As mentioned in the background section, oligomeric species of alpha-synuclein have been reported extracellularly in plasma and CSF (El-Agnaf et al., FASEB J. 20 (2006), 419-425) and passive immunization studies in mouse models of Parkinson's disease show that extracellular mouse monoclonal antibodies against alpha-synuclein can reduce accumulation of intracellular alpha-synuclein aggregates (Masliah et al., Neuron, 46 (2005), 857-868). Accordingly it is prudent to expect that the human anti-alpha-synuclein antibodies or antigen-binding fragment thereof (e.g., scFv) provided herein are particularly useful as a vaccine for the prevention or amelioration of the medical conditions described herein e.g., synucleinopathic diseases such as PD, DLB and MSA.

Compositions of some aspects provided herein may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition.

Hence, certain aspects provided herein relate to the use of the alpha-synuclein antibody or antigen-binding fragment thereof, the polynucleotide, the vector, or the cell provided herein for the preparation of a pharmaceutical or diagnostic composition for prophylactic and therapeutic treatment of a synucleinopathic disease or neuroinflammation, monitoring the progression of a synucleinopathic disease or neuroinflammation or a response to a synucleinopathic disease treatment or neuroinflammation treatment in a subject or for determining a subject's risk for developing a synucleinopathic disease or neuroinflammation.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various aspects of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Preparation of Alpha-Synuclein PFFs

Purified α-syn monomer (1 mg Alexotech, Sweden) was thawed in a 1.5-ml microcentrifuge tube in a 37° C. water bath until complete thawing. The tube was centrifuged at 100,000×g at 4° C. for 60 min to pellet any aggregated material. Supernatant was removed and diluted with PBS in a new, low binding sterile 1.5-ml micro centrifuge tube (Protein LoBind Tube 1.5, Eppendorf tubes, Cat no.: 022431081) for the use of generating PFFs in to a final volume of 200 µl and a final concentration of 5 mg/ml. Tube was placed in a closed thermomixer (QSR technologies, U.S.A) at 37° C. incubation for 7d at 1000 rpm (solution should appear turbid). The solution was divided into aliquots (10-20 µl) into sterile microcentrifuge tubes and stored at −80° C. Before use, PFF was centrifuged at 100,000×g, 4° C. for 60 min. The supernatant was removed and PFF was sonicated in new sterile PBS (20% power 1 sec on 1 sec off in 60 sec total on (30 sec net on time)).

Preparation of Aldehyde Induced Alpha-Synuclein Oligomers

Purified α-syn monomer (2 mg/ml Alexotech, Sweden) (in PBS, pH 7.4) was mixed together with HNE (4-Hydroxynonenal) 20 mg/ml (in DMSO) in a low binding tube (Protein LoBind Tube 1.5, Eppendorf tubes, Cat no.: 022431081) for a final concentration of 140 μM α-syn and 4200 μM HNE, respectively. Samples were incubated at 37° C. for 18 h and analyzed in SDS-PAGE, silver stain (manufacture protocol). A 14 KDa form is the oligomer (aSyn adopts extended conformation oligomeric form (spherical—monomers to hexamers), with dimers being the major species (SDS resistant) and PFF Fibril forms (dimers and above). Of note, there can be an overlap in the size but not in the structure (fibril vs. round oligomers).

Cell Viability Assays

The toxicity of a-syn fibrils was assessed by the MTT cell viability assay on differentiated human neuroblastoma SH-SY5Y cells. For the MTT assay, cells were plated at a density of 10,000 cells per well on 96-well plates in 100 of culture medium per well. Following 24 h, the medium was exchanged with 100 of fresh medium containing 10 μM of retinoic acid (RA) for neuronal differentiation. After 96 additional hours, 0.0625 M of alpha-syn fibrils, 0.0156 μM a-syn oligomers or human PD brain extracts (1:1000 in PBS) were incubated with PMS208 or sham scFv (80R a proprietary unspecific protein engineered clone) for additional 4 h at room temperature and added to the differentiated neuronal cells for 24 h at 37° C. Control samples were prepared with the addition of identical volumes of buffer. After 24 h of incubation, the cells were incubated for another 4 h with 100 of serum-free Dulbecco's modified Eagle's medium without phenol red, containing 0.5 mg/ml MTT. Then, 100 of cell lysis solution (20% SDS, 50% N,N-dimethylformamide) were added to each well, and the samples were incubated over night at 37° C. to allow complete lysis. The absorbance of the formazan was measured at 570 nm in a Tecan infinite 200 pro microplate reader (Tecan, Mannedorf, Switzerland).

Uptake of Alpha-Synuclein Fibrils and Oligomers in Cells

Human PBMC's, BV-2 (mouse microglia, ICLC ATL03001) and peritoneal mouse macrophages were split into 12 well culture plates (Greiner CELLSTAR multiwell culture plates) on the day before the experiment. 0.3 M synuclein fibrils or oligomers conjugated with Alexa 488, pre-incubated with either 0.1, 0.5, 1.5, 3, 4 and 5 g/ml PMS208 or PMS208-Fc for 30 min at room temperature, were added to cells with culture media (RPMI 1640, 10% FBS, 2 mM L-Glutamine, 1% Pen/Strep). The conditioned medium was also pre-incubated with PMS208 (without pff/oligomers) for 30 min as control. Cells were then incubated at 37° C. for 24 h and harvested. Flow cytometry (FL1—blue laser (488 nm) was used to measure fibrils/oligomers (conjugated to ALEXA fluor 488) uptake indicated as relative geomean fluorescence intensity (gMFI). Cytochalasin D (Cyto D) is an antibiotic which is used to inhibit cellular uptake (control).

Aggregation Studies of α-Syn Proteins Using Thioflavin T (ThT) Fluorescence

α-Syn in 10 mM phosphate buffer, pH 7.4, was filtered to ensure removal of preformed aggregates and then incubated at 37° C. with shaking at 1000 rpm (Thermomixer, QSR technologies, U.S.A) for 6 days in the presence of 2 different PMS208 concentrations. Aliquots of the reactions were removed at each time point and added to a 10 M Thioflavin T (ThT) (Sigma, T3516) solution (prepared from a stock dissolved in 10 mM phosphate buffer, pH 7.4) in a low-binding black 96-well plate (Corning). Fluorescent measurements were performed using a Tecan infinite 200 pro microplate fluorescent reader (Tecan, Mannedorf, Switzerland) recording fluorescence measurements from 440 to 485 nm. All measurements were performed in triplicate.

Spreading and Seeding Determination of Human PFF In Vitro

Aliquot of 5 mg/ml PFF were thawed at room temperature immediately before use. PFFs were added to sterile PBS to a final concentration of 0.1 mg/ml (minimal volume for use is 200 ul) and then sonicated with 60 pulses at 10% power (total of 30s, 0.5 sec on, 0.5 sec off). Sonicated PFFs or equivalent volume of PBS as a control were diluted with prewarmed neuronal medium in a 1:20 dilution (with and without PMS208 treatment (15 ug/ml)) and added to neurons (primary neurons derived from wild-type, nontransgenic p0 mouse pups, (M J Beaudoin et al; Nature protocols)) 7 days after plating for additional 7-10 days. About 50% of the medium was changed once a week (the fresh medium does not need to contain more fibrils as the seeding takes place only once at the beginning of the experiment). Next, primary neuron culture cells were rinsed twice with PBS and each well was completely aspirated before adding ice cold RIPA lysis buffer with protease and phosphotase inhibitors. Neuronal cells were taken out from wells using a cell scraper and placed in a low binding 1.5 ml tubes on ice. Next, cells were sonicated (1 sec on, 1 sec off, time 5 sec—20%) and incubated on ice for 30 minutes. Samples were centrifuged at 17,000×g at 4° C. for 60 min, and supernatants were removed to a new low-binding 1.5 ml tubes, retained on ice or in a–20° C. freezer while additional (same volume) ice-cold RIPA lysis buffer with protease and phosphatase inhibitors was added to the pellet. The pellet tube was sonicated (1 sec on, 1 sec off, time 5 sec-20%) and centrifuged at 17,000×g at room temperature for additional 80 minutes, supernatant was discarded, and 2% (wt/vol) of SDS/RIPA added to the pellet with protease and phosphatase inhibitors. Cells were sonicated (1 sec on, 1 sec off, time 16 sec-20%), and a BCA/protein assay was performed on TX-100 supernatant and SDS extract. Samples were diluted with 2% (wt/vol) SDS extract into Laemmli buffer 2×+beta mercaptoethanol and heated at 95° C. for 5 minutes before loading on a 10% (wt/vol) gel. Proteins were transferred from a gel to a nitrocellulose membrane according to the manufacturer's instructions at 100 V for 75 minutes or overnight at 40 V. Membrane was blocked for 1 hour with TBST/5% (wt/vol) milk, stained with diluted primary antibodies (mouse anti-human aSyn (clone Syn204, BioLegend) 1:1000, rabbit anti-rodent synuclein (D37A6, CellSignal) 1:1000, anti-GAPDH (clone 6C5, Millipore) 1:2000 followed by secondary antibodies peroxidase-AffiniPure goat anti-mouse IgG (Jackson) 1:10000, mouse anti-rabbit IgG (Jackson)) 1:10000 TBS/1% (wt/vol) BSA, incubated for additional 1 hour (both primary and secondary separately) while shaking and rinsed×3 times (5 minutes each rinse) before enhanced chemiluminescence development.

Pull-Down Assay (Immunoprecipitation) of Serum Derived Alpha-Synuclein by PMS208

Human sera and human CSF obtained from PD patients were immunoprecipitated with different amounts of PMS208-Fc (5, 10 and 50 μg) bound to Dynabeads protein A (Dynabeads® Protein A for IP 1 ml, Life technologies, Grand Island, N.Y., USA) following manufacturer's instructions, then separated by SDS-PAGE (Bis-Tris 4-12% acrylamide) and transferred to protran nitrocellulose membranes. Membranes were analyzed by immunoblot for alpha-synuclein using mouse anti-human aSyn (clone Syn204, BioLegend-BLG838201; 1:1000) and mouse anti-aSyn phospho (Ser129) (clone P-syn/81A, BioLegend-BLG825701; 1:500) following peroxidase-AffiniPure goat anti-mouse IgG (Jackson; 1:10,000) before enhanced chemiluminescence development. 100 ng of recombinant human aSyn PFF and PBS were immunoprecipitated with 50 µg of PMS208-Fc bound to Dynabeads as positive and negative control respectively.

Animals

WT mice (C57BL/6JRccHsd background) and Rats (Sprague-Dawley) were purchased from Envigo RMS (Israel), Ltd. All housing, breeding, and procedures were performed according to the National Institute of Health (NIH) Guide for the Care and Use of Experimental Animals and approved by the Kaplan Medical Center Institutional Animal Care and Use Committee.

Subjects and Tissue Sampling

This study was performed at Kaplan Medical Centre in Rehovot, Israel under appropriate Institutional Review Board approval. Blood samples were obtained from the Israel National Blood Services (MDA) except for CSF and brain specimens included in the study which were collected at the Cambridge Brain Bank supported by the NIHR Cambridge Biomedical Research Centre.

Evaluation of the Effect of PMS208, Compared with PBS as Controls, on Mouse Alpha-Synuclein PFF Induced Parkinson's Disease (Stereotaxic Injections):

50 Male (5 groups of n=10) C57BL/6JRccHsd mice (2-4 months of age) were anesthetized by Isoflurane, and stereotaxically injected with recombinant aSyn fibrils (7 g of PFF per brain) in PBS. Control C57BL/6JRccHsd animals received sterile PBS. A single needle insertion (coordinates: +0.2 mm relative to bregma, 2.0 mm from midline) into the right forebrain was used to target the inoculum to the dorsal neostriatum located at a depth of 2.6 mm below the dura. Material was injected via a 10 µl Hamilton syringe at a rate of 0.5 µl per min (3.5 µl total volume) with the needle in place (33G) for >10 min at each target. Animals were inoculated at the right hemisphere unless otherwise indicated. After recovery from surgery, animals were treated by intranasal (IN) administration with 3 concentrations of PMS208 (16 ug/kg, 80 ug/kg and 320 ug/kg) twice a week, behavior tests (Grip test, Rota rod, Cylinder and NOR) were conducted at various predetermined time points before they were sacrificed at 9 weeks post injections by overdose with ketamine/xylazine and then transcardial perfusion with PBS (and additional perfusion with 4% formalin for histological studies). For histological studies the brain was removed and underwent overnight postfixation with neutral buffered formalin (Thermo Fisher Scientific), before being processed and embedded in O. C. T compound (Ref 4583, Tissue-Tek)—used for binding tissue to the specimen block and to surround and cover the tissue specimen. For biochemical studies, tissues were immediately frozen after removal and stored at −80° C. until used.

Evaluation of the Effect of PMS208, Compared to PBS as a Control, on Adeno Associated Virus (AAV) Transduce Rats Expressing Human Synuclein Induced Parkinson's Disease (Stereotaxic Injections of AAV):

38 female (5 groups) Sprague-Dawley rats (225-250 g) were anesthetized with an intraperitoneal injection of ketamine hydrochloride (100 mg/kg) and xylazine (10 mg/kg), and stereotaxically injected with AAV-aSyn into the right hemisphere. Injections were made into the SN at the following coordinates: anteroposterior (AP), −5.3; mediolateral (ML), +1.7; dorsoventral (DV), −7.2. Control animals received sterile PBS. Material was injected via a 10 µl Hamilton syringe at a rate of 0.3 µl per min with the needle in place (33G) for >10 min at each target. Animals were inoculated at the right hemisphere unless otherwise indicated. After recovery from surgery, animals were treated by intranasal (i.n.) administration with 3 concentrations of PMS208 (5 ug/kg, 50 ug/kg, and 250 ug/kg) 2 times/week, behavior tests (Two limb wire hang, Cylinder and Open Field) were conducted at various predetermined time points before they were sacrificed at 7 weeks post injections by overdose with ketamine/xylazine and then transcardial perfusion with PBS (and additional perfusion with 4% formalin for histological studies). For histological studies the brain was removed and underwent overnight postfixation with neutral buffered formalin (Thermo Fisher Scientific), before being processed and embedded in O.CT. For biochemical studies, tissues were immediately frozen after removal and stored at −80° C. until used. CSF and blood serum was collected from all animals. The AAV2 vector was used to overexpress human wild-type α-syn, in which the expression of the transgene is driven by the human CMV promoter. A total of $8 \times 10^8$ IFU were injected per animal (6 µL per animal).

Evaluation of the Effect of PMS208, Compared with PBS as Controls, on Rotenone Induced Parkinson's Disease Model:

24 adult male (3 groups) Sprague-Dawley rats (175-200 g) were anesthetized with an intraperitoneal (i.p.) injection of ketamine hydrochloride (100 mg/kg) and xylazine (10 mg/kg), and injected daily i.p. for 12 days with 1.5 mg/kg/d Rotenone (dissolved in DMSO/Olive oil), 2 mg/kg/d from day 5 and 2.5 mg/kg/d from day 9 prepared fresh twice a week. Animals were treated by intranasal (i.n.) administration with 10 µg (~40 g/kg) of PMS208 (5 µg in each nozzle) and PBS as sham at the first and every 3 days after (4 total). Behavior tests (Cylinder and Postural instability) were conducted at various predetermined time points before they were sacrificed at day 12. Transcardial perfusion with PBS and 4% formalin was done in all animals. For histological studies the brain was removed and underwent overnight postfixation with neutral buffered formalin (Thermo Fisher Scientific), before being processed and embedded in O. C. T. For biochemical studies, tissues were immediately frozen after removal and stored at −80° C. until used. CSF was collected from all animals.

Rotenone Treatment

The rotenone solution was first prepared as a 50× stock in 100% dimethylsulfoxide (DMSO) and diluted in olive oil, to obtain a final concentration of 1.5, 2, or 2.5 mg/mL rotenone in olive oil, 2% DMSO. Vortexing the solution creates a stable emulsion of the DMSO containing rotenone and olive oil. The solution was made fresh 2-3 times/week and stored in an amber septa vial protected from light and inverted several times before each injection to eliminate the possibility of settling. The solution was administered at 1 mL/kg, and control animals received the vehicle only. Experimental groups were comprised of at least 4-10 animals. Rotenone was administered by increased doses (day 0, day 2, and day 6) once a day for 12 consecutive days.

Immunohistochemistry

Brains were extracted and post-fixed in 4% PFA for 24 h and sunk in 30% sucrose. Brains were frozen on a microtome platform and cut to generate 16 and 40 m thick sections. A series of free-floating coronal sections was stained for either tyrosine hydroxylase (TH) or phosphorylated α-syn (pSyn). Tissue was incubated in 0.3% $H_2O_2$ for 45 min, rinsed, and blocked in 10% normal goat serum (1 h) and then incubated in primary mouse anti-pSyn (Ser129) (1:500, biolegend), mouse-anti-TH (1:200) antibodies overnight at 4° C. Then, sections were incubated in biotinylated secondary antisera against either mouse (1:400, Millipore, Temecula, Calif.) or rabbit IgG (1:400, Millipore, Temecula, Calif.) followed by the Vector ABC detection kit (Vector Labs, Burlingame, Calif.). Antibody labeling was visualized by exposure to 0.5 mg/ml 3,3' diaminobenzidine (DAB), 2.5 mg/ml nickel ammonium sulfate and 0.03% $H_2O_2$ in Tris buffer followed by incubation with the NovaRed kit (Vector Labs, Burlingame, Calif.). Sections were mounted on subbed slides, dehydrated to xylene, and coverslipped with xylene base mounting buffer.

Isolation and Culture of Human Peripheral Blood Mononuclear Cells (PBMC's):

Whole blood was diluted 1:1 ratio with PBS (Ca/Mg free), gently laid in ficoll (ratio 1:2), and centrifuged for 30 min, 1500 rpm (with slow acceleration and de-acceleration (0)). Buffy coat was collected into a new tube, washed with PBS, and centrifuged for 15 min in 1200 rpm. Additional wash with PBS was supplemented, and blood was centrifuged for 15 min in 1200 rpm before cells were resuspended in 10 ml PBS for counting.

ELISA Assay for Neuroinflammation

IL-6 and TNF-alpha (TNFα) protein levels in cells were detected using DuoSet Elisa assay (R&D System) following manufacturer protocol.

ELISPOT Assays

The assay is done by culturing PBMCs for 14 days (dilution of 1:1 with medium supplemented with IL-2 each couple of days) with PFF/oligomers in order to stimulate helper and cytotoxic T cells and then to test whether a-Syn pff/oligomers were recognized by those cells.

Specifically, culturing of PBMCs for in vitro expansion was performed by incubating in RPMI (Biological Industries, Israel) supplemented with 5% human AB serum (Biological Industries, Israel), GlutaMAX (Gibco), and penicillin and streptomycin (Biological Industries, Israel) at $2\times10^6$ per ml in the presence of alpha-synuclein PFF/oligomers at 10 g/ml. Every three days, 10 U/mlIL-2 in medium was added to the cultures. After 14 days, cultures were stimulated with 25 µg/ml fibrilized α-syn or 25 g/ml oligomerized α-syn and the response was measured by IFNγ and IL-5 ELISPOT. ELISPOT antibodies, mouse anti-human IFNγ (clone 1-D1K), mouse anti-human IL-5 (clone TRFK5), mouse anti-human IFNγ-HRP (clone 7-B6-1), and mouse anti-human IL-5 biotinylated (clone 5A10) were all from Mabtech.

Real Time PCR for Cell Activation 10-week old mice were injected with human α-syn PFF or oligomers into the striatum (with and without PMS208 treatment) to examine in vivo neuroinflammation. 72 hours post-intrastriatal injections, animals were sacrificed, and brains were dissected and homogenized. RNA from whole brain and suspension cells was isolated using SV total RNA isolation system kit (Promega) or EZ-RNA Total RNA Isolation Kit (Biological Industries, Israel) respectively following the manufacturer's protocol. Complementary DNA (cDNA) synthesis was carried out with qScript cDNA Synthesis Kit (Quanta bio) using 2 µg of total RNA as template. In order to examine neuroinflammation relative quantitation of gene expression was conducted by real time PCR carried out using TaqMan® Gene Expression Assay (Applied Biosystems). Fluorescent (FAM)-labeled IL-6, TNFα, INFγ, IL-12, Caspase 3, Arg1, Chi313, and Mrcl were normalized to a internal control, GAPDH. All comparisons refer to sham. Analysis was done using the Comparative Ct Method (ΔΔCT).

Behavioral Assessment

Cylinder Test

Cylinder test is a motor assessment of forelimb asymmetry. Rats were individually put into a glass cylinder (20 cm diameter, 34 cm height) and were video recorded for 5 minutes and until they touched the cylinder wall with their forelimbs 20 times. The recordings were analyzed by an investigator who was not aware of the identity of the rats. The data are presented as the following formula: (Left touch)/(Right touch+Left touch+Both touch).

Wire Hang Test

Neuromuscular strength was tested with a wire hang test. The mouse was placed on a wire mesh, waved gently so that the mouse gripped the wire, and then inverted. Latency to fall was recorded with a 15 minutes cut-off time.

Two Limb Wire Hang Test

Neuromuscular strength was tested with a two limb wire hang test. The rat was placed on a wire string, waved gently so that the rat gripped the wire. Latency to fall was recorded with a 10 minutes cut-off time.

Rotarod Behavioral Analysis

The Ugo Basile 47650—Mouse NG rotarod treadmill (Ugo Basile) was used to assess fine motor coordination and balance. Rotarod performance is measured on a rotating rod as the mice must walk forward to avoid falling off a continuously rotating cylinder (Carter et al. 1999; Jones and Roberts 1968). Pre-training consisted of 4 consecutive trials at low rotational speed of 20 rpm. Two trials were measured on a rod that accelerates from 0-50 rpm, and the average time on the rod for each mouse was used for data analysis. Time on the rod was used to assess fine motor coordination and balance.

Rearing Behavior

When placed in a clear cylinder, rats will engage in exploratory behavior, including rearing. During rearing behavior, the forelimbs will contact the wall of the cylinder. For this test, the rat was placed in a clear plexiglass cylinder (height=30 cm, diameter=20 cm) for 3 minutes. The test was conducted under low red-light conditions and video-recorded, and during video playback, the number of rears was quantified. To be classified as a rear, the animal had to raise forelimbs above shoulder level and make contact with the cylinder wall with either one or both forelimbs. Removal of both forelimbs from the cylinder wall and contact with the table surface was required before another rear was scored. This test has been successfully used previously to assess behavioral deficits in the rats receiving subcutaneous or intravenous rotenone.

Novel Object Recognition (NOR)

24 hours before testing, all animals were habituated to the testing apparatus for 10 minutes (50 cm box, 40 cm high). The day after, animals were introduced to the objects: first, two identical objects were placed in the box, and mice were allowed to explore objects for 5 minutes. The same procedure continued until 5 mice were done. The entire phase for 5 mice lasted 30 minutes. Immediately after, these 5 mice were tested in the same order as before. Animals were introduced to two different objects, one familiar object and one novel object that the mice never encountered. Mice were allowed to explore objects for 5 minutes and then removed from the box. At all phases, after each mouse was removed from the box, the box was sterilized with alcohol. Sample and novel objects and their locations were counterbalanced across animals. Each trial was videotaped, and time and frequency spent with each object was measured using Noldus EthoVision XT 11.5 (Noldus information Technology, The Netherlands).

Statistical Analysis

Values shown in the Figures are presented as mean+/−SEM. P values for determination of the statistical significance of differences were calculated by means of paired, two-tailed Student's t test, two-tailed Mann-Whitney U or Wilcoxon's rank-sum tests, one-way ANOVA with a post hoc Dunnet's or one-way ANOVA with Tukey's post test.

Example 1

Generation of scFv and scFv-Fc from Fab Libraries of Healthy Volunteers

A human Fab/scFv library with a repertoire from over 110 individuals and diversity of $1\times10^{11}$ was screened against recombinant modified human alpha-synuclein (PFF and oligomers). Use of this library allows for the identification of combinations of variable heavy and variable light chains that are not found together in any of the 110 individuals. High-affinity binders were selected by 3 rounds of biopanning in which 42 positive clones were identified (FIG. 1) and sequenced. From sequencing data, 6 clones were identified with unique variable regions. These 6 clones, named Fab 1 to Fab 6, were subsequently expressed in *E. coli* in large scale as a Fab antibody format (50 KDa). Following Nickel column purification, the Fabs were analyzed by SDS-gel, and their protein concentrations were determined.

Figure 2:
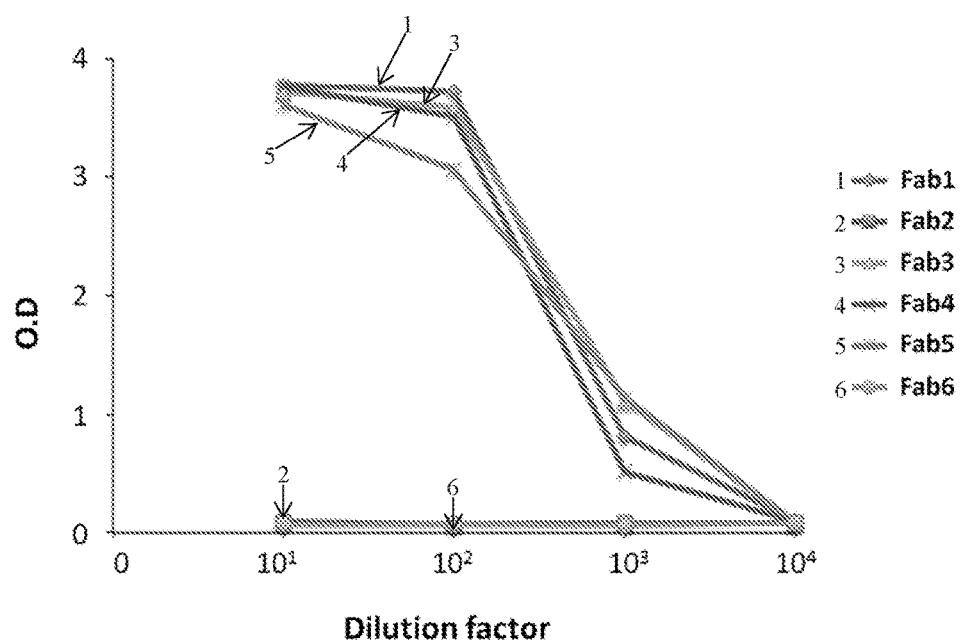
FIG. 2 is a graph showing alpha-synuclein binding analysis by ELISA assay for 6 unique clones (Fab forms).

A standard ELISA assay was performed using alpha-synuclein PFFs as the coating protein. As shown in FIG. 2, Fabs 1 (PMS208), 3 (PMS210), 4 (PMS211), and 5 (PMS212) bound to the coating protein in a concentration dependent manner. However, Fabs 2 (PMS209) and 6 (PMS213) did not show binding under these assay conditions.

Example 2

Generation of scFv-Fc from 3 Unique Clones

Three selected unique clones (PMS208, PMS210 and PMS212) were cloned to a mammalian expression vector as a scFv conjugated to human IgG1 Fc format (scFv-Fc). GGGGSx3(SEQ ID NO:47) linker was used to link between the variable regions from heavy (VH) and light (VL) chains (FIG. 4).

Example 3

Generation of scFv from Clone PMS208

PMS208 showed high affinity binding to alpha-synuclein PFF's and oligomers seen in surface Plasmon resonance (Biacore SPR system, GE Healthcare Life Sciences) and ELISA assays in scFv-Fc format (FIGS. 6 and 7), to both human and mouse alpha-synuclein PFF/oligomers. For human aSyn, see materials and methods (Preparation of alpha-synuclein PFFs). For mouse monomers, mouse alpha-synuclein gene was cloned into a mammalian expression vector with his-tag, and HEK293T cells were transfected with the vector to express mouse synuclein his-tag protein and then purified in His-trap column (FPLC).

PMS208 was cloned and expressed as single chain variable fragments (scFv) with a molecular weight of 25 KDa. The GSSSSx3 (SEQ ID NO:47) linker was used to link the variable regions from heavy (VH) and light (VL) chains. PMS208 was expressed with and without his-tag for tests.

Example 4

PMS208-Fc Immunoprecipitates α-Syn from PD Patients' Sera and PD/DLB Patients' CSF The main component of pathological lesions (almost 90%) in patients with Parkinson's Disease (PD) is extensively phosphorylated at α-syn serine 129 (pS129 α-syn), which may play a critical role in synucleinopathy pathogenesis. Phosphorylation at Ser129 can regulate α-syn fibril formation and enhance α-syn toxicity both in vitro and in vivo. Although trace levels of phosphorylated α-syn are detectable in normal brains, nearly all α-syn accumulated within Lewy bodies in Parkinson disease brains is phosphorylated on serine 129 (Ser-129). Phosphorylated α-syn can be secreted from neuronal cells and can be seen in the serum and CSF of PD patients.

Human serum derived from PD patients and human CSF derived from Lewy Body Dementia (DLB) or PD patients were immunoprecipitated with PMS208-Fc to determine its ability to bind endogenous human alpha-synuclein. Three different amounts of PMS208-Fc (50 µg, 10 µg, and 5 µg) were able to immunoprecipitate α-syn from PD patients sera and DLB/PD patients CSF (FIGS. 7A and 7B). Samples were stained with a commercial anti-human α-syn (FIG. 7A, left panel) and anti-human phosphorylated (Ser-129) α-syn (FIG. 7A, right panel and FIG. 7B). Human recombinant PFF immunoprecipitation with PMS208-Fc was done as positive control for α-syn binding (FIG. 7A, left panel and FIG. 7B) and negative control for serine 129 α-syn phosphorylation (there is no phosphorylation in serine 129, seen in FIG. 7A, right panel and FIG. 7B).

Example 5

PMS208 Protects Human Neuronal Cells from PFF and from Oligomer Induced Toxicity The cytotoxicity of α-syn fibrils and oligomers was assessed on differentiated human neuroblastoma SH-SY5Y cells using the 3-(4,5-dimethylthiazol-2-yl)-2,5-diphenyltetrazolium bromide (MTT) assay (FIGS. 9A-C). Fibrillar α-syn and α-syn oligomers had a toxic effect on cells in low concentrations as seen by the cell viability assay (FIGS. 9A-C). Incubation of PFF α-syn in the presence of increasing concentrations of PMS208, showed increase in cell viability in a dose dependent manner, while no affect was seen in the presence of sham (80R) (FIG. 8A). Incubation of α-syn oligomers in the presence of increasing concentrations of PMS208, showed high increase in cell viability in concentration of 10 ug/ml (~76%) and similar slight increase in 6 ug/ml, 4 ug/ml and 1 ug/ml concentrations of PMS208 (~35%). PMS208 concentration of 0.2 ug/ml had no effect in cell viability (FIG. 8B). Human PD brain extracts (1:1000 in PBS) had a toxic affect on cells compared to control extracts (data not shown). PMS208 was able to protect cells as evidenced by increasing cell viability as seen in FIG. 8C.

Example 6

PMS208 Avidly Binds Brain Tissues from Patients with PD/DLB by WB

PMS208 (scFv) was able to bind avidly its target alpha-synuclein in a number of human brain (striatum, cortex) PD, DLB, and control extracts seen in Western blot staining (FIGS. 10A and 10B), demonstrating its ability to recognize modified forms of α-syn in multiple patients with synucleinopathies.

Example 7

PMS208 Attenuates Neuroinflammation Induced by Oligomers and PFF in Human PBMC's and Microglia Microglia is one of the major cell types which are involved in the inflammatory responses in the central nervous system (CNS) that appear to contribute to neuroinflammation in PD pathogenesis. This pro-inflammatory local state is evident by expression of tumor necrosis factor-α (TNF-α; TNFα), interleukin-1 (IL-10), and interferon-gamma (IFN-7) in the midbrain of PD patients which strongly suggest the involvement of immune components in PD pathogenesis.

Figure 11A:
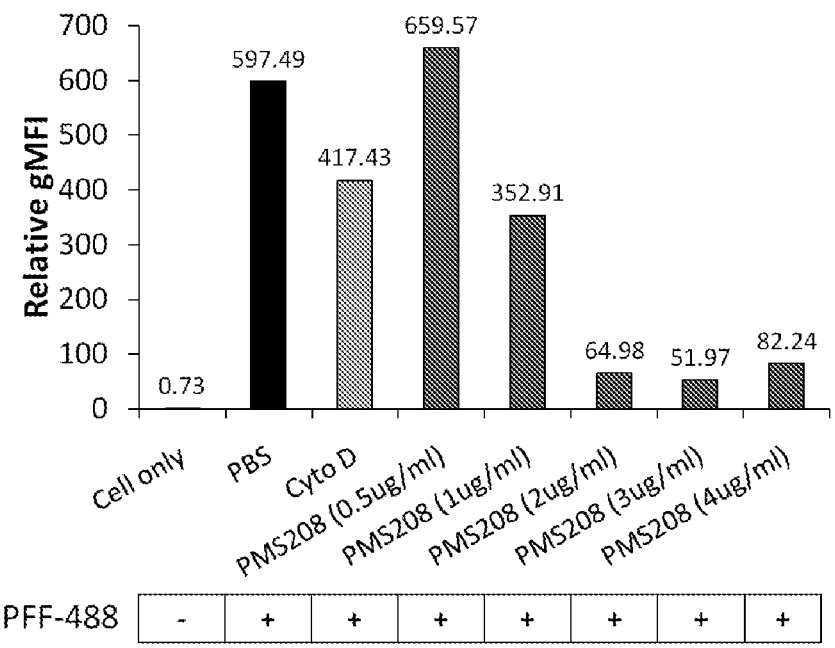
Figure 11B:
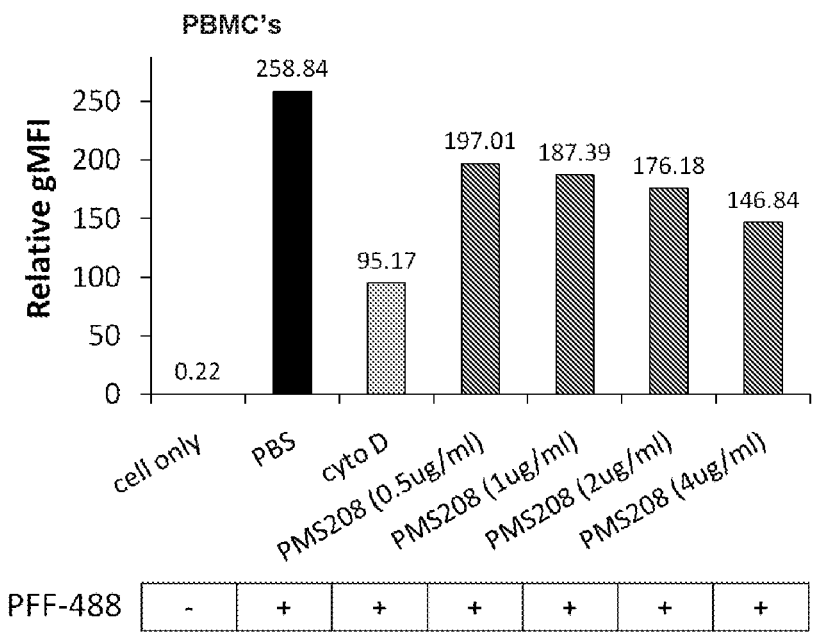
Figure 11C:
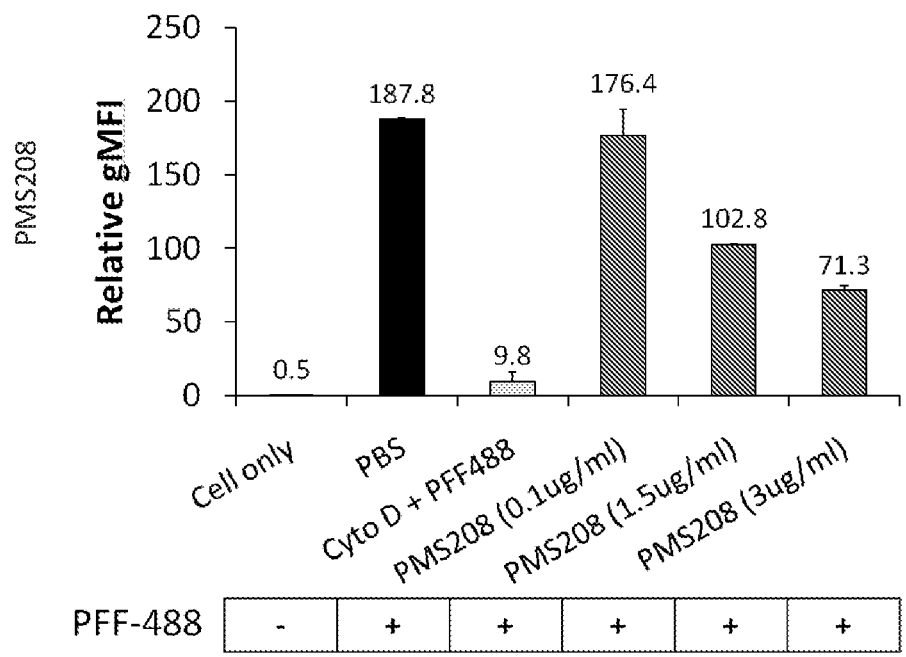
Figure 11D:
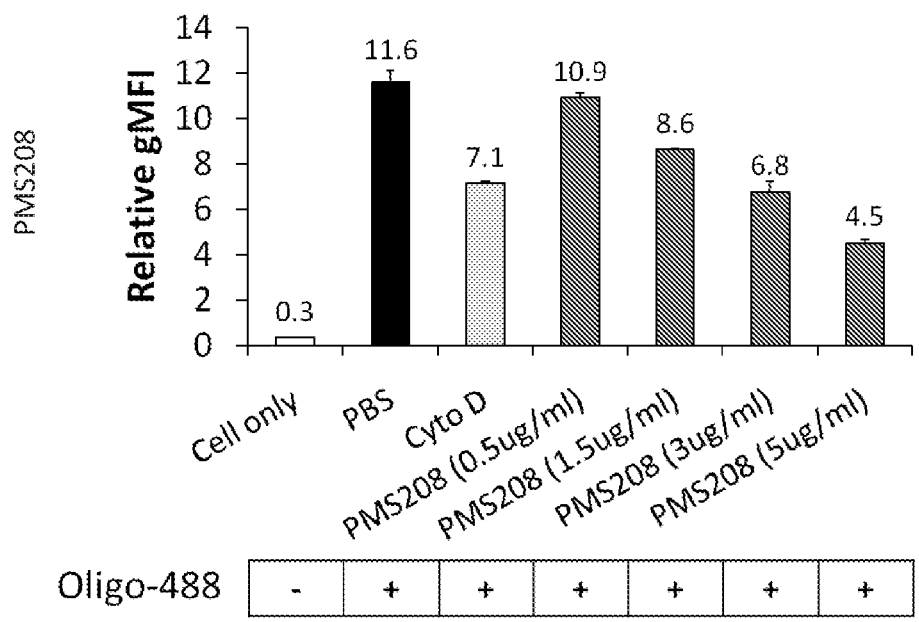
Figure 11E:
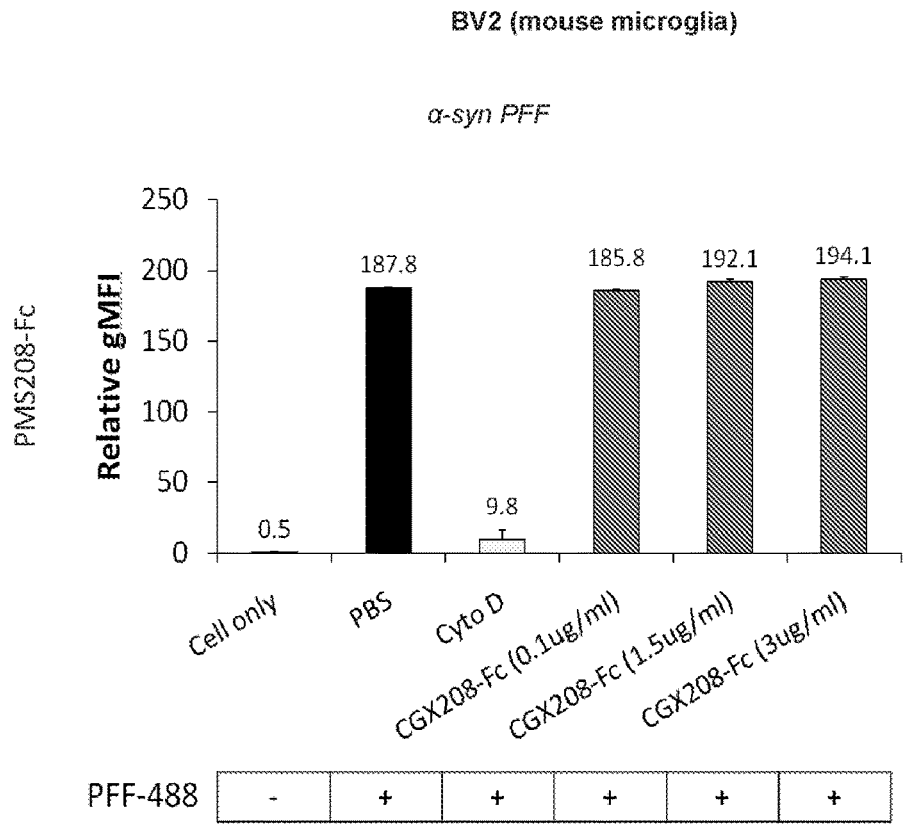
Figure 11F:
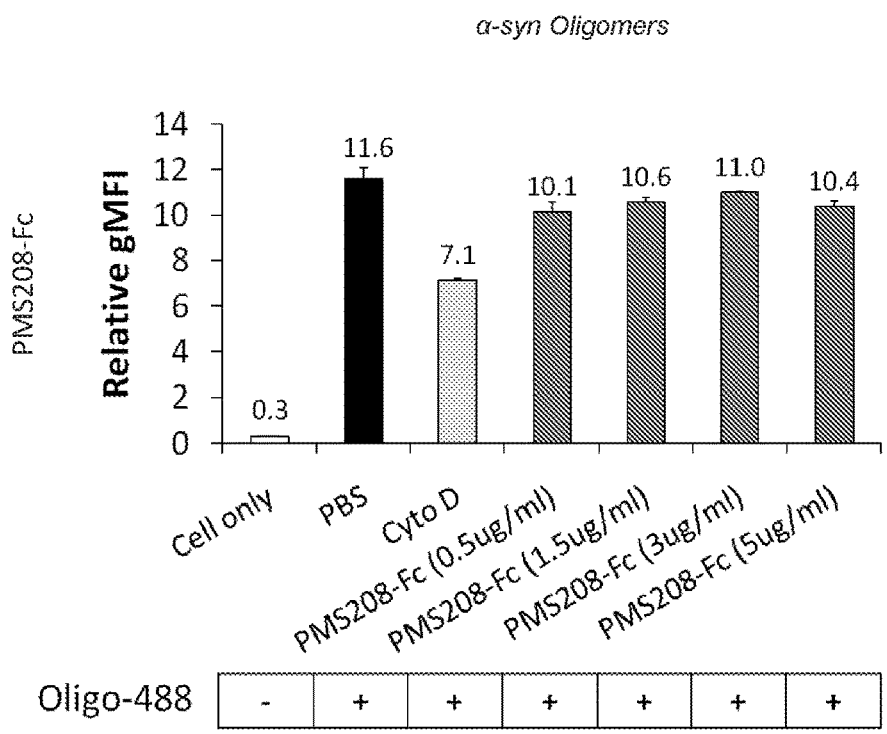

The scFv form of PMS208 down-regulates (in a dose dependent manner) a panel of pro-inflammatory cytokines (TNF-α, IL-6) produced by microglia after exposure to PFF, whereas Fc containing anti-aSyn antibodies up-regulate these same panel of proteins (FIGS. 11E and 11F). Monocytes range from 10-30% of human PBMCs, these cells move into tissues throughout the body where they differentiate into macrophages and dendritic cells. They serve three main functions in the immune system: antigen presentation, phagocytosis, and cytokine production. FIGS. 11A-C shows that PMS208 down-regulates (in a dose dependent manner) pro-inflammatory cytokine TNF-α produced by human peripheral blood macrophages after PFF or oligomers alpha-synuclein exposure compared to Fc containing anti-aSyn antibodies which up-regulate TNF-α mRNA and protein levels (FIGS. 11E and 11F).

Example 8

PMS208 Attenuates Cellular Uptake of Alpha-Synuclein Oligomers and PFF in Human PBMCs and Mouse Microglia One of the main functions of macrophages and microglia in the immune system is phagocytosis thereby facilitating clearance of debri. They can also serve as antigen presenting cells that promote T cell mediated cellular immunity. Recently, it has also been shown that PD patients exhibit a systemic autoimmune response to α-syn modified forms further attesting to the role of inflammation in the pathogenesis. Activation of microglia by dying neurons or by various forms of α-syn, as well as T cells, could result in a vicious circle of neuroinflammation and neurodegeneration that is self perpetuating and drives the progression of PD. Flow cytometry was used to measure PFF/oligomers conjugated to Alexa fluor 488 (PFF-488/Oligo-488) cellular uptake (calculated by relative geomean fluorescent intensity (gMFI)) (FIGS. 11A-11F).

Flow cytometry analysis shows that PMS208 in scFv format attenuates mouse and human macrophages cellular uptake of PFF conjugated to Alexa fluor 488 (relative gMFI~60) compared to cells with PBS treatment (relative gMFI~590) seen in FIGS. 12A and 12B. FIGS. 11C-F shows that PMS208 in scFv format attenuates mouse microglia cellular uptake of PFF (FIG. 11C) and oligomers (FIG. 11D) conjugated to Alexa fluor 488 (FIGS. 11C and 11D) in a dose dependent manner, whereas Fc containing antibodies does not (FIGS. 11E and 11F).

Example 9

PMS208 Attenuates Neuroinflammation In Vivo in Murine Cortex of Animals Injected with PFF and Oligomers Mice were injected with human α-syn PFF into the striatum (with and without PMS208 treatment) to examine in vivo neuroinflammation.

The scFv form of PMS208 down-regulated a panel of pro-inflammatory cytokines and up-regulated anti-inflammatory genes produced in mice brain after 72 hours of exposure to human PFF (FIGS. 12A and 12C) or oligomers (FIGS. 12B and 12D) alpha-synuclein. FIG. 12A shows that PMS208 significantly down-regulates IL-6, IL-12, and INFγ pro-inflammatory cytokines mRNA expression levels after PFF exposure. FIG. 12B shows that PMS208 significantly down-regulates TNFα and INFγ pro-inflammatory cytokines mRNA expression levels after oligomers exposure. Whereas, FIG. 12C shows that PMS208 significantly up-regulates Arg1 (Arginase 1) and Chi313 (Yml) mRNA expression levels after PFF exposure. FIG. 12D shows that PMS208 significantly up-regulates Arg1 and Chi313 mRNA expression levels after oligomers exposure.

Example 10

PMS208 Attenuates Neuroinflammation by Tuning Down the Autoimmune Response of T Cells to Oligomers/PFF as Evident by IL-5 and IFN-g ELISpots α-synuclein aggregated forms act as antigenic epitopes and drive helper and cytotoxic T cell responses in patients with Parkinson's disease. To determine whether α-syn pff/oligomers were recognized by T cells, HLA class I type and HLA class II responses were assayed. IFNγ was used as a representative cytokine to detect CD8$^+$HLA class I and CD4$^+$ T helper 1 (Th1) class II T cells, and IL-5 was used as a representative cytokine secreted by CD4$^+$T helper 2 (Th2) class II T cells. Peripheral blood mononuclear cells (PBMCs) from patients with Parkinson's disease were stimulated for 14 days (PFF/oligomers at 10 g/ml, diluted 1:1 every 3-4 days). These cultures were then stimulated with α-synuclein PFF/oligomers (25 µg/ml) with and without PMS208 (15 g/ml) and Interferon-T (IFNγ) or interleukin-5 (IL-5) responses were measured by colour enzyme-linked immunospot (ELISPOT) assay, enabling quantification of responsive T cells.

Fourteen (14) days of α-synuclein oligomers PBMCs stimulation compared to un-stimulated PBMCs (PBS) increased the number of IL-5 secreted cells when re-exposed to α-synuclein oligomers (FIG. 13A), indicating a prominent CD4$^+$Th2 phenotype. The addition of PMS208 (5 ug/ml and 2 ug/ml) to α-synuclein oligomers managed to tune down by half the autoimmune response as seen in FIG. 13A. PBMCs response to the α-synuclein PFF after 14 days of PFF stimulation increased twice the number of IFNγ secreted cells (FIG. 13C) compared to un-stimulated PBMCs (PBS), indicating a prominent CD8$^+$ HLA class I and CD4$^+$T helper 1 (Th1) class II T cells phenotype. The addition of PMS208 (5 ug/ml) to α-synuclein PFF tuned down the autoimmune response.

Example 12

PMS208 Inhibits α-Syn Aggregation In Vitro

Aggregation of misfolded proteins is a feature common to many neurodegenerative diseases. Parkinson's Disease is a progressive movement disorder which is characterized neuropathologically by the presence of intra-neuronal Lewy Bodies (LB) and Lewy Neurites (LN). Misfolded and aggregated alpha-synuclein (fibrillar alpha-synuclein) is major component of LB's and LN's.

Misfolded proteins are rich in β-sheet structures with a high tendency to form long fibrillar aggregates known as amyloid deposits. β-structures are harder to degrade than α-helixes (main conformation of native proteins), which explains why amyloid deposits cannot be removed by the proteasome system. The aggregation of misfolded proteins is believed to occur when hydrophobic residues exposed at the surface of proteins interact with other misfolded proteins. Human recombinant alpha-synuclein monomers can be driven to aggregate by constant shaking (orbital shaker) 1000 rpm at 37'C for 7 days (FIG. 14). As seen in FIG. 14, PMS208 (aSyn+PMS208 7.5 ug/ml and aSyn+PMS208 15 ug/ml) has the ability to inhibit alpha-synuclein aggregation (measured by Thioflavin T aggregated protein staining assay), whereas alpha-synuclein without PMS208 (aSyn+PBS) aggregates. Alpha-synuclein monomers were measured at each time point for reference (monomer).

Example 13

PMS208 Abrogates Spreading and Seeding of Human PFF In Vitro

Evidence suggests that many neurodegenerative diseases involve spreading aggregation of specific proteins through the nervous system, potentially via a prion-like mechanism. Prion proteins propagate by auto-catalytic conversion of native, nonpathogenic forms of the protein expressed in several types of human cells, into misfolded pathological conformation. In prion disease, the pathological conformation is the primary infectious agent that propagates using a mechanism called "seeding/nucleation," where misfolded pathological form of the protein acts like a seed that recruits and converts soluble protein into aggregates of native-nonpathogenic protein, which form polymers. As prions grow and spread, they interfere with the function of the nervous system, resulting in progression of the disease in affected patients.

Synucleinopathies are typified by pathologically aggregated alpha-synuclein in specific neuronal (e.g., Parkinson's Disease and Dementia with Lewy Bodies) or glial (e.g., Multiple System Atrophy) populations where cell loss occurs. In this model, the ability of PMS208 to abrogate PFF seeding was tested. Small seeds of PFFs generated from recombinant α-syn were added directly to primary neurons with and without PMS208. These seeds of PFFs induced recruitment of endogenously expressed α-syn into abnormal, phosphorylated, insoluble and ubiquitinated aggregates. The formation of these aggregates from endogenous α-syn in primary neurons derived from wild-type, nontransgenic mice follows an initial lag phase of 2-4 days, which are then seen in the SDS extract of neuronal cells (insoluble protein) in the nitrocellulose membrane immunostaining (FIG. 15 upper panel—2% SDS Pellet). PMS208 was able to abrogate endogenous alpha-synuclein aggregation by inhibiting the human PFF prion-like mechanism (Red arrow; PFF+PMS208-upper panel). Higher levels of alpha-synuclein are seen the SDS extract after human PFF "seeding" without PMS208 (PFF-upper panel).

Example 14

Intranasal (IN) Administration of PMS208 Motor Dysfunction Induced by the aSyn Aggregation—Rotenone in Rats Causes of sporadic PD remain unknown. Epidemiological studies suggest that exposures to pesticides, metals and solvents are contributing risk factors. In general, most sporadic cases are believed to stem from a combination of environmental exposures and individual genetic susceptibility. Several useful animal models of PD exist, each with its own advantages and disadvantages. The rotenone model of PD provides certain advantages in modeling the pathogenesis of PD. In this model, systemic inhibition of mitochondrial complex I produces selective degeneration of the nigrostriatal dopamine system and reproduces key pathological features of clinical PD. Indeed, rotenone administration affects many of the pathogenic pathways including: oxidative stress, alpha-synuclein phosphorylation and aggregation and Lewy pathology, DJ-1 acidification and translocation, proteasomal dysfunction and nigral iron accumulation.

Daily intraperitoneal injections of rotenone in natural oil (olive oil) were done for 12 days in 20 animals. 4 animals were injected with natural oil only as a control group. Animals were treated by intranasal (i.n.) administration of PMS208 (~40 ug/kg) and PBS as sham at day 1, 4, 7, and 10. Animal weight was measured each day in order to calculate % change in mass (FIG. 16A). PMS208 i.n. treatment was able to significantly reduce loss of weight as shown in FIG. 16A (Rotenone+PMS208) at days 9-12. Animals were placed in a clear cylinder to quantify rearing behavior (forelimbs contact with the wall of the cylinder). Animals treated i.n. with PMS208 were able to minimize decrease in rearing behavior (FIG. 16B; rotenone+PMS208) as seen in sham treated animals (FIG. 16B; Rotenone+sham) at day 12 compared to day 0.

Example 15

PMS208 Intranasal Treatment Attenuates Motor Dysfunction Induced by Intracerebral Injections of AAV-aSyn in Rats An ideal model would replicate most, if not all, of the behavioral and pathologic characteristics of PD. Traditional models of PD include neurotoxin models, such as 6-hydroxydopamine or MPTP, to lesion dopamine neurons of the SNpc (substantia nigra pars compacta). These models can successfully predict the efficacy of dopaminergic-based therapeutics to alleviate motor symptoms. However, many compounds that showed neuroprotection in the neurotoxin models have failed in clinical trials. Toxin models did not sufficiently take into account the contribution of pathologic α-synuclein. The progressive time course of the α-synuclein models has provided interesting data suggesting that synaptic abnormalities in the striatum precede neurodegeneration. One of the greatest advantages of the rAAV-α-synuclein model is that α-synuclein can be expressed in dopaminergic neurons of the SNpc for long periods of time (a cell population particularly vulnerable in PD). Expression of the human wild-type α-synuclein leads to progressive loss of dopaminergic neurons in the SNpc, and loss of dopamine terminals in the striatum. Showing significant defects in motor behavior. The rapid early loss of striatal dopamine function seen in the rAAV-α-synuclein model replicates the pattern seen in human disease. Furthermore, neuroinflammation is one of the most robust phenotypes found by rAAV-α-synuclein over-expression, and replicates many features seen in human PD. These changes include early activation of microglia, increased pro-inflammatory cytokine expression, increased adaptive and innate immune responses, and infiltration of lymphocytes before cell loss. This inflammatory induction is caused by over-expression of α-synuclein, and not the virus itself, because control mice injected with rAAV-green fluorescent protein (GFP) do not show neuroinflammatory responses. The increase in inflammation likely contributes to neurodegeneration. Thus, targeting signaling in the inflammatory pathway may provide a therapeutic target that can prevent the progression for PD.

Testing neuromuscular strength, FIG. 17A shows that 6-8 weeks post intra-striatal injections of rAAV-α-synuclein in rats, reduced their latency to fall (+AAV-aSyn+PBS; ~3.5 sec) in a wire hang test compared to sham injected animals (−AAV-aSyn+PBS; ~15 sec). Intranasal repeated treatments of PMS208 (twice a week) in rats post intra-striatal injections of rAAV-α-synuclein were able to attenuate motor dysfunction by significantly increasing the animals latency to fall (+AAV-aSyn+PMS208 (50 ug/kg); ~9:00 sec). It is important to note that rAAV-α-synuclein is typically unilaterally injected because tests of asymmetric motor behavior can be easily quantified (tests rely on asymmetry in motor behavior produced by unilateral losses of dopamine neuron function). The cylinder test is one of the tests that also measures asymmetry in use of forelimbs. In this experiment, rats had intrastriatal injections of AAV-α-synuclein (unilaterally) in the right hemisphere. FIG. 17B shows a decrease in left paw use of AAV-α-synuclein injected animals (+AAV-aSyn+PBS) compared to sham (−AAV-aSyn+PBS; ~8% increase). PMS208 i.n. treatment (5 ug/kg) was able to increase left paw use of AAV-α-synuclein injected animals (+AAV-aSyn+PMS208; ~7%).

Example 16

PMS208 Treatment Attenuates Motor Dysfunction in the Mouse PFF IC PD Model

Sonicated fibrils made from recombinant α-synuclein, when added to primary cultured neurons or injected into the striatum or other brain areas, can produce robust formation of inclusions that resemble Lewy bodies and Lewy neurites found in diseased brains. Thus, this model of PFF injection allows investigation of the impact of misfolded α-synuclein on the neuronal function and consequent phenotypes, and determination of whether preventing inclusion formation can reverse these phenotypes. Similar to rAAV-a-synuclein models, inducing inclusion formation with protein fibrils is advantageous because transgenic over-expression of human α-synuclein is not required. Inclusion formation occurs in neurons from hippocampus, cortex, and midbrain and other brain regions, and thus the impact of these aggregates on diverse neuronal populations can be examined. Regardless of the injection site, α-synuclein inclusions form at the injection site and appear in brain areas distant from the site of injection. In this model, defects occur well before any neuron death, suggesting that neuronal dysfunction emerges in response to abnormal α-synuclein very early before neurodegeneration begins. This is important in light of the development of novel techniques showing the presence of a-synuclein aggregates at a very early stage in brains of patients with PD and dementia with Lewy bodies.

As shown in FIGS. 18A and 18B, mice were evaluated for their latency to fall 12 weeks post intra-striatal mouse α-syn PFF injections. Wire hang was used to test neuromuscular strength. Animals injected with mouse PFF and i.n. treated with PBS (FIG. 18A; +mouse PFF+PBS; ~8:30 min) had significantly lower latency than animals injected with PBS and treated i.n. with PBS used as control (−mouse PFF+PBS; ~12:00 min). PMS208 i.n. treated animals showed significantly increase in their latency to fall (+mouse PFF+PMS208 (320 ug/kg); ~12:00 min) compared to untreated animals (+mouse PFF+PBS; ~8:30 min). The rotarod treadmill was used to assess fine motor coordination and balance in treated mice. Three different concentrations of i.n. treatment of PMS208 (16 ug/kg, 80 ug/kg, and 320 ug/kg) increased significantly mice latency to fall (+mouse PFF+PMS208; ~120 sec) compared to untreated animals with mouse PFF intra-striatal injections (+mouse PFF+PBS; ~50 sec). FIG. 18C shows cognitive decline of mouse PFF injected animals (+mouse PFF+PBS) compare to PBS injected controls (−mouse PFF+PBS) measured by their preference to a novel object. Above 50% (FIG. 18C), animal preference is for the novel object (less cognitive decline). Intranasal treatment with PMS208 (+mouse PFF+PMS208 (320 ug/kg); ~65%) significantly improved cognitive decline compare to untreated animals (+mouse PFF+PBS; ~45%). The experiment was done in 50 animals, 10 animals per group (n=10).

Example 19

PMS208 Affects TH+ Neurons and Dopaminergic (DA) Neurons

FIG. 19 shows that animals injected with adeno-associated virus expressing human aSyn (AAV-aSyn) develop extensive and significantly greater loss of $TH^+$ neurons in SN pars compacta (SNc) and striatum 6 weeks post injections as seen in tyrosine hydroxylase immunostaining of brain coronal slices (FIG. 19—middle panel; right hemisphere (RH)). PMS208 given intra-nassaly (i.n.—twice a week) decreases loss of $TH^+$ nigral neurons induced by AAV-aSyn in rats (FIG. 19—right panel). There is no loss of $TH^+$ neurons seen in sham injected animals 6 weeks post injections (FIG. 19—left panel). Human alpha-synuclein levels in coronal rat brain slices was confirmed by immunostaining.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated antibody or antigen-binding fragment thereof that binds to soluble monomers, oligomers, and/or preformed fibrils of alpha-synuclein, wherein the antibody or antigen-binding fragment thereof comprises a complementary determining region (CDR) H1 comprising the amino acid sequence set forth in SEQ ID NO:1 (GGSISSHY), a CDR H2 comprising the amino acid sequence set forth in SEQ ID NO:2 (IYDSGST), a CDR H3 comprising the amino acid sequence set forth in SEQ ID NO:3 (AR-GAGWYRF), a CDR L1 comprising the amino acid sequence set forth in SEQ ID NO:4 (QSVLYSSNNKNY), a CDR2 L2 comprising the amino acid sequence set forth in SEQ ID NO:5 (WAS), and a CDR3 L3 comprising the amino acid sequence set forth in SEQ ID NO:6 (QQYYSTPRT).

2. The antibody or antigen-binding fragment thereof of claim 1, wherein the antibody or antigen-binding fragment thereof comprises a heavy chain variable region (VH) a light chain variable region (VL), wherein the VH comprises the same amino acid sequence as the VH encoded by the plasmid of ATCC Deposit Designation PTA-125004, and wherein the VL comprises the same amino acid sequence as the VL encoded by the plasmid of ATCC Deposit Designation PTA-125004.

3. An antibody or antigen-binding fragment thereof that binds to soluble monomers, oligomers, and/or preformed fibrils of alpha-synuclein, wherein the antibody or antigen-binding fragment thereof comprises CDR H1, CDR H2, CDR H3, CDR L1, CDR L2, and CDR L3 comprising the CDR H1, CDR H2, CDR H3, CDR L1, CDR L2, and CDR L3 amino acid sequences encoded by the plasmid of ATCC Deposit Designation PTA-125004.

4. An antibody or antigen-binding fragment thereof that binds soluble monomers, oligomers, and/or preformed fibrils of alpha-synuclein, wherein the antibody or antigen-binding fragment thereof comprises CDR H1, CDR H2, CDR H3, CDR L1, CDR L2, and CDR L3 comprising the CDR H1, CDR H2, CDR H3, CDR L1, CDR L2, and CDR L3 amino acid sequences of PMS209, PMS210, PMS211, PMS212, or PMS213,
   wherein PMS209 comprises a VH comprising the mature form of the amino acid sequence set in SEQ ID NO: 21 and a VL comprising the mature form of the amino acid sequence set forth in SEQ ID NO: 22;
   wherein PMS210 comprises a VH comprising the mature form of the amino acid sequence set in SEQ ID NO: 25 and a VL comprising the mature form of the amino acid sequence set forth in SEQ ID NO: 26;
   wherein PMS211 comprises a VH comprising the mature form of the amino acid sequence set in SEQ ID NO: 29 and a VL comprising the mature form of the amino acid sequence set forth in SEQ ID NO: 30;
   wherein PMS212 comprises a VH comprising the mature form of the amino acid sequence set in SEQ ID NO: 33 and a VL comprising the mature form of the amino acid sequence set forth in SEQ ID NO: 34; and
   wherein PMS213 comprises a VH comprising the mature form of the amino acid sequence set in SEQ ID NO: 37 and a VL comprising the mature form of the amino acid sequence set forth in SEQ ID NO: 38.

5. The antibody or antigen-binding fragment thereof of claim 4, wherein the antibody or antigen binding fragment thereof comprises a VH and a VL,
   wherein the VH and VL comprise the mature forms of SEQ ID NOs: 21 and 22, respectively, SEQ ID NOs: 25 and 26, respectively, SEQ ID NOs: 29 and 30, respectively, SEQ ID NOs: 33 and 34, respectively, or SEQ ID NOs: 37 and 38, respectively.

6. The antigen-binding fragment of an antibody of claim 1, wherein said antibody is an antigen-binding fragment of an antibody, wherein the antigen-binding fragment is selected from the group consisting of Fab, F(ab')2, Fv, scFv, scFv-Fc, and dsFv.

7. The antigen-binding fragment of an antibody of claim 6, wherein said fragment is an scFv.

8. The antibody or antigen-binding fragment thereof of claim 4, wherein the antibody or antigen-binding fragment thereof comprises the amino acid sequence of the mature form of SEQ ID NOs: 42 or 44.

9. The antibody or antigen-binding fragment thereof of claim 1, that inhibits expression and/or secretion of pro-inflammatory cytokines from microglia cells incubated with misfolded alpha synuclein, that inhibits uptake of misfolded alpha synuclein by macrophages, that inhibits T cell activation by misfolded alpha synuclein, that prevents aggregation of alpha-synuclein as determined by Thioflavin T (ThT), that inhibits seeding and spreading of alpha-synuclein, that penetrates neurons, that colocalizes with misfolded alpha synuclein and attenuates and/or that ameliorates a motorical or physiological phenotype in a synucleinopathy mouse model.

10. A composition comprising the antibody or antigen-binding fragment thereof of claim 1 and a carrier, wherein the composition is a diagnostic composition, a therapeutic composition, or a vaccine.

11. A vector comprising a first nucleic acid molecule encoding the heavy chain variable region or heavy chain of the antibody or antigen-binding fragment thereof of claim 1 and a second nucleic acid molecule encoding the light chain variable region or light chain of the antibody or antigen-binding fragment thereof of claim 1.

12. The vector of claim 11, wherein the vector is a viral vector.

13. A host cell comprising the vector of claim 11.

14. A pharmaceutical composition comprising the antibody or antigen-binding fragment thereof of claim 1.

15. A method of producing an alpha-synuclein antibody or antigen-binding fragment thereof, the method comprising:
   (a) culturing the cell of claim 13 in a cell culture under conditions which allow expression of said an alpha-synuclein antibody or antigen-binding fragment thereof; and
   (b) recovering the antibody or antigen-binding fragment thereof from said cell culture.

16. An alpha-synuclein antibody or antigen-binding fragment thereof obtainable by the method of claim 15.

17. A method of treating a synucleinopathic disease in a subject, the method comprising administering to the subject a therapeutically effective amount of the antibody or antigen-binding fragment thereof of claim 1, thereby treating the synucleinopathic disease.

18. A method of treating neuroinflammation in a subject, the method comprising administering to the subject a therapeutically effective amount of the antibody or antigen-binding fragment thereof of claim 1, thereby treating the neuroinflammation.

19. A method of diagnosing a synucleinopathic disease in a subject, comprising:
   (a) assessing the level, localization, conformation or a combination thereof of misfolded alpha-synuclein in a subject to be diagnosed with the antibody or antigen-binding fragment thereof of claim 1;
   (b) comparing the level, localization, conformation or combination thereof of misfolded alpha-synuclein in the subject to one or more reference standards derived from one or more control samples,
   wherein a difference or similarity between the level, localization, conformation or combination thereof of alpha-synuclein in the subject and the reference standard indicates whether the subject has a synucleinopathic disease.

20. A method of detecting misfolded alpha-synuclein, the method comprising:
   (a) contacting a biological sample with the antibody or antigen-binding fragment thereof of claim 1 under conditions which allow formation of immunocomplexes; and
   (b) determining the presence and/or level of said immunocomplexes.

* * * * *

UNITED STATES PATENT AND TRADEMARK OFFICE
CERTIFICATE OF CORRECTION

PATENT NO. : 11,512,125 B2
APPLICATION NO. : 17/255776
DATED : November 29, 2022
INVENTOR(S) : Michael Fassler and Jacob George It is certified that error appears in the above-identified patent and that said Letters Patent is hereby corrected as shown below:

In the Claims

In Column 94, Line 5, Claim 9, add "consequent cellular toxicity," after "attenuates"

Signed and Sealed this
Twenty-eighth Day of March, 2023

*Katherine Kelly Vidal*

Katherine Kelly Vidal
*Director of the United States Patent and Trademark Office*